US008859251B2

(12) United States Patent
Iadonato et al.

(10) Patent No.: US 8,859,251 B2
(45) Date of Patent: *Oct. 14, 2014

(54) OLIGOADENYLATE SYNTHETASE (OAS)

(71) Applicant: Kineta Two LLC, Seattle, WA (US)

(72) Inventors: Shawn P. Iadonato, Seattle, WA (US); Charles L. Magness, Seattle, WA (US); Mark Branum, Bellevue, WA (US); Maralee McVean, Seattle, WA (US); Christina Scherer, Seattle, WA (US)

(73) Assignee: Kineta Two, LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/933,019

(22) Filed: Jul. 1, 2013

(65) Prior Publication Data

US 2014/0005102 A1 Jan. 2, 2014

Related U.S. Application Data

(60) Division of application No. 13/364,140, filed on Feb. 1, 2012, now Pat. No. 8,486,678, which is a continuation of application No. 12/750,545, filed on Mar. 30, 2010, now Pat. No. 8,133,710, which is a division of application No. 11/601,440, filed on Nov. 17, 2006, now Pat. No. 7,732,177.

(60) Provisional application No. 60/752,668, filed on Dec. 21, 2005, provisional application No. 60/739,159, filed on Nov. 23, 2005.

(51) Int. Cl.
| | |
|---|---|
| *C12N 9/12* | (2006.01) |
| *C07H 21/04* | (2006.01) |
| *C12N 1/20* | (2006.01) |
| *A61K 38/45* | (2006.01) |
| *C12N 15/00* | (2006.01) |
| *C12N 15/10* | (2006.01) |

(52) U.S. Cl.
CPC ............ *C12N 9/1241* (2013.01); *C12N 15/102* (2013.01); *A61K 38/45* (2013.01); *C12Y 207/07* (2013.01)
USPC ...... 435/194; 435/440; 435/320.1; 435/252.3; 424/94.5; 536/23.2

(58) Field of Classification Search
CPC .... C12N 9/1241; C12N 15/102; A61K 38/45; C12Y 207/07
See application file for complete search history.

(56) References Cited

U.S. PATENT DOCUMENTS

| | | | |
|---|---|---|---|
| 5,766,897 A | 6/1998 | Braxton | 435/463 |
| 2003/0235575 A1 | 12/2003 | Matzuk et al. | 424/94.61 |
| 2004/0009152 A1 | 1/2004 | Mohapatra et al. | 424/93.2 |

FOREIGN PATENT DOCUMENTS

WO 2005/040428 6/2005

OTHER PUBLICATIONS

Branden et al., "Prediction, Engineering, and Design of Protein Structures," Introduction to Protein Structure, Garland Publishing, Inc., p. 247 (1991).
Delgado, et al., "The Uses and Properties of PEG-Linked Proteins," Critical Reviews in Therapeutic Drug Carrier Systems 9(3/4):249-304, 1992. (XP002930070).
Ghosh, et al., "Enzymatic Activity of 2'-5'-Oligoadenylate Synthetase is Impaired by Specific Mutations That Affect Oligomerization of the Protein," J. Biol. Chem. 272(52):33220-33226, 1997. (XP002444631).
Ghosh, et al., "Cell Growth Regulatory and Antiviral Effects of the P69 Isozyme of 2-5(A) Synthetase", Virology, Academic Press, Orlando, US, 266(2):319-328, 2000. (XP004436170).
Justesen, et al., "Gene Structure and Function of the 2'-5'-Oligoadenylate Synthetase Family," CMLS Cellular and Molecular Life Sciences 57(11):1593-1612, 2000. (XP001157584).
Ryser, et al., "Histones and Basic Polyamino Acids Stimulate the Uptake of Albumin by Tumor Cells in Culture," Science 150(695):501-503, 1965. (XP002444633).
Sarkar, et al., "The Nature of the Catalytic Domain of 2'-5'-Oligoadenylate Synthetases," J. Biol. Chem. 274(36):25535-25542, 1999. (XP002326605).
Sarkar, et. al., "Production, Purification, and Characterization of Recombinant 2', 5'-Oligoadenylate Synthetases" Methods: A Companion to Methods in Enzymology 15:233-242, 1998.
Search Report from PCT/US2006/044176 (mailed Sep. 20, 2007).
Search Report on Taiwanese Application No. 095141982 (performed on Apr. 10, 2012).
Torshin, "Three-Dimensional Models of Human '2-'5-0ligoadenylate Synthetases: A New Computational Method for Reconstructing an Enzyme Assembly," Medical Science Monitor: International Medical Journal of Experimental and Clinical Research 11(7):BR235-BR247, 2005. (XP002444632).

*Primary Examiner* — Yong Pak
(74) *Attorney, Agent, or Firm* — Lee & Hayes, PLLC; C. Rachal Winger

(57) ABSTRACT

The invention describes novel pharmaceutical compositions for the treatment of virus infections and cancer. The pharmaceutical compositions include mutant oligoadenylate synthetases (OAS) that have either enhanced cell permeability, reduced oxidative potential, improved antiviral activity, improved enzymatic activity, or absent enzymatic activity. The pharmaceutical compositions have improved drug properties and retain or have enhanced antiviral activity relative to their native forms. The pharmaceutical compositions further include chemically modified oligoadenylate synthetases, such chemical modifications being designed to increase serum stability and reduce immunogenicity in vivo. Such chemical modifications further increase drug stability and manufacturability in vitro. Compositions composed of more than ninety novel modifications are described. Also described are antibodies to polypeptides of the invention.

14 Claims, 14 Drawing Sheets

FIGURE 1

NOVEL PHARMACEUTICAL COMPOSITIONS

SEQUENCE:1 (Reference Polypeptide)

```
  1 MMDLRNTPAK SLDKFIEDYL LPDTCFRMQI NHAIDIICGF LKERCFRGSS YPVCVSKVVK
 61 GGSSGKGTTL RGRSDADLVV FLSPLTTFQD QLNRRGEFIQ EIRRQLEACQ RERAFSVKFE
121 VQAPRWGNPR ALSFVLSSLQ LGEGVEFDVL PAFDALGQLT GGYKPNPQIY VKLIEECTDL
181 QKEGEFSTCF TELQRDFLKQ RPTKLKSLIR LVKHWYQNCK KKLGKLPPQY ALELLTVYAW
241 ERGSMKTHFN TAQGFRTVLE LVINYQQLCI YWTKYYDFKN PIIEKYLRRQ LTKPRPVILD
301 PADPTGNLGG GDPKGWRQLA QEAEAWLNYP CFKNWDGSPV SSWILL
```

The novel pharmaceutical compositions of the present invention also include SEQUENCE:1 above modified by one or more of the modifications in the table below. For the modifications below denoted by a *, a subscript 'n' indicates a homopolymeric amino acid sequence of length n for the parenthesized amino acid, where n is any integer from 1 to 15, inclusive.

| Modification Number | Modification Class | Type of Modification | Utility of Modification | Amino Acid Position | Reference Amino Acid | Modification(s) to Reference Amino Acid |
|---|---|---|---|---|---|---|
| 1 | I | Amino Acid | Enzymatic inactivation | 75 | D, Asp | A, Ala |
| 2 | I | Amino Acid | Enzymatic inactivation | 77 | D, Asp | A, Ala |
| 3 | II | Amino Acid | Improved oxidation resistance | 25 | C, Cys | A, Ala |
| 4 | II | Amino Acid | Improved oxidation resistance | 25 | C, Cys | G, Gly |
| 5 | II | Amino Acid | Improved oxidation resistance | 25 | C, Cys | M, Met |
| 6 | II | Amino Acid | Improved oxidation resistance | 25 | C, Cys | S, Ser |

FIGURE 1 cont.

| | | | | | | |
|---|---|---|---|---|---|---|
| 7 | II | Amino Acid | Improved oxidation resistance | 25 | C, Cys | T, Thr |
| 8 | II | Amino Acid | Improved oxidation resistance | 25 | C, Cys | -(C, Cys Deleted) |
| 9 | II | Amino Acid | Improved oxidation resistance | 38 | C, Cys | A, Ala |
| 10 | II | Amino Acid | Improved oxidation resistance | 38 | C, Cys | G, Gly |
| 11 | II | Amino Acid | Improved oxidation resistance | 38 | C, Cys | M, Met |
| 12 | II | Amino Acid | Improved oxidation resistance | 38 | C, Cys | S, Ser |
| 13 | II | Amino Acid | Improved oxidation resistance | 38 | C, Cys | T, Thr |
| 14 | II | Amino Acid | Improved oxidation resistance | 38 | C, Cys | -(C, Cys Deleted) |
| 15 | II | Amino Acid | Improved oxidation resistance | 45 | C, Cys | A, Ala |
| 16 | II | Amino Acid | Improved oxidation resistance | 45 | C, Cys | G, Gly |
| 17 | II | Amino Acid | Improved oxidation resistance | 45 | C, Cys | M, Met |
| 18 | II | Amino Acid | Improved oxidation resistance | 45 | C, Cys | S, Ser |
| 19 | II | Amino Acid | Improved oxidation resistance | 45 | C, Cys | T, Thr |
| 20 | II | Amino Acid | Improved oxidation resistance | 45 | C, Cys | -(C, Cys Deleted) |
| 21 | II | Amino Acid | Improved oxidation resistance | 54 | C, Cys | A, Ala |
| 22 | II | Amino Acid | Improved oxidation resistance | 54 | C, Cys | G, Gly |

FIGURE 1 cont.

| | | | | | | |
|---|---|---|---|---|---|---|
| 23 | II | Amino Acid | Improved oxidation resistance | 54 | C, Cys | M, Met |
| 24 | II | Amino Acid | Improved oxidation resistance | 54 | C, Cys | S, Ser |
| 25 | II | Amino Acid | Improved oxidation resistance | 54 | C, Cys | T, Thr |
| 26 | II | Amino Acid | Improved oxidation resistance | 54 | C, Cys | - (C,Cys Deleted) |
| 27 | II | Amino Acid | Improved oxidation resistance | 109 | C, Cys | A, Ala |
| 28 | II | Amino Acid | Improved oxidation resistance | 109 | C, Cys | G, Gly |
| 29 | II | Amino Acid | Improved oxidation resistance | 109 | C, Cys | M, Met |
| 30 | II | Amino Acid | Improved oxidation resistance | 109 | C, Cys | S, Ser |
| 31 | II | Amino Acid | Improved oxidation resistance | 109 | C, Cys | T, Thr |
| 32 | II | Amino Acid | Improved oxidation resistance | 109 | C, Cys | - (C,Cys Deleted) |
| 33 | II | Amino Acid | Improved oxidation resistance | 177 | C, Cys | A, Ala |
| 34 | II | Amino Acid | Improved oxidation resistance | 177 | C, Cys | G, Gly |
| 35 | II | Amino Acid | Improved oxidation resistance | 177 | C, Cys | M, Met |
| 36 | II | Amino Acid | Improved oxidation resistance | 177 | C, Cys | S, Ser |
| 37 | II | Amino Acid | Improved oxidation resistance | 177 | C, Cys | T, Thr |
| 38 | II | Amino Acid | Improved oxidation resistance | 177 | C, Cys | - (C,Cys Deleted) |

FIGURE 1 cont.

| 39 | II | Amino Acid | Improved oxidation resistance | 189 | C, Cys | A, Ala |
| --- | --- | --- | --- | --- | --- | --- |
| 40 | II | Amino Acid | Improved oxidation resistance | 189 | C, Cys | G, Gly |
| 41 | II | Amino Acid | Improved oxidation resistance | 189 | C, Cys | M, Met |
| 42 | II | Amino Acid | Improved oxidation resistance | 189 | C, Cys | S, Ser |
| 43 | II | Amino Acid | Improved oxidation resistance | 189 | C, Cys | T, Thr |
| 44 | II | Amino Acid | Improved oxidation resistance | 189 | C, Cys | - (C,Cys Deleted) |
| 45 | II | Amino Acid | Improved oxidation resistance | 219 | C, Cys | A, Ala |
| 46 | II | Amino Acid | Improved oxidation resistance | 219 | C, Cys | G, Gly |
| 47 | II | Amino Acid | Improved oxidation resistance | 219 | C, Cys | M, Met |
| 48 | II | Amino Acid | Improved oxidation resistance | 219 | C, Cys | S, Ser |
| 49 | II | Amino Acid | Improved oxidation resistance | 219 | C, Cys | T, Thr |
| 50 | II | Amino Acid | Improved oxidation resistance | 219 | C, Cys | - (C,Cys Deleted) |
| 51 | II | Amino Acid | Improved oxidation resistance | 269 | C, Cys | A, Ala |
| 52 | II | Amino Acid | Improved oxidation resistance | 269 | C, Cys | G, Gly |
| 53 | II | Amino Acid | Improved oxidation resistance | 269 | C, Cys | M, Met |
| 54 | II | Amino Acid | Improved oxidation resistance | 269 | C, Cys | S, Ser |

FIGURE 1 cont.

| | | | | | | |
|---|---|---|---|---|---|---|
| 55 | II | Amino Acid | Improved oxidation resistance | 269 | C, Cys | T, Thr |
| 56 | II | Amino Acid | Improved oxidation resistance | 269 | C, Cys | - (C,Cys Deleted) |
| 57 | II | Amino Acid | Improved oxidation resistance | 331 | C, Cys | A, Ala |
| 58 | II | Amino Acid | Improved oxidation resistance | 331 | C, Cys | G, Gly |
| 59 | II | Amino Acid | Improved oxidation resistance | 331 | C, Cys | M, Met |
| 60 | II | Amino Acid | Improved oxidation resistance | 331 | C, Cys | S, Ser |
| 61 | II | Amino Acid | Improved oxidation resistance | 331 | C, Cys | T, Thr |
| 62 | II | Amino Acid | Improved oxidation resistance | 331 | C, Cys | - (C,Cys Deleted) |
| 63 | III | Amino Acid | Enhanced cell permeability | 1 | M, Met | *(M, Met) - (H-His)n - (M, Met) |
| 64 | III | Amino Acid | Enhanced cell permeability | 1 | M, Met | *(M, Met) - (H-His)n |
| 65 | III | Amino Acid | Enhanced cell permeability | 1 | M, Met | *(M, Met) - (R-Arg)n - (M, Met) |
| 66 | III | Amino Acid | Enhanced cell permeability | 1 | M, Met | *(M, Met) - (R-Arg)n |
| 67 | III | Amino Acid | Enhanced cell permeability | 1 | M, Met | *(M, Met) - (K-Lys)n - (M, Met) |
| 68 | III | Amino Acid | Enhanced cell permeability | 1 | M, Met | *(M, Met) - (K-Lys)n |
| 69 | III | Amino Acid | Enhanced cell permeability | 1 | M, Met | *(M, Met) - (H-His)n - (G-Gly) - (M, Met) |
| 70 | III | Amino Acid | Enhanced cell permeability | 1 | M, Met | *(M, Met) - (H-His)n - (G, Gly) |

FIGURE 1 cont.

| | | | | | | |
|---|---|---|---|---|---|---|
| 71 | III | Amino Acid | Enhanced cell permeability | 1 | M, Met | *(M, Met) - (R-Arg)n - (G, Gly) - (M, Met) |
| 72 | III | Amino Acid | Enhanced cell permeability | 1 | M, Met | *(M, Met) - (R-Arg)n - (G, Gly) |
| 73 | III | Amino Acid | Enhanced cell permeability | 1 | M, Met | *(M, Met) - (K-Lys)n - (G, Gly) - (M, Met) |
| 74 | III | Amino Acid | Enhanced cell permeability | 1 | M, Met | *(M, Met) - (K-Lys)n - (G, Gly) |
| 75 | III | Amino Acid | Enhanced cell permeability | 1 | M, Met | (M, Met) - (G, Gly) - (H, His) - (H, His) - (H, His) - (H, His) - (H, His) - (H, His) - (H, His) - (H, His) - (H, His) - (H, His) - (S, Ser) - (S, Ser) - (G, Gly) - (H,His) - (I, Ile) - (E, Glu) - (G, Gly) - (R, Arg) - (H, His) - (M, Met) |
| 76 | IV | Chemical | Pegylation | 25 | C, Cys | (C, Cys)-PEG |
| 77 | IV | Chemical | Pegylation | 38 | C, Cys | (C, Cys)-PEG |
| 78 | IV | Chemical | Pegylation | 45 | C, Cys | (C, Cys)-PEG |
| 79 | IV | Chemical | Pegylation | 54 | C, Cys | (C, Cys)-PEG |
| 80 | IV | Chemical | Pegylation | 109 | C, Cys | (C, Cys)-PEG |
| 81 | IV | Chemical | Pegylation | 177 | C, Cys | (C, Cys)-PEG |
| 82 | IV | Chemical | Pegylation | 189 | C, Cys | (C, Cys)-PEG |
| 83 | IV | Chemical | Pegylation | 219 | C, Cys | (C, Cys)-PEG |
| 84 | IV | Chemical | Pegylation | 269 | C, Cys | (C, Cys)-PEG |

FIGURE 1 cont.

| 85 | IV | Chemical | Pegylation | 331 | C, Cys | (C, Cys)-PEG |
|----|----|----------|------------|-----|--------|--------------|
| 86 | V | Amino Acid | Mixed | 1 | M, Met | - (M, Met Deleted) |
| 87 | V | Amino Acid | Mixed | 31 | N, Asn | D, Asp |
| 88 | V | Amino Acid | Mixed | 115 | F, Phe | L, Leu |
| 89 | V | Amino Acid | Mixed | 127 | G, Gly | R, Arg |
| 90 | V | Amino Acid | Mixed | 162 | G, Gly | S, Ser |
| 91 | V | Amino Acid | Mixed | 280 | N, Asn | T, Thr |
| 92 | V | Amino Acid | Mixed | 330 | P, Pro | S, Ser |
| 93 | V | Amino Acid | Mixed | 346 | L, Leu | - (L, Leu Deleted) |

FIGURE 7

SEQUENCE: 2

```
   1 CCATGGGCCATCATCATCATCATCATCATCATCATCACAGCAGCGGCCATATCGAAGGTC
  61 GTCATATGATGGATCTCAGAAATACCCCAGCCAAATCTCTGGACAAGTTCATTGAAGACT
 121 ATCTCTTGCCAGACACGTGTTTCCGCATGCAAATCAACCATGCCATTGACATCATCTGTG
 181 GGTTCCTGAAGGAAAGGTGCTTCCGAGGTAGCTCCTACCCTGTGTGTGTCCAAGGTGG
 241 TAAAGGGTGGCTCCTCAGGCAAGGGCACCACCCTCAGAGGCCGATCTGACGCTGACCTGG
 301 TTGTCTTCCTCAGTCCTCTCACCACTTTTCAGGATCAGTTAAATCGCCGGGGAGAGTTCA
 361 TCCAGGAAATTAGGAGACAGCTGGAAGCCTGTCAAAGAGAGAGAGCATTTTCCGTGAAGT
 421 TTGAGGTCCAGGCTCCACGCTGGGGCAACCCCCGTGCGCTCAGCTTCGTACTGAGTTCGC
 481 TCCAGCTCGGGGAGGGGGTGGAGTTCGATGTGCTGCCTGCCTTTGATGCCCTGGGTCAGT
 541 TGACTGGCGGCTATAAACCTAACCCCCAAATCTATGTCAAGCTCATCGAGGAGTGCACCG
 601 ACCTGCAGAAAGAGGGCGAGTTCTCCACCTGCTTCACAGAACTACAGAGAGACTTCCTGA
 661 AGCAGCGCCCCACCAAGCTCAAGAGCCTCATCCGCCTAGTCAAGCACTGGTACCAAAATT
 721 GTAAGAAGAAGCTTGGGAAGCTGCCACCTCAGTATGCCCTGGAGCTCCTGACGGTCTATG
 781 CTTGGGAGCGAGGGAGCATGAAAACACATTTCAACACAGCCCAGGGATTTCGGACGGTCT
 841 TGGAATTAGTCATAAACTACCAGCAACTCTGCATCTACTGGACAAAGTATTATGACTTTA
 901 AAAACCCCATTATTGAAAAGTACCTGAGAAGGCAGCTCACGAAACCCAGGCCTGTGATCC
 961 TGGACCCGGCGGACCCTACACGGAAACTTGGGTGGTGGAGACCCAAAGGGTTGGAGGCAGC
1021 TGGCACAAGAGGCTGAGGCCTGGCTGAATTACCCATGCTTTAAGAATTGGGATGGGTCCC
1081 CAGTGAGCTCCTGGATTCTGCTGTGATCTGGATCC
```

SEQUENCE: 3

```
   1 CCATGGATCTCAGAAATACCCCAGCCAAATCTCTGGACAAGTTCATTGAAGACTATCTCT
  61 TGCCAGACACGTGTTTCCGCATGCAAATCAACCATGCCATTGACATCATCTGTGGGTTCC
 121 TGAAGGAAAGGTGCTTCCGAGGTAGCTCCTACCCTGTGTGTGTCCAAGGTGGTAAAGG
 181 GTGGCTCCTCAGGCAAGGGCACCACCCTCAGAGGCCGATCTGACGCTGACCTGGTTGTCT
 241 TCCTCAGTCCTCTCACCACTTTTCAGGATCAGTTAAATCGCCGGGGAGAGTTCATCCAGG
 301 AAATTAGGAGACAGCTGGAAGCCTGTCAAAGAGAGAGAGCATTTTCCGTGAAGTTTGAGG
 361 TCCAGGCTCCACGCTGGGGCAACCCCCGTGCGCTCAGCTTCGTACTGAGTTCGCTCCAGC
 421 TCGGGGAGGGGGTGGAGTTCGATGTGCTGCCTGCCTTTGATGCCCTGGGTCAGTTGACTG
 481 GCGGCTATAAACCTAACCCCCAAATCTATGTCAAGCTCATCGAGGAGTGCACCGACCTGC
 541 AGAAAGAGGGCGAGTTCTCCACCTGCTTCACAGAACTACAGAGAGACTTCCTGAAGCAGC
 601 GCCCCACCAAGCTCAAGAGCCTCATCCGCCTAGTCAAGCACTGGTACCAAAATTGTAAGA
 661 AGAAGCTTGGGAAGCTGCCACCTCAGTATGCCCTGGAGCTCCTGACGGTCTATGCTTGGG
 721 AGCGAGGGAGCATGAAAACACATTTCAACACAGCCCAGGGATTTCGGACGGTCTTGGAAT
 781 TAGTCATAAACTACCAGCAACTCTGCATCTACTGGACAAAGTATTATGACTTTAAAAACC
 841 CCATTATTGAAAAGTACCTGAGAAGGCAGCTCACGAAACCCAGGCCTGTGATCCTGGACC
 901 CGGCGGACCCTACAGGAAACTTGGGTGGTGGAGACCCAAAGGGTTGGAGGCAGCTGGCAC
 961 AAGAGGCTGAGGCCTGGCTGAATTACCCATGCTTTAAGAATTGGGATGGGTCCCCAGTGA
1021 GCTCCTGGATTCTGCTGTGATCTGGATCC
```

SEQUENCE: 4

```
   1 CCATGGGCCATCATCATCATCATCATCATCATCATCACAGCAGCGGCCATATCGAAGGTC
  61 GTCATATGATGGATCTCAGAAATACCCCAGCCAAATCTCTGGACAAGTTCATTGAAGACT
 121 ATCTCTTGCCAGACACGTGTTTCCGCATGCAAATCAACCATGCCATTGACATCATCTGTG
 181 GGTTCCTGAAGGAAAGGTGCTTCCGAGGTAGCTCCTACCCTGTGTGTGTCCAAGGTGG
 241 TAAAGGGTGGCTCCTCAGGCAAGGGCACCACCCTCAGAGGCCGATCTGCCGCTGCGCTGG
 301 TTGTCTTCCTCAGTCCTCTCACCACTTTTCAGGATCAGTTAAATCGCCGGGGAGAGTTCA
 361 TCCAGGAAATTAGGAGACAGCTGGAAGCCTGTCAAAGAGAGAGAGCATTTTCCGTGAAGT
 421 TTGAGGTCCAGGCTCCACGCTGGGGCAACCCCCGTGCGCTCAGCTTCGTACTGAGTTCGC
 481 TCCAGCTCGGGGAGGGGGTGGAGTTCGATGTGCTGCCTGCCTTTGATGCCCTGGGTCAGT
 541 TGACTGGCGGCTATAAACCTAACCCCCAAATCTATGTCAAGCTCATCGAGGAGTGCACCG
 601 ACCTGCAGAAAGAGGGCGAGTTCTCCACCTGCTTCACAGAACTACAGAGAGACTTCCTGA
```

FIGURE 7 cont.

```
 661  AGCAGCGCCCCACCAAGCTCAAGAGCCTCATCCGCCTAGTCAAGCACTGGTACCAAAATT
 721  GTAAGAAGAAGCTTGGGAAGCTGCCACCTCAGTATGCCCTGGAGCTCCTGACGGTCTATG
 781  CTTGGGAGCGAGGGAGCATGAAAACACATTTCAACACAGCCCAGGGATTTCGGACGGTCT
 841  TGGAATTAGTCATAAACTACCAGCAACTCTGCATCTACTGGACAAAGTATTATGACTTTA
 901  AAAACCCCATTATTGAAAAGTACCTGAGAAGGCAGCTCACGAAACCCAGGCCTGTGATCC
 961  TGGACCCGGCGGACCCTACAGGAAACTTGGGTGGTGGAGACCCAAAGGGTTGGAGGCAGC
1021  TGGCACAAGAGGCTGAGGCCTGGCTGAATTACCCATGCTTTAAGAATTGGGATGGGTCCC
1081  CAGTGAGCTCCTGGATTCTGCTGTGATCTGGATCC
```

OLIGOADENYLATE SYNTHETASE (OAS)

CROSS REFERENCE TO RELATED APPLICATIONS

This application is a divisional of U.S. application Ser. No. 13/364,140, filed Feb. 1, 2012, which is a continuation of U.S. application Ser. No. 12/750,545, filed Mar. 30, 2010, now U.S. Pat. No. 8,133,710, which is a divisional of U.S. application Ser. No. 11/601,440, filed on Nov. 17, 2006, titled "OLIGOADENYLATE SYNTHETASE (OAS)", now U.S. Pat. No. 7,732,177, which claims the benefit of U.S. Provisional Applications Nos. 60/739,159, filed Nov. 23, 2005, and 60/752,668, filed Dec. 21, 2005, all of which are incorporated herein by reference in their entirety.

BACKGROUND OF THE INVENTION

1. Field of the Invention

The present invention relates to novel pharmaceutical compositions for the treatment of virus infections and cancer in mammals.

2. Description of the Related Art

Oligoadenylate synthetase (OAS) proteins are interferon-induced proteins characterized by their capacity to catalyze the synthesis of 2-prime, 5-prime oligomers of adenosine (2-5As). Hovanessian et al., *EMBO* 6:1273-1280 (1987) found that interferon-treated human cells contain several OASs corresponding to proteins of 40 (OAS1), 46 (OAS1), 69 (OAS2), and 100 (OAS3) kD. Marie et al., *Biochem. Biophys. Res. Commun.* 160:580-587 (1989) generated highly specific polyclonal antibodies against p69, the 69-kD OAS2. By screening an interferon-treated human cell expression library with the anti-p69 antibodies, Marie and Hovanessian, *J. Biol. Chem.* 267:9933-9939 (1992) isolated a partial OAS2 cDNA. They screened additional libraries with the partial cDNA and recovered cDNAs encoding two OAS2 isoforms. The smaller isoform is encoded by two mRNAs that differ in the length of the 3-prime untranslated region.

Northern blot analysis revealed that OAS2 is expressed as four interferon-induced mRNAs in human cells. The predicted OAS2 proteins have a common 683-amino acid sequence and different 3-prime termini. According to SDS-PAGE of in vitro transcription/translation products, two isoforms have molecular masses of 69 and 71 kD. Both isoforms exhibited OAS activity in vitro. Sequence analysis indicated that OAS2 contains two OAS1-homologous domains separated by a proline-rich putative linker region. The N- and C-terminal domains are 41% and 53% identical to OAS1, respectively. Likewise, OAS3 contains three tandem units of the OAS 1-homologous domains.

By fluorescence in situ hybridization and by inclusion within mapped clones, Hovanian et al., *Genomics* 52:267-277 (1998) determined that the OAS1, OAS2, and OAS3 genes are clustered with a 130-kb region on 12q24.2. 2-5As bind to and activate RNase I, which degrades viral and cellular RNAs, leading to inhibition of cellular protein synthesis and impairment of viral replication.

A fourth human OAS gene, referred to as OASL, differs from OAS1, OAS2 and OAS3 in that OASL lacks enzyme activity. The OASL gene encodes a two-domain protein composed of an OAS unit fused to a 164 amino acid C-terminal domain that is homologous to a tandem repeat of ubiquitin. (Eskildsen et al., Nuc. Acids Res. 31:3166-3173, 2003; Kakuta et al., J. Interferon & Cytokine Res. 22:981-993, 2002.)

The present invention fulfills needs in the art by providing engineering and modification of oligoadenylate synthetase proteins to improve their drug properties.

BRIEF SUMMARY OF THE INVENTION

The present invention relates to novel pharmaceutical compositions composed of engineered forms of the oligoadenylate synthetases. These pharmaceutical compositions include mutant forms designed to have enhanced cell permeability, reduced oxidative potential, enhanced antiviral activity, enhanced enzymatic activity, or absent enzymatic activity. These pharmaceutical compositions further embody oligoadenylate synthetases chemically modified with polyethylene glycol. The present invention further relates to any possible combination of mutant forms or chemical modifications in a single polypeptide.

The present invention relates to mutant oligoadenylate synthetase forms that have no enzymatic activity, but that retain their antiviral activity, described as Class I modifications in FIG. 1. These forms have one or two mutations of aspartic acid to alanine in the magnesium binding site of the polypeptide, rendering the resulting OAS forms enzymatically inactive as shown in FIG. 2. These Class I enzymatically inactive OAS polypeptides retain antiviral activity, demonstrated using an encephalomyocarditis virus replication assay, as shown in FIG. 3.

The present invention further relates to mutant oligoadenylate synthetase forms that have reduced oxidative potential, described as Class II in FIG. 1. These forms have one or more cysteine amino acid residues deleted or replaced with an alternative residue of the form: alanine, serine, threonine, methionine, or glycine. Deletion or modification of these residues reduces the oxidative potential of the resulting polypeptide drug product, thereby improving manufacturability and in vivo serum stability of the drug. Manufacturability is improved by obviating the need for a reducing environment during drug manufacture while reducing the propensity of drug aggregation during manufacture, transport, and drug delivery. Class II modifications also improve stability of the drug in excipients suitable for use in man.

The present invention further relates to mutant oligoadenylate synthetase forms that have enhanced cell permeability, described as Class III in FIG. 1. Cell permeability is enhanced by the addition of basic amino acids, histidine, arginine, and lysine, to the amino terminus of the polypeptide. Addition of basic or positively-charged amino acids increases cell permeability through an absorptive endocytic process, thereby increasing the antiviral activity of the pharmaceutical compositions (compare FIG. 3 with FIG. 4). Enhancement of absorptive endocytosis of the polypeptide drug through the addition of basic amino acids results in the significant accumulation of active drug in intracellular, detergent insoluble stores (FIG. 5) thereby enhancing in vivo therapeutic effect.

The present invention further relates to chemical modifications of the polypeptide drug to contain a polyethylene glycol moiety, described as Class IV in FIG. 1. Chemical modification of cysteine residues results in retention of full enzyme activity (as shown in FIG. 6), improved in vitro bulk drug product stability, enhanced serum elimination half life, reduced in vivo drug immunogenicity, and reduced in vivo proteolytic cleavage of the drug polypeptide.

The present invention further relates to additional mutant oligoadenylate synthetase forms having significant anti-viral or anti-cancer activity, described as Class V in FIG. 1. Class V polypeptides are additional mutant OAS forms resulting from a mixture of developmental and optimizing considerations including one or more of: manufacturing tests in *E. coli*, recombinant vector development, and comparison with other identified forms of OAS proteins.

The present invention further relates to any combination of one or more of the mutations or modifications of FIG. 1 within a single polypeptide or pharmaceutical composition.

The present invention relates to the use of one or more of the modified polypeptides of FIG. 1 to treat or prevention virus infection or cancer in a mammal. The present invention further relates to the use of one or more of the polypeptides of FIG. 1 or any combination of the modifications of FIG. 1 to enhance cellular growth in a tissue, such as for example, a lung or liver. The present invention further relates to the use of any combination of one or more of the mutations or modifications of FIG. 1 within a single polypeptide or pharmaceutical composition for the prevention or treatment of virus infection or cancer in a mammal or to promote cellular or tissue growth or proliferation in a mammal.

In one embodiment the invention provides for a gene encoding the modified polypeptides of FIG. 1. In a still further embodiment, the gene can be used to manufacture a drug product using recombinant DNA technologies. In a still further embodiment, expression of the polypeptide can be effected in mammalian, insect, plant, bacterial, or fungal cells.

In a still further embodiment, the invention provides a therapeutic compound for preventing or inhibiting infection by a virus, preferably a flavivirus, most preferably hepatitis C virus, wherein the therapeutic compound is a polypeptide of FIG. 1. In other embodiments the therapeutic compound is a polynucleotide, such as DNA or RNA, encoding the polypeptide. In other embodiments the therapeutic compound is a combination of the polypeptides of FIG. 1, or a combination of one or more of the mutations or modifications described in FIG. 1 within a single polypeptide molecule.

In a still further embodiment, the invention provides a therapeutic compound for preventing or treating cancer, preferably prostate cancer, wherein the therapeutic compound is a polypeptide of FIG. 1. In other embodiments the therapeutic compound is a polynucleotide, such as DNA or RNA, encoding the polypeptide.

In further embodiments, compositions are provided that comprise one or more of the polypeptides of FIG. 1 in a pharmaceutically acceptable carrier.

The invention provides for the use of the polypeptides of the invention to prepare a medicament for preventing or inhibiting hepatitis C or respiratory syncytial virus infection.

The invention still further relates to a method of preventing or curing infection by a flavivirus or any other virus in a human subject susceptible to the infection by administering one of the polypeptides of FIG. 1. Other embodiments involve the treatment of any mammal.

The invention embodies also treatments for infection with the human immunodeficiency virus (HIV).

The invention still further relates to a method of treating cancer, such as prostate cancer or breast cancer by administration of polypeptides disclosed herein.

The invention still further relates to a method of promoting cellular or tissue growth by administration of the polypeptides disclosed herein or polynucleotides, such as DNA or RNA, encoding a polypeptide of the invention.

The invention still further relates to a method of reducing inflammation by administration of the polypeptides disclosed herein or polynucleotides, such as DNA or RNA, encoding a polypeptide of the invention.

The invention still further relates to a method of promoting immune suppression by administration of the polypeptides disclosed herein or polynucleotides, such as DNA or RNA, encoding a polypeptide of the invention.

Also provided is the use of any of the polypeptides of FIG. 1 as a component of a therapeutic composition.

In a further embodiment, a nucleic acid encoding the polypeptides of FIG. 1 can be administered in the form of gene therapy.

The invention provides for any method of preparing the polypeptides of FIG. 1 or the genes encoding said polypeptides, including the use any recombinant DNA methodologies.

The invention provides for the use of site directed mutagenesis, polymerase chain reaction, or nucleic acid chemical synthesis to prepare the polypeptides of FIG. 1 or their encoding genes.

The invention provides for methods of chemically cross-linking polyethylene glycol to the polypeptides of the present invention. In one embodiment, chemical cross-linking targets the reactive sulfhydryl species of the cysteine residues. In a still further embodiment, cross-linking targets a single solvent-exposed cysteine residue of the polypeptides of the invention. In a still further embodiment, chemical cross-linking of polyethylene glycol is mediated through the amino-terminal primary or secondary amines of the polypeptide. In a still further embodiment, chemical cross-linking of polyethylene glycol is mediated through any carboxyl group of the polypeptide. In a still further embodiment, cross-linking is achieved by conjugation of polyethylene glycol to any lysine or arginine amino acid residue of the polypeptide. In a still further embodiment, multiple sites of polyethylene glycol conjugation can be achieved.

The invention provides for forms of the polypeptides of FIG. 1 that are derivatized with polyethylene glycol for use in a therapeutic product.

The invention provides for forms of the polypeptides of FIG. 1 that are derivatized with polyethylene glycol for use in treating virus infection or cancer.

The invention provides for forms of the polypeptides of FIG. 1 that are derivatized with polyethylene glycol for promoting cellular or tissue growth.

The invention provides for administering forms of the polypeptides of FIG. 1 that are derivatized with polyethylene glycol to a mammal.

The invention provides for forms of the polypeptides of FIG. 1 that are derivatized with polyethylene glycol for use in treating inflammation.

The invention provides for forms of the polypeptides of FIG. 1 that are derivatized with polyethylene glycol for use in promoting suppression of the immune system of a mammal.

The invention provides for methods of chemically cross-linking polyethylene glycol to the polypeptides of the present invention, most particularly those described as Class IV in FIG. 1, whereby cross-linking is achieved using a maleimide, ortho-pyridyldisulfide, vinylsulfone, or thiol functional group. In a further embodiment, single chain, multiple chain, multi-arm, branched, or forked polyethylene glycols of any molecular weight may be used. In a still further embodiment, polyethylene glycols may contain radioactive or fluorescent moieties.

The invention provides for methods of chemically cross-linking polyethylene glycol to the polypeptides of the present invention using succinimidyl alpha-methylbutanoate, succinimidyl propionate, N-hydroxysuccinimide, ester, aldehyde, ortho-pyridylthioester, or amine functional groups.

The invention provides for increasing the cell permeability of a drug by conjugation to the polypeptides of the invention. The invention further provides for increasing the cell permeability of a drug by conjugation to five or more consecutive amino acids of the polypeptides of the invention.

The invention provides a method for delivering a drug into a cell by conjugation to the polypeptides of the present invention or five or more consecutive amino acids of the polypeptides of the present invention. In a further embodiment, conjugation may be affected using chemical methods and may be through covalent or non-covalent interaction. In a still further embodiment, nucleic acids encoding the polypeptides of the present invention may be joined with other nucleic acids in order to make heterologous polypeptides with increased cell permeability, said increased permeability being derived from five or more amino acids of the polypeptides of the present invention.

BRIEF DESCRIPTION OF THE FIGURES

FIG. 1 is a Table describing the polypeptides of the present invention and their defining mutations or modifications relative to a reference amino acid sequence.

FIG. 7 shows the polynucleotide sequences of SEQUENCE 2 (SEQ ID NO:2); SEQUENCE 3 (SEQ ID NO:3); and SEQUENCE 4 (SEQ ID NO:4).

DETAILED DESCRIPTION OF THE INVENTION

Introduction and Definitions

Figure 2:
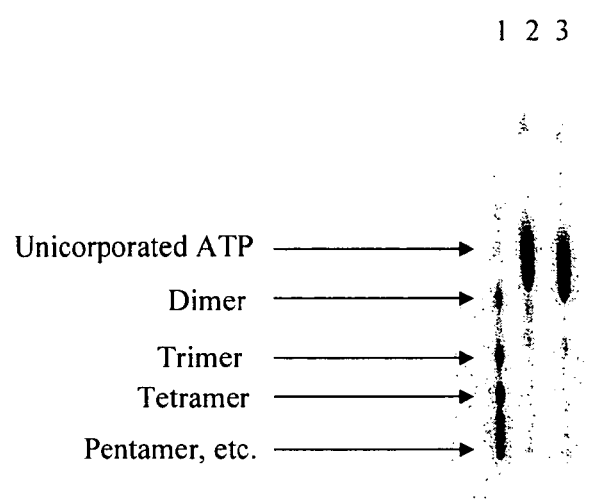
FIG. 2 is a comparison of oligoadenylate synthetase activity of a Class I-Class III combination mutant polypeptide (the result of cloning SEQUENCE:4 (SEQ ID NO:4) of FIG. 7 into the NcoI and BamHI sites of the pET9d vector, followed by transformation into the Rosetta DE3 bacterial host and expression and purification according to the invention) versus a reference Class III polypeptide variant (the result of cloning SEQUENCE:2 (SEQ ID NO:2) of FIG. 7 into the NcoI and BamHI sites of the pET9d vector, followed by transformation into the Rosetta DE3 bacterial host and expression and purification according to the invention). Lane 1: 50 ng of the reference Class III variant. Lane 2: 1 μg of a Class I-Class III Variant. Lane 3: blank reaction containing no protein. Oligoadenylate synthetase activity is measured according to a standard reaction involving the incorporation of $^{32}$P-labeled adenosine triphosphate into 2'-5' oligoadenylate species that migrate more rapidly on polyethylenimine treated thin layer chromatography plates as described in the specification.

We have demonstrated that mutations in the OAS genes confer resistance to virus infection. (U.S. Patent Application Ser. Nos. 60/513,888, filed Oct. 23, 2003; 60/542,373, filed Feb. 6, 2004; 60/554,758, filed Mar. 19, 2004; 60/560,524, filed Apr. 8, 2004; 60/578,323, filed Jun. 8, 2004; 60/605,243, filed Aug. 26, 2004; Ser. No. 10/972,135, filed Oct. 22, 2004; 60/677,680, filed May 4, 2005; and 60/710,704, filed Aug. 23, 2004, all of which are incorporated by reference herein.) Several novel forms of the OAS 1, OAS2, and OAS3 genes have been cloned by us, and we have developed pharmaceutical compositions derived from these and other novel oligoadenylate synthetase forms. We have demonstrated that these pharmaceutical compositions are antiviral in vitro and cause growth arrest in cancer cell lines.

We have further demonstrated that these pharmaceutical compositions promote cellular growth in certain cell lines. We have further demonstrated that these pharmaceutical compositions have a mitogenic effect. We have further demonstrated that these pharmaceutical compositions have the ability to enter a cell and remain enzymatically active in intracellular stores for several days or more. We have further demonstrated that the cell-penetrating property of the pharmaceutical compositions can be enhanced through the addition of basic amino acid residues including arginine, lysine, and histidine (described as Class III in FIG. 1).

We have further demonstrated that these pharmaceutical compositions have broad antiviral activity. We have further demonstrated that these pharmaceutical compositions can be derivatized with polyethylene glycol and retain their enzymatic activity. We show that the stability of the pharmaceutical compositions is dependent on the presence of reducing agents and we propose several modifications to provide more oxidation resistant forms of the protein.

We demonstrate that bulk quantities of the pharmaceutical compositions can be manufactured using recombinant DNA technologies by expression in *Escherichia coli*. We further demonstrate that these manufactured pharmaceutical compositions can be administered to mammals and produce no observable toxic effects. We further demonstrate that these manufactured pharmaceutical compositions have good biodistribution and pharmacokinetic properties when administered to a mammal by injection.

The present invention describes mutant or modified oligoadenylate synthetase polypeptides that efficiently enter mammalian cells and enhance the performance of the OAS-RNAse L pathway. These novel polypeptide compositions are antiviral in in vitro cell culture models. They also cause certain transformed cell lines to undergo growth arrest and promote cellular growth in other cell lines. The polypeptides of the present invention comprise five classes of modified oligoadenylate synthetase proteins, including: Class I, enzymatically inactive antiviral forms; Class II, oxidation resistant forms; Class III, enhanced cell permeable forms; Class IV, polyethylene glycol conjugated forms; and Class V, mixed developmental and optimization forms. The invention relates to the manufacture and use of the polypeptides for the treatment of virus infection, inflammation, and neoplastic disease and to promote cellular growth and regeneration in mammals.

In reference to the detailed description, the following definitions are used:

A: adenine; C: cytosine; G: guanine; T: thymine (in DNA); and U: uracil (in RNA)

Allele: A variant of DNA sequence of a specific gene. In diploid cells a maximum of two alleles will be present, each in the same relative position or locus on homologous chromosomes of the chromosome set. When alleles at any one locus are identical the individual is said to be homozygous for that locus, and when they differ the individual is said to be heterozygous for that locus. Since different alleles of any one gene may vary by only a single base, the possible number of alleles for any one gene is very large. When alleles differ, one is often dominant to the other, which is said to be recessive. Dominance is a property of the phenotype and does not imply inactivation of the recessive allele by the dominant. In numerous examples the normally functioning (wild-type) allele is dominant to all mutant alleles of more or less defective function. In such cases the general explanation is that one functional allele out of two is sufficient to produce enough active gene product to support normal development of the organism (i.e., there is normally a two-fold safety margin in quantity of gene product).

Haplotype: One of many possible pluralities of Alleles, serially ordered by chromosomal localization and representing that set of Alleles carried by one particular homologous chromosome of the chromosome set.

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Base Pair (bp): A partnership of adenine (A) with thymine (T), or of cytosine (C) with guanine (G) in a double stranded DNA molecule. In RNA, uracil (U) is substituted for thymine. When referring to RNA herein, the symbol T may be used interchangeably with U to represent uracil at a particular position in the RNA molecule.

Nucleic Acid: A polymer of nucleotides, either single or double stranded.

Polynucleotide: A polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

Gene: A nucleic acid whose nucleotide sequence codes for an RNA or polypeptide. A gene can be either RNA or DNA.

Duplex DNA: A double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Complementary Bases Nucleotides that normally pair up when DNA or RNA adopts a double stranded configuration.

Complementary Nucleotide Sequence: A sequence of nucleotides in a single-stranded molecule of DNA or RNA that is sufficiently complementary to that on another single strand to specifically hybridize to it with consequent hydrogen bonding.

Conserved: A nucleotide sequence is conserved with respect to a preselected (reference) sequence if it non-randomly hybridizes to an exact complement of the preselected sequence.

Hybridization: The pairing of substantially complementary nucleotide sequences (strands of nucleic acid) to form a duplex or heteroduplex by the establishment of hydrogen bonds between complementary base pairs. It is a specific, i.e. non-random, interaction between two complementary polynucleotides that can be competitively inhibited.

Nucleotide Analog: A purine or pyrimidine nucleotide that differs structurally from A, T, G, C, or U, but is sufficiently similar to substitute for the normal nucleotide in a nucleic acid molecule.

DNA Homolog: A nucleic acid having a preselected conserved nucleotide sequence and a sequence coding for a receptor capable of binding a preselected ligand.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Stop Codon: Any of three codons that do not code for an amino acid, but instead cause termination of protein synthesis. They are UAG, UAA and UGA and are also referred to as a nonsense or termination codon.

Reading Frame Particular sequence of contiguous nucleotide triplets (codons) employed in translation. The reading frame depends on the location of the translation initiation codon.

Intron: Also referred to as an intervening sequence, a noncoding sequence of DNA that is initially copied into RNA but is cut out of the final RNA transcript.

Protein or polypeptide: The term "protein" or "polypeptide" refers to a polymer of amino acids and does not refer to a specific length of the product. Peptides, oligopeptides, polypeptides, proteins, and polyproteins, as well as fragments of these, are included within this definition. The term may include post expression modifications of the protein, for example, glycosylations, acetylations, phosphorylations and the like. Included within the definition are, for example, proteins containing one or more analogs of an amino acid (including, for example, unnatural amino acids, etc.), proteins with substituted linkages, as well as other modifications known in the art, both naturally occurring and non-naturally occurring.

Unless otherwise indicated, the position numbering of amino acid residues recited herein is relative to the amino acid sequence SEQUENCE:1 (SEQ ID NO:1) of FIG. 1.

A "variant" is a polypeptide comprising a sequence which differs in one or more amino acid position(s) from that of a parent polypeptide sequence.

The term "parent polypeptide" is intended to indicate the polypeptide sequence to be modified in accordance with the present invention.

A "fragment" or "subsequence" is any portion of an entire sequence, up to but not including the entire sequence. Thus, a fragment or subsequence refers to a sequence of amino acids or nucleic acids that comprises a part of a longer sequence of amino acids (e.g., polypeptide) or nucleic acids (e.g., polynucleotide).

A polypeptide, nucleic acid, or other component is "isolated" when it is partially or completely separated from components with which it is normally associated (other peptides, polypeptides, proteins (including complexes, e.g., polymerases and ribosomes which may accompany a native sequence), nucleic acids, cells, synthetic reagents, cellular contaminants, cellular components, etc.), e.g., such as from other components with which it is normally associated in the cell from which it was originally derived. A polypeptide, nucleic acid, or other component is isolated when it is partially or completely recovered or separated from other components of its natural environment such that it is the predominant species present in a composition, mixture, or collection of components (i.e. on a molar basis it is more abundant than any other individual species in the composition). In some instances, the preparation consists of more than about 60%, 70% or 75%, typically more than about 80%, or preferably more than about 90% of the isolated species.

A "substantially pure" or "isolated" nucleic acid (e.g., RNA or DNA), polypeptide, protein, or composition also means where the object species (e.g., nucleic acid or polypeptide) comprises at least about 50, 60, or 70 percent by weight (on a molar basis) of all macromolecular species present. A substantially pure or isolated composition can also comprise at least about 80, 90, or 95 percent by weight of all macromolecular species present in the composition. An isolated object species can also be purified to essential homogeneity (contaminant species cannot be detected in the composition by conventional detection methods) wherein the composition consists essentially of derivatives of a single macromolecular species. The term "purified" generally denotes that a nucleic acid, polypeptide, or protein gives rise to essentially one band in an electrophoretic gel. It typically means that the nucleic acid, polypeptide, or protein is at least about 50% pure, 60% pure, 70% pure, 75% pure, more preferably at least about 85% pure, and most preferably at least about 99% pure.

The term "isolated nucleic acid" may refer to a nucleic acid (e.g., DNA or RNA) that is not immediately contiguous with both of the coding sequences with which it is immediately contiguous (i.e., one at the 5' and one at the 3' end) in the naturally occurring genome of the organism from which the nucleic acid of the invention is derived. Thus, this term includes, e.g., a cDNA or a genomic DNA fragment produced by polymerase chain reaction (PCR) or restriction endonuclease treatment, whether such cDNA or genomic DNA fragment is incorporated into a vector, integrated into the genome of the same or a different species than the organism, including, e.g., a virus, from which it was originally derived, linked to an additional coding sequence to form a hybrid gene encoding a chimeric polypeptide, or independent of any other DNA sequences. The DNA may be double-stranded or single-stranded, sense or antisense.

A "recombinant polynucleotide" or a "recombinant polypeptide" is a non-naturally occurring polynucleotide or polypeptide which may include nucleic acid or amino acid sequences, respectively, from more than one source nucleic acid or polypeptide, which source nucleic acid or polypeptide can be a naturally occurring nucleic acid or polypeptide, or can itself have been subjected to mutagenesis or other type of modification. A nucleic acid or polypeptide may be deemed "recombinant" when it is synthetic or artificial or engineered, or derived from a synthetic or artificial or engineered polypeptide or nucleic acid. A recombinant nucleic acid (e.g., DNA or RNA) can be made by the combination (e.g., artificial combination) of at least two segments of sequence that are not typically included together, not typically associated with one another, or are otherwise typically separated from one another. A recombinant nucleic acid can comprise a nucleic acid molecule formed by the joining together or combination of nucleic acid segments from different sources and/or artificially synthesized. A "recombinant polypeptide" often refers to a polypeptide that results from a cloned or recombinant nucleic acid. The source polynucleotides or polypeptides from which the different nucleic acid or amino acid sequences are derived are sometimes homologous (i.e., have, or encode a polypeptide that encodes, the same or a similar structure and/or function), and are often from different isolates, serotypes, strains, species, of organism or from different disease states, for example.

The term "recombinant" when used with reference, e.g., to a cell, polynucleotide, vector, protein, or polypeptide typically indicates that the cell, polynucleotide, or vector has been modified by the introduction of a heterologous (or foreign) nucleic acid or the alteration of a native nucleic acid, or that the protein or polypeptide has been modified by the introduction of a heterologous amino acid, or that the cell is derived from a cell so modified. Recombinant cells express nucleic acid sequences that are not found in the native (non-recombinant) form of the cell or express native nucleic acid sequences that would otherwise be abnormally expressed, under-expressed, or not expressed at all. The term "recombinant" when used with reference to a cell indicates that the cell replicates a heterologous nucleic acid, or expresses a polypeptide encoded by a heterologous nucleic acid. Recombinant cells can contain coding sequences that are not found within the native (non-recombinant) form of the cell. Recombinant cells can also contain coding sequences found in the native form of the cell wherein the coding sequences are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, recombination, and related techniques.

The term "recombinantly produced" refers to an artificial combination usually accomplished by either chemical synthesis means, recursive sequence recombination of nucleic acid segments or other diversity generation methods (such as, e.g., shuffling) of nucleotides, or manipulation of isolated segments of nucleic acids, e.g., by genetic engineering techniques known to those of ordinary skill in the art. "Recombinantly expressed" typically refers to techniques for the production of a recombinant nucleic acid in vitro and transfer of the recombinant nucleic acid into cells in vivo, in vitro, or ex vivo where it may be expressed or propagated.

An "immunogen" refers to a substance capable of provoking an immune response, and includes, e.g., antigens, autoantigens that play a role in induction of autoimmune diseases, and tumor-associated antigens expressed on cancer cells. An immune response generally refers to the development of a cellular or antibody-mediated response to an agent, such as an antigen or fragment thereof or nucleic acid encoding such agent. In some instances, such a response comprises a production of at least one or a combination of CTLs, B cells, or various classes of T cells that are directed specifically to antigen-presenting cells expressing the antigen of interest.

An "antigen" refers to a substance that is capable of eliciting the formation of antibodies in a host or generating a specific population of lymphocytes reactive with that substance. Antigens are typically macromolecules (e.g., proteins and polysaccharides) that are foreign to the host.

An "adjuvant" refers to a substance that enhances an antigen's immune-stimulating properties or the pharmacological effect(s) of a drug. An adjuvant may non-specifically enhance the immune response to an antigen. "Freund's Complete Adjuvant," for example, is an emulsion of oil and water containing an immunogen, an emulsifying agent and mycobacteria. Another example, "Freund's incomplete adjuvant," is the same, but without mycobacteria.

A "vector" is a component or composition for facilitating cell transduction or transfection by a selected nucleic acid, or expression of the nucleic acid in the cell. Vectors include, e.g., plasmids, cosmids, viruses, YACs, bacteria, poly-lysine, etc. An "expression vector" is a nucleic acid construct or sequence, generated recombinantly or synthetically, with a series of specific nucleic acid elements that permit transcription of a particular nucleic acid in a host cell. The expression vector can be part of a plasmid, virus, or nucleic acid fragment. The expression vector typically includes a nucleic acid to be transcribed operably linked to a promoter. The nucleic acid to be transcribed is typically under the direction or control of the promoter.

The term "subject" as used herein includes, but is not limited to, an organism; a mammal, including, e.g., a human, non-human primate (e.g., baboon, orangutan, monkey), mouse, pig, cow, goat, cat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

The term "pharmaceutical composition" means a composition suitable for pharmaceutical use in a subject, including an animal or human. A pharmaceutical composition generally comprises an effective amount of an active agent and a carrier, including, e.g., a pharmaceutically acceptable carrier.

The term "effective amount" means a dosage or amount sufficient to produce a desired result. The desired result may comprise an objective or subjective improvement in the recipient of the dosage or amount.

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such as a nucleic acid, vector, gene, polypeptide, protein, substance, or composition thereof that, when administered to a subject who does not display signs or symptoms of pathology, disease or disorder, or who displays only early signs or symptoms of pathology, disease, or disorder, diminishes, prevents, or decreases the risk of the subject developing a pathology, disease, or disorder. A "prophylactically useful" agent or compound (e.g., nucleic acid or polypeptide) refers to an agent or compound that is useful in diminishing, preventing, treating, or decreasing development of pathology, disease or disorder.

A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such as a nucleic acid, vector, gene, polypeptide, protein, substance, or composition thereof, that eliminates or diminishes signs or symptoms of pathology, disease or disorder, when administered to a subject suffering from such signs or symptoms. A "therapeutically useful" agent or compound (e.g., nucleic acid or polypeptide) indicates that an agent or compound is useful in diminishing, treating, or eliminating such signs or symptoms of a pathology, disease or disorder.

Modes of Practicing the Invention

2',5'-oligoadenylate synthetases (OAS) are a family of IFN-α-inducible, RNA dependent effector enzymes that synthesize short 2' to 5' linked oligoadenylate (2-5A) molecules from ATP. 2-5A molecules bind to and activate the RNAseL enzyme, which once activated, degrades viral and cellular RNAs and blocks cellular protein synthesis. OAS enzymes constitute an important part of the nonspecific immune defense against viral infections and have been used as a cellular marker for viral infection. In addition to the role in hepatitis C infection discussed herein, OAS activity is implicated in other disease states, particularly those in which a viral infection plays a role.

While specific pathogenic mechanisms are subjects of current analysis, viral infections are believed to play a role in the development of diseases such as diabetes. Lymphocytic OAS activity is significantly elevated in patients with type 1 diabetes, suggesting that OAS may be an important link between viral infections and disease development. In a study involving diabetic twins from monozygotic twin pairs, Bonnevie-Nielsen et al. (Clin Immunol. 2000 July;96(1):11-8) showed that OAS is persistently activated in both recent-onset and long-standing type I diabetes. Continuously elevated OAS activity in type 1 diabetes is clearly different from a normal antiviral response and might indicate a chronic stimulation of the enzyme, a failure of down regulatory mechanisms, or an aberrant response to endogenous or exogenous viruses or their products.

A more direct link between a viral infection and the development of diabetes is exemplified by a number of studies showing that between 13 and 33% of patients with chronic hepatitis C have diabetes mellitus (type 2 diabetes), a level that is significantly increased compared with that in matched healthy controls or patients with chronic hepatitis B (Knobler et al. Am J. Gastroenterol. 2003 December; 98(12):2751-6). While OAS has not to date been reported to play a role in the development of diabetes mellitus following hepatitis C infection, it may be a useful marker for the antiviral response system. Furthermore, the results reported according to the present invention illustrate that if hepatitis C infection is causally related to diabetes mellitus, inhibition or abolition of hepatitis C infection using the compositions and methods disclosed herein may be advantageous in preventing or alleviating development of diabetes mellitus.

A further published study has shown that OAS plays an essential role in wound healing and its pathological disorders, particularly in the case of venous ulcers and diabetes-associated poorly-healing wounds (WO 02/090552). In the case of poor wound healing, OAS mRNA levels in the affected tissues were reduced, rather than elevated as in lymphocytes derived from patients suffering from type I diabetes. These findings point to OAS as an etiologically important marker of immune reactions in diabetes and diabetes-related wound healing.

OAS may also play an intermediary role in cell processes involved in prostate cancer. A primary biochemical function of OAS is to promote the activity of RNaseL, a uniquely-regulated endoribonuclease that is enzymatically stimulated by 2-5A molecules. RNaseL has a well-established role in mediating the antiviral effects of IFN, and is a strong candidate for the hereditary prostate cancer 1 allele (HPC1). Mutations in RNaseL have been shown to predispose men to an increased incidence of prostate cancer, which in some cases reflect more aggressive disease and/or decreased age of onset compared with non RNase L-linked cases. Xiang et al. (Cancer Res. 2003 Oct. 15; 63(20):6795-801) demonstrated that biostable phosphorothiolate analogs of 2-5A induced RNaseL activity and caused apoptosis in cultures of late-stage metastatic human prostate cancer cell lines. Their findings suggest that the elevation of OAS activity with a concurrent increase in 2-5A levels may facilitate the destruction of cancer cells through a potent apoptotic pathway. Thus, use of compositions and methods disclosed herein may find utility in the detection, treatment and/or prevention of prostate cancer.

OAS may further play a role in normal cell growth regulation, either through its regulation of RNaseL or through another as yet undiscovered pathway. There is considerable evidence to support the importance of OAS in negatively regulating cell growth. Rysiecki et al. (J. Interferon Res. 1989 December; 9(6):649-57) demonstrated that stable transfection of human OAS into a glioblastoma cell line results in reduced cellular proliferation. OAS levels have also been shown to be measurable in several studies comparing quiescent versus proliferating cell lines (e.g. Hassel and Ts'O, Mol. Carcinog. 1992; 5(1):41-51 and Kimchi et al., Eur J. Biochem. 1981; 114(1):5-10) and in each case the OAS levels were greatest in quiescent cells. Other studies have shown a correlation between OAS level and cell cycle phase, with OAS levels rising sharply during late S phase and then dropping abruptly in G2 (Wells and Mallucci, Exp Cell Res. 1985 July; 159(1):27-36).

Several studies have shown a correlation between the induction of OAS and the onset of antiproliferative effects following stimulation with various forms of interferon (see Player and Torrence, Pharmacol Ther. 1998 May; 78(2):55-113). Induction of OAS has also been shown during cell differentiation (e.g., Salzberg et al., J Cell Sci. 1996 June; 109(Pt 6):1517-26 and Schwartz and Nilson, Mol Cell Biol. 1989 September; 9(9):3897-903). Other reports of induction of OAS by platelet derived growth factor (PDGF) (Zullo et al. Cell. 1985 December; 43(3 Pt 2):793-800) and under conditions of heat-shock induced growth (Chousterman et al., J Biol. Chem. 1987 Apr. 5; 262(10):4806-11) lead to the hypothesis that induction of OAS is a normal cell growth control mechanism. Thus, use of compositions and methods disclosed herein may find broad utility in the detection, treatment and/or prevention of cancer or in the promotion of cellular or tissue growth or tissue regeneration.

Therapeutic Agents for Restoring and/or Enhancing OAS Function

As described previously the polypeptides of the present invention may be advantageous in the treatment of virus infection or other indications including but not limited to cancer, diabetes mellitus, inflammation, tissue regeneration, and wound healing. The discussion below pertains to administration of any of the foregoing proteins or polypeptides.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture) of a polynucleotide sequence of the present invention. Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue (at position minus 1).

The polypeptides of the present invention also include the protein sequences defined in FIG. 1 and derivatives thereof including analogs and fragments that function similarly to the FIG. 1 forms. Thus, for example, one or more of the amino acid residues of the polypeptide may be replaced by conserved amino acid residues, as long as the function of the polypeptides is maintained.

The polypeptides may be employed in accordance with the present invention by expression of such polypeptides in vivo, which is often referred to as gene therapy. Thus, for example, cells may be transduced with a polynucleotide (DNA or RNA) encoding the polypeptides ex vivo, with those transduced cells then being provided to a patient to be treated with the polypeptide. Such methods are well known in the art. For example, cells may be transduced by procedures known in the art by use of a retroviral particle containing RNA encoding a polypeptide of the present invention.

Similarly, transduction of cells may be accomplished in vivo for expression of the polypeptide in vivo, for example, by procedures known in the art. As known in the art, a producer cell for producing a retroviral particle containing RNA encoding the polypeptides of the present invention may be administered to a patient for transduction in vivo and expression of the polypeptides in vivo.

These and other methods for administering the polypeptides of the present invention by such methods should be apparent to those skilled in the art from the teachings of the present invention. For example, the expression vehicle for transducing cells may be other than a retrovirus, for example, an adenovirus which may be used to transduce cells in vivo after combination with a suitable delivery vehicle.

Figure 4:
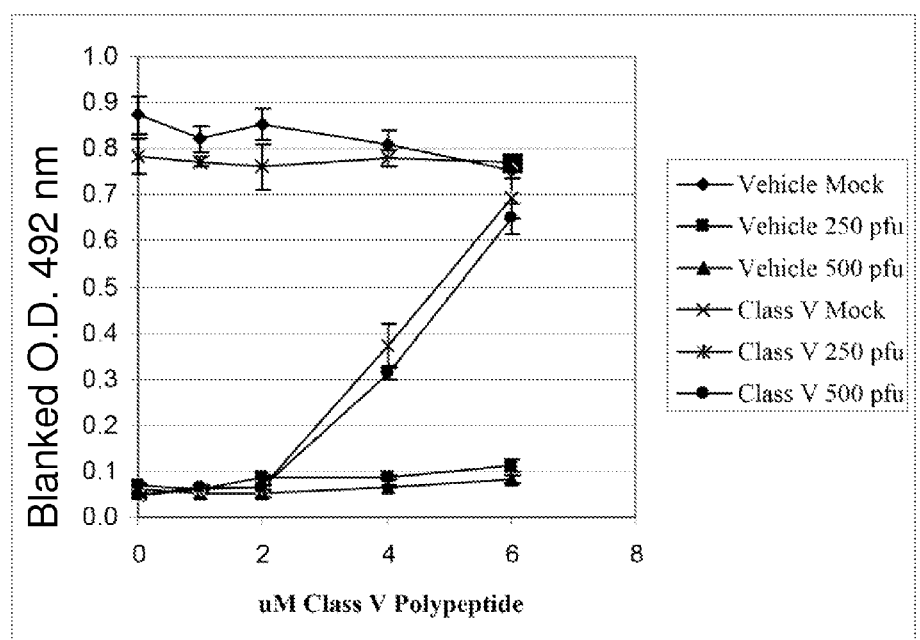
Figure 5:
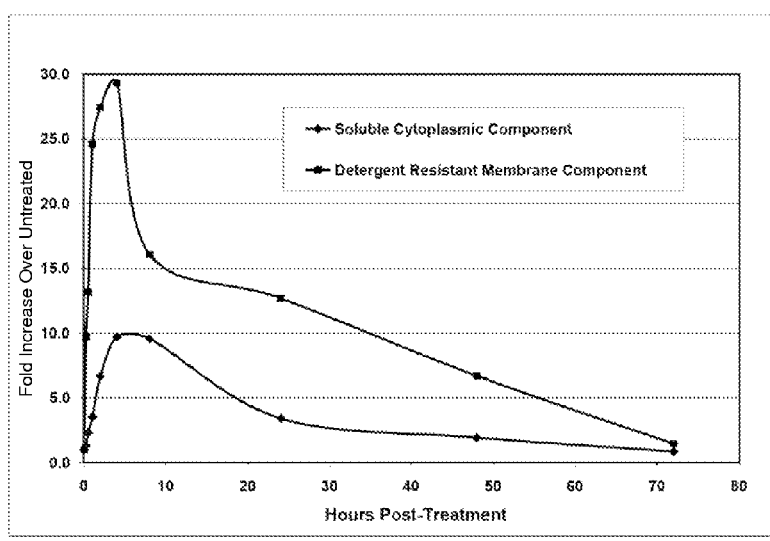

Furthermore, the polypeptides of the present invention are able, as part of their native function, to transduce across a cell membrane and mediate their antiviral effects in the absence of a delivery vector or expression vehicle. The mechanism of polypeptide transduction is likely absorptive endocytosis or lipid raft-mediated macropinocytosis, with significant amounts of the active polypeptide being present in the cytoplasm and in detergent insoluble membrane fractions of treated cells as demonstrated in FIG. 5. The essentially basic and positively charged character of the proteins likely mediates this unusual characteristic, making the polypeptides themselves effective pharmaceutical compositions without the need for carriers to increase cell permeability. The cell transduction properties of basic, positively charged proteins has been previously described and is well known to those skilled in the art (Ryser and Hancock, Science. 1965 Oct. 22; 150(695):501-3). It is clear from FIG. 2 and FIG. 3 of the present invention that the polypeptides of the invention can affect an antiviral function in cell culture that can only be mediated by transduction of the polypeptides into the cell. Class III modifications to the reference polypeptide increase their basic charge and therefore their cell permeability (compare FIG. 3 with FIG. 4).

In the case where the polypeptides are prepared as a liquid formulation and administered by injection, preferably the solution is an isotonic salt solution containing 140 millimolar sodium chloride and 10 millimolar calcium at pH 7.4. The injection may be administered, for example, in a therapeutically effective amount, preferably in a dose of about 1 µg/kg body weight to about 5 mg/kg body weight daily, taking into account the routes of administration, health of the patient, etc.

The polypeptide(s) of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The polypeptide(s) of the present invention can also be modified by chemically linking the polypeptide to one or more moieties or conjugates to enhance the activity, cellular distribution, or cellular uptake of the polypeptide(s). Such moieties or conjugates include lipids such as cholesterol, cholic acid, thioether, aliphatic chains, phospholipids and their derivatives, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773.

The polypeptide(s) of the present invention may also be modified to target specific cell types for a particular disease indication, including but not limited to liver cells in the case of hepatitis C infection. As can be appreciated by those skilled in the art, suitable methods have been described that achieve the described targeting goals and include, without limitation, liposomal targeting, receptor-mediated endocytosis, and antibody-antigen binding. In one embodiment, the asiaglycoprotein receptor may be used to target liver cells by the addition of a galactose moiety to the polypeptide(s). In another embodiment, mannose moieties may be conjugated to the polypeptide(s) in order to target the mannose receptor found on macrophages and liver cells. As one skilled in the art will recognize, multiple delivery and targeting methods may be combined. For example, the polypeptide(s) of the present invention may be targeted to liver cells by encapsulation within liposomes, such liposomes being conjugated to galactose for targeting to the asialoglycoprotein receptor.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed in conjunction with other therapeutic compounds.

When the polypeptide(s) of the present invention are used as a pharmaceutical, they can be given to mammals, in a suitable vehicle. When the polypeptides of the present invention are used as a pharmaceutical as described above, they are given, for example, in therapeutically effective doses of about 10 µg/kg body weight to about 10 mg/kg body weight daily, taking into account the routes of administration, health of the patient, etc. The amount given is preferably adequate to achieve prevention or inhibition of infection by a virus, preferably a flavivirus, most preferably RSV and HCV, prevention or treatment of cancer, inflammation, diabetes, or other diseases.

The proteins, their fragments or other derivatives, or analogs thereof, or cells expressing them can be used as an immunogen to produce antibodies thereto. These antibodies can be, for example, polyclonal, monoclonal, chimeric, single chain, Fab fragments, or the product of an Fab expression library. Various procedures known in the art may be used for the production of polyclonal antibodies.

Antibodies generated against the polypeptide(s) of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Moreover, a panel of such antibodies specific to a large number of polypeptides can be used.

For preparation of monoclonal antibodies, any technique which provides antibodies produced by continuous cell line cultures can be used. Examples include the hybridoma technique (Kohler and Milstein, 1975, *Nature*, 256:495-597), the trioma technique, the human B-cell hybridoma technique (Kozbor, et al., 1983, *Immunology Today* 4:72), and the EBV-hybridoma technique to produce human monoclonal antibodies (Coe, et al., 1985, *Monoclonal Antibodies and Cancer Therapy*, Alan R. Liss, Inc. pp. 77-96).

Techniques described for the production of single chain antibodies (U.S. Pat. No. 4,946,778) can be adapted to produce single chain antibodies to immunogenic polypeptide products of this invention.

The antibodies can be used in methods relating to the localization and activity of the protein sequences of the invention, e.g., for imaging these proteins, measuring levels thereof in appropriate physiological samples, and the like.

The invention provides for polypeptides that differ from the polypeptides of FIG. 1 by 1 to 34 amino acids, such differences may include substitutions, insertions, deletions, the incorporation of modified amino acids or amino acid derivatives, and the addition or deletion of amino acids from the C-terminus or N-terminus of the polypeptides. The invention provides for therapeutic and prophylactic uses of these polypeptides including but not limited to the treatment of virus infection, neoplasm, cancer, diabetes, and to promote cell growth and differentiation and tissue regeneration. The invention provides for polynucleotides encoding the polypeptides of the invention and uses thereof including but not limited to uses in manufacturing the polypeptides, as gene therapies, as diagnostic tools, etc.

The invention provides for the following classes of polypeptide:

Class I Polypeptide Modifications

The Class I modifications of the present invention represent enzymatically inactive oligoadenylate synthetase forms created by mutation of the magnesium binding site of the native protein. These enzymatically inactive polypeptides retain antiviral activity and constitute novel therapeutic compositions under the present invention. An example of the in vitro antiviral activity of a Class I modified polypeptide is demonstrated in FIG. 3. The polypeptides of the invention include all enzymatically inactive forms of the oligoadenylate synthetases, such forms being those that do not synthesize 2-prime-5-prime oligoadenylates, and uses thereof.

Class II Polypeptide Modifications

The Class II modifications of the present invention represent mutant oligoadenylate synthetase forms that have increased in vitro and in vivo stability by virtue of the removal of one or more highly-reactive, sulfhydryl-containing cysteine residues. Removal of one or more sulfhydryl groups prevents protein aggregation during purification and handling and obviates the need for supplementary reducing agent during bulk drug product manufacturing. Removal or replacement of cysteine residues increases drug stability in excipients suitable for in-human use.

Cysteines that can be removed or modified while preserving the prophylactic or therapeutic activity of the polypeptide include the cysteines at positions 25, 38, and 54 of the reference oligoadenylate synthetase polypeptide sequence of FIG. 1. The cysteine at position 25 is surface exposed and modified by iodoacetamide in the porcine form. This cysteine is neither strongly conserved nor does it have a strong interaction with any other functional group of the protein. The cysteine at position 38 with reference to FIG. 1 is also solvent exposed and modified by iodoacetamide in the porcine structure. This cysteine forms a weak hydrogen bond to the valine 58 backbone and is poorly conserved. Cysteine 54 hydrogen bonds to the valine 53 backbone, but is not conserved and appears to have no important interaction elsewhere on the structure. Because of their solvent exposure, weak interaction with other parts of the protein structure, and poor conservation, each of these three amino acids can be deleted or modified to increase oxidation resistance and protein stability in vitro and in vivo while preserving prophylactic or therapeutic activity.

The remaining seven cysteine residues can be modified with varying degrees of reduction in prophylactic or therapeutic activity. Cysteine 45 is in a hydrophobic pocket and conserved in the active (C-terminal) domains of OAS2 and 3. Cysteine 109 is in a hydrophobic pocket. Cysteine 177 is buried and possibly hydrogen bonds to the polypeptide backbone. Cysteine 189 is buried, hydrogen bonds to glutamine 91 and phenylalanine 153, and is highly conserved. Cysteine 219 is located in a hydrophobic neighborhood and possibly hydrogen bonds with tryptophan 215. Further, this amino acid is relatively well conserved in OAS 1, 2, and 3. Cysteine 269 is surface exposed, but hydrogen bonds to the backbone of the conserved leucine 291 and is itself highly conserved. Finally, cysteine 331 is buried within the structure and hydrogen bonds with the backbone of leucine 4. For these reasons, the foregoing seven cysteine residues respond more poorly to modification.

The polypeptides of the invention include all oligoadenylate synthetase polypeptides that are modified to reduce oxidative potential, including but not limited to the polypeptides of FIG. 1.

Class III Polypeptide Modifications

The Class III modifications of the present invention result in polypeptides having increased cell permeability by virtue of the addition of basic residues at the amino-terminus of the proteins. Histidine, arginine, and lysine residues all increase the cell permeability of the native protein. As one skilled in the art will recognize, any length of homopolymeric basic residues can increase polypeptide cell permeability (U.S. Pat. No. 4,847,240). Modification of the amino terminus of the protein preserves full enzymatic activity while increasing cell permeability. In some cases, the cell permeability of the polypeptide can be increased more than ten-fold by addition of a Class III modification. Nevertheless, all of the oligoadenylate synthetases of the invention have some cell penetrating ability, even in the absence of a Class III modification. It is therefore the intention of the present invention to include uses of the polypeptides of the invention, including the parent polypeptide of SEQUENCE:1 (SEQ ID NO:1), FIG. 1, and any fragments or subsequences thereof, to mediate an increase in cell permeability of any other molecule. Said increase in cell permeability can be affected by any covalent or non-covalent attachment between the polypeptides of the invention and the molecule in need of increased cell permeability.

Class IV Polypeptide Modifications

The Class IV modifications of the present invention result in polypeptides having increased serum stability, reduced immunogenicity, reduced susceptibility to nucleases in vivo, and increased cell permeability by virtue of their modification with polyethylene glycol. As one skilled in the art will recognize, numerous methods of derivatization of proteins with polyethylene glycol are known. Preferred embodiments include the derivatization of one or more reactive cysteine residues using a maleimide coupling reagent to a single or branched-chain polyethylene glycol of 40 kilodaltons or less in molecular weight. Such polyethylene coupled polypeptides retain full enzymatic activity as demonstrated in FIG. 6. Pegylation of the polypeptides of the present invention at one or more solvent exposed cysteines, including but not limited to the cysteines at position 25, 38, and 54, is also envisioned. Further, modification or mutation of the protein to remove one or more solvent exposed cysteines (a Class II modification) in order to facilitate the preferential polyethylene glycol derivatization of any other cysteine (a Class IV modification) is also envisioned by the present invention.

The polypeptides of the invention include all oligoadenylate synthetase polypeptides that are conjugated to a non-polypeptide moiety, such moieties include but are not limited to polymer molecules, sugar moieties, lipophilic compounds, or organic derivatizing agents.

Class V Polypeptide Modifications

The Class V modifications of the present invention represent additional polypeptide forms that also possess desirable pharmaceutical properties. These modifications are derived in order to achieve one or more of the following: simplify recombinant vector construction; optimize the ribosomal binding site; improve manufacturability in *E. coli*; and increase amino acid similarity with other identified OAS polypeptides, while maintaining desirable pharmaceutical properties such as anti-viral or anti-cancer activity.

Pharmaceutical Compositions

The invention provides pharmaceutical compositions of the polypeptides as active ingredients for a therapeutic application. These compositions can also be used in the method of the present invention. In general the pharmaceutical composition for inhibiting virus infection, cancer, neoplasm, inflammation, or other disease in a mammal or subject includes an effective amount of at least one polypeptide as described above needed for the practice of the invention, or a fragment thereof shown to have the same effect, and a pharmaceutically physiologically acceptable carrier or diluent. According to the present invention, a pharmaceutical composition can be composed of two or more of the polypeptides of FIG. 1 in combination. The pharmaceutical composition may further be composed of a single polypeptide that contains one or more of the modifications of FIG. 1 within a contiguous molecule.

The compositions can be administered orally, subcutaneously, or parenterally including intravenous, intraarterial, intramuscular, intraperitoneally, and intranasal administration, as well as intrathecal and infusion techniques as required. The pharmaceutically acceptable carriers, diluents, adjuvants and vehicles as well as implant carriers generally refer to inert, non-toxic solid or liquid fillers, diluents or encapsulating material not reacting with the active ingredients of the invention. Cationic lipids may also be included in the composition to facilitate polypeptide uptake. Implants of the compounds are also useful. In general, the pharmaceutical compositions are sterile.

The present invention relates to compositions of the polypeptides to which a detectable label is attached, such as a fluorescent, chemiluminescent or radioactive molecule.

Another example is a pharmaceutical composition which may be formulated by known techniques using known materials, see, Remington's Pharmaceutical Sciences, 18th Ed. (1990, Mack Publishing Co., Easton, Pa. 18042) pp. 1435-1712, which are herein incorporated by reference. Generally, the formulation will depend on a variety of factors such as administration, stability, production concerns and other factors. The polypeptides of FIG. 1 may be administered by injection or by pulmonary administration via inhalation. Enteric dosage forms may also be available, and therefore oral administration may be effective. The polypeptides of the invention may be inserted into liposomes or other microcarriers for delivery, and may be formulated in gels or other compositions for sustained release. Although preferred compositions will vary depending on the use to which the composition will be put, generally, for the polypeptides of the present invention, preferred pharmaceutical compositions are those prepared for subcutaneous injection or for pulmonary administration via inhalation, although the particular formulations for each type of administration will depend on the characteristics of the specific polypeptide.

Therapeutic formulations of the polypeptides or polypeptide conjugates of the invention are typically administered in a composition that includes one or more pharmaceutically acceptable carriers or excipients. Such pharmaceutical compositions may be prepared in a manner known per se in the art to result in a polypeptide pharmaceutical that is sufficiently storage-stable and is suitable for administration to humans or animals.

The polypeptides or polypeptide conjugates of the invention can be used "as is" and/or in a salt form thereof. Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

"Pharmaceutically acceptable" means a carrier or excipient that at the dosages and concentrations employed does not cause any untoward effects in the patients to whom it is administered. Such pharmaceutically acceptable carriers and excipients are well known in the art (see Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)).

The composition of the invention may be administered alone or in conjunction with other therapeutic agents. Ribavirin and interferon alpha, for example, have been shown to be an effective treatment for HCV infection when used in combination. Their efficacy in combination exceeds the efficacy of either drug product when used alone. The compositions of the invention may be administered alone or in combination with interferon, ribavirin and/or a variety of small molecules that are being developed against both viral targets (viral proteases, viral polymerase, assembly of viral replication complexes) and host targets (host proteases required for viral processing, host kinases required for phosphorylation of viral targets such as NS5A and inhibitors of host factors required to efficiently utilize the viral IRES). Cytokines may be co-administered, such as for example IL-2, IL-12, IL-23, IL-27, or IFN-gamma. These agents may be incorporated as part of the same pharmaceutical composition or may be administered separately from the polypeptides or conjugates of the invention, either concurrently or in accordance with another treatment schedule. In addition, the polypeptides, polypeptide conjugates or compositions of the invention may be used as an adjuvant to other therapies.

A "patient" for the purposes of the present invention includes both humans and other mammals. Thus the methods are applicable to both human therapy and veterinary applications.

The pharmaceutical composition comprising the polypeptide or conjugate of the invention may be formulated in a variety of forms, e.g., as a liquid, gel, lyophilized, or as a compressed solid. The preferred form will depend upon the particular indication being treated and will be apparent to one skilled in the art.

The administration of the formulations of the present invention can be performed in a variety of ways, including, but not limited to, orally, subcutaneously, intravenously, intracerebrally, intranasally, transdermally, intraperitoneally, intramuscularly, intrapulmonary, intrathecally, vaginally, rectally, intraocularly, or in any other acceptable manner. The formulations can be administered continuously by infusion, although bolus injection is acceptable, using techniques well known in the art, such as pumps (e.g., subcutaneous osmotic pumps) or implantation. In some instances the formulations may be directly applied as a solution or spray.

An example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

Parenterals may be prepared for storage as lyophilized formulations or aqueous solutions by mixing, as appropriate, the polypeptide having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives are added to retard microbial growth, and are typically added in amounts of about 0.2%-1% (w/v). Suitable preservatives for use with the present invention include phenol, benzyl alcohol, meta-cresol, methyl paraben, propyl paraben, octadecyldimethylbenzyl ammonium chloride, benzalkonium halides (e.g., benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, alpha-monothioglycerol and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active protein weight.

Non-ionic surfactants or detergents (also known as "wetting agents") may be present to help solubilize the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.).

Additional miscellaneous excipients include bulking agents or fillers (e.g., starch), chelating agents (e.g., EDTA), antioxidants (e.g., ascorbic acid, methionine, vitamin E) and cosolvents.

The active ingredient may also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences, supra.

In one aspect of the invention the composition is a liquid composition, such as an aqueous composition, and comprises a sulfoalkyl ether cyclodextrin derivative.

Parenteral formulations to be used for in vivo administration must be sterile. This is readily accomplished, for example, by filtration through sterile filtration membranes.

Suitable examples of sustained-release preparations include semi-permeable matrices of solid hydrophobic polymers containing the polypeptide or conjugate, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the ProLease® technology or Lupron Depot® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Oral administration of the peptides and peptide conjugates is an intended practice of the invention. For oral administration, the pharmaceutical composition may be in solid or liquid form, e.g., in the form of a capsule, tablet, suspension, emulsion or solution. The pharmaceutical composition is preferably made in the form of a dosage unit containing a given amount of the active ingredient. A suitable daily dose for a human or other mammal may vary widely depending on the condition of the patient and other factors, but can be determined by persons skilled in the art using routine methods.

Solid dosage forms for oral administration may include capsules, tablets, suppositories, powders and granules. In such solid dosage forms, the active compound may be admixed with at least one inert diluent such as sucrose, lactose, or starch. Such dosage forms may also comprise, as is normal practice, additional substances, e.g., lubricating agents such as magnesium stearate. In the case of capsules, tablets and pills, the dosage forms may also comprise buffering agents. Tablets and pills can additionally be prepared with enteric coatings.

The polypeptides or conjugates may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, they may be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be subjected to conventional pharmaceutical operations such as sterilization and/or may contain conventional adjuvants such as preservatives, stabilizers, wetting agents, emulsifiers, buffers, fillers, etc., e.g., as disclosed elsewhere herein.

Liquid dosage forms for oral administration may include pharmaceutically acceptable emulsions, solutions, suspensions, syrups and elixirs containing inert diluents commonly used in the art, such as water. Such compositions may also comprise adjuvants such as wetting agents, sweeteners, flavoring agents and perfuming agents.

Formulations suitable for pulmonary administration are intended as part of the invention. Formulations suitable for use with a nebulizer, either jet or ultrasonic, will typically comprise the polypeptide or conjugate dissolved in water at a concentration of, e.g., about 0.01 to 25 mg of conjugate per mL of solution, preferably about 0.1 to 10 mg/mL. The formulation may also include a buffer and a simple sugar (e.g., for protein stabilization and regulation of osmotic pressure), and/or human serum albumin ranging in concentration from 0.1 to 10 mg/ml. Examples of buffers that may be used are sodium acetate, citrate and glycine. Preferably, the buffer will have a composition and molarity suitable to adjust the solution to a pH in the range of 3 to 9. Generally, buffer molarities of from 1 mM to 50 mM are suitable for this purpose. Examples of sugars which can be utilized are lactose, maltose, mannitol, sorbitol, trehalose, and xylose, usually in amounts ranging from 1% to 10% by weight of the formulation.

The nebulizer formulation may also contain a surfactant to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001% and 4% by weight of the formulation. An especially preferred surfactant for purposes of this invention is polyoxyethylene sorbitan monooleate.

Specific formulations and methods of generating suitable dispersions of liquid particles of the invention are described in WO 94/20069, U.S. Pat. No. 5,915,378, U.S. Pat. No. 5,960,792, U.S. Pat. No. 5,957,124, U.S. Pat. No. 5,934,272, U.S. Pat. No. 5,915,378, U.S. Pat. No. 5,855,564, U.S. Pat. No. 5,826,570 and U.S. Pat. No. 5,522,385 which are hereby incorporated by reference.

Formulations for use with a metered dose inhaler device will generally comprise a finely divided powder. This powder may be produced by lyophilizing and then milling a liquid conjugate formulation and may also contain a stabilizer such as human serum albumin (HSA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the conjugate present. Such formulations are then lyophilized and milled to the desired particle size.

The properly sized particles are then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant. This mixture is then loaded into the delivery device. An example of a commercially available metered dose inhaler suitable for use in the present invention is the Ventolin metered dose inhaler, manufactured by Glaxo Inc., Research Triangle Park, N.C., USA.

Formulations for powder inhalers will comprise a finely divided dry powder containing polypeptides or polypeptide conjugates and may also include a bulking agent, such as lactose, sorbitol, sucrose, or mannitol in amounts which facilitate dispersal of the powder from the device, e.g., 50% to 90% by weight of the formulation. The particles of the powder shall have aerodynamic properties in the lung corresponding to particles with a density of about 1 g/$cm^2$ having a median diameter less than 10 micrometers, preferably between 0.5 and 5 micrometers, most preferably of between 1.5 and 3.5 micrometers. An example of a powder inhaler suitable for use in accordance with the teachings herein is the Spinhaler powder inhaler, manufactured by Fisons Corp., Bedford, Mass., USA. The powders for these devices may be generated and/or delivered by methods disclosed in U.S. Pat. No. 5,997,848, U.S. Pat. No. 5,993,783, U.S. Pat. No. 5,985,248, U.S. Pat. No. 5,976,574, U.S. Pat. No. 5,922,354, U.S. Pat. No. 5,785,049 and U.S. Pat. No. 5,654,007.

Mechanical devices designed for pulmonary delivery of therapeutic products, include but are not limited to nebulizers, metered dose inhalers, and powder inhalers, all of which are familiar to those of skill in the art. Specific examples of commercially available devices suitable for the practice of this invention are the Ultravent nebulizer, manufactured by Mallinckrodt, Inc., St. Louis, Mo., USA; the Acorn II nebulizer, manufactured by Marquest Medical Products, Englewood, Colo., USA; the Ventolin metered dose inhaler, manufactured by Glaxo Inc., Research Triangle Park, N.C., USA; the Spinhaler powder inhaler, manufactured by Fisons Corp., Bedford, Mass., USA the "standing cloud" device of Nektar Therapeutics, Inc., San Carlos, Calif., USA; the AIR inhaler manufactured by Alkermes, Cambridge, Mass., USA; and the AERx pulmonary drug delivery system manufactured by Aradigm Corporation, Hayward, Calif., USA.

The present invention also provides kits including the polypeptides, conjugates, polynucleotides, expression vectors, cells, methods, compositions, and systems, and apparatuses of the invention. Kits of the invention optionally comprise at least one of the following of the invention: (1) an apparatus, system, system component, or apparatus component as described herein; (2) at least one kit component comprising a polypeptide or conjugate or polynucleotide of the invention; a plasmid expression vector encoding a polypeptide of the invention; a cell expressing a polypeptide of the invention; or a composition comprising at least one of any such component; (3) instructions for practicing any method described herein, including a therapeutic or prophylactic method, instructions for using any component identified in (2) or any composition of any such component; and/or instructions for operating any apparatus, system or component described herein; (4) a container for holding said at least one such component or composition, and (5) packaging materials.

In a further aspect, the present invention provides for the use of any apparatus, component, composition, or kit described above and herein, for the practice of any method or assay described herein, and/or for the use of any apparatus, component, composition, or kit to practice any assay or method described herein.

Chemical Modifications, Conjugates, and Fusions

Any polypeptide of the invention may be present as part of a larger polypeptide sequence, e.g. a fusion protein, such as occurs upon the addition of one or more domains or subsequences for stabilization or detection or purification of the polypeptide. A polypeptide purification subsequence may include, e.g., an epitope tag, a FLAG tag, a polyhistidine sequence, a GST fusion, or any other detection/purification subsequence or "tag" known in the art. These additional domains or subsequences either have little or no effect on the activity of the polypeptide of the invention, or can be removed by post synthesis processing steps such as by treatment with a protease, inclusion of an intein, or the like.

The invention includes fusion proteins comprising a polypeptide of the invention, e.g., as described herein, fused to an 1 g molecule, e.g., a human IgG Fc ("fragment crystallizable," or fragment complement binding) hinge, CH2 domain and CH3 domain, and nucleotide sequences encoding such fusion protein. Fc is the portion of the antibody responsible for binding to antibody receptors on cells and the C1q component of complement. These fusion proteins and their encoding nucleic acids are useful as prophylactic and/or therapeutic drugs or as diagnostic tools (see also, e.g., Challita-Eid, P. et al. (1998) J. Immunol. 160:3419-3426; Sturmhoefel, K. et al. (1999) Cancer Res 59:4964-4972). The invention also includes fusion proteins comprising a polypeptide of the invention, fused to an albumin molecule, such as human serum albumin (HSA), as described, for example, in U.S. Pat. No. 5,876,969, and nucleotide sequences encoding the fusion protein. The Ig and albumin fusion proteins may exhibit increased polypeptide serum half-life and/or functional in vivo half-life, reduced polypeptide antigenicity, increased polypeptide storage stability, or increasing bioavailability, e.g. increased $AUC_{sc}$, and are thus may be useful as prophylactic and/or therapeutic drugs.

All of the polypeptides of the invention have an inherent ability to transduce across cellular membranes and affect therapeutic functions within cells. The invention therefore provides for the use of the polypeptides of the invention to enhance the cell permeability or transducibility of any other molecule. The invention further provides for the use of any fragment or subfragment of the polypeptides of the invention to enhance the cell permeability of any other molecule, such fragments or subfragments being of about 5 amino acids in length, of about 10 amino acids in length, such as 15 amino acids in length, e.g. about 20 amino acids in length, of about 25 amino acids in length, of about 30 amino acids in length, such as 35 amino acids in length, of about 35-50 amino acids in length, of about 50-100 amino acids in length, such as 75 amino acids in length, e.g. 100-125 amino acids in length.

Any polypeptide of the invention may also comprise one or more modified amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. The presence of modified amino acids may be advantageous in, for example, (a) increasing polypeptide serum half-life and/or functional in vivo half-life, (b) reducing polypeptide antigenicity, (c) increasing polypeptide storage stability, or (d) increasing bioavailability, e.g. increasing the $AUC_{sc}$.

Amino acid(s) are modified, for example, co-translationally or post-translationally during recombinant production (e.g., N-linked glycosylation at N—X—S/T motifs during expression in mammalian cells) or modified by synthetic means. Pegylated polypeptides of the invention include but are not limited to the polypeptide modifications described as Class IV in FIG. 1 and as implemented in FIG. 6.

Figure 6:
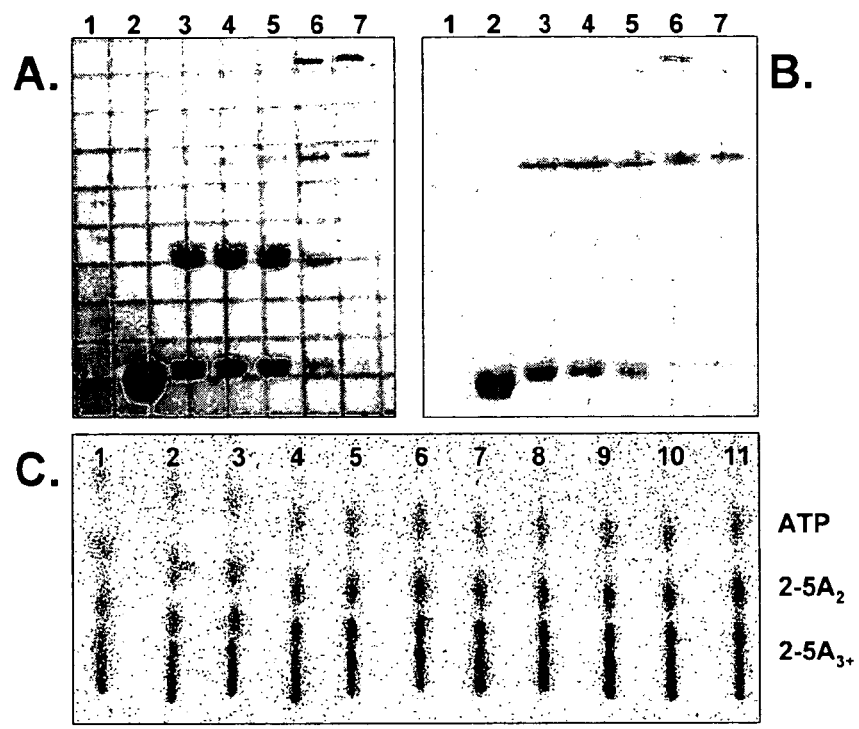

In another aspect, the invention relates to a conjugate comprising a polypeptide of the invention and at least one non-polypeptide moiety attached to the polypeptide, such as e.g. those modified polypeptides described as Class IV in FIG. 1 and as implemented in FIG. 6.

The invention provides for polypeptides that differ from the polypeptides of FIG. 1 by 1 to 34 amino acid substitutions or insertions where such substitutions or insertions introduce one or more attachment groups for the non-polypeptide moiety (e.g., by substitution of an amino acid residue for a different residue which comprises an attachment group for the non-polypeptide moiety, or by insertion of an additional amino acid residue which comprises an attachment group for the non-polypeptide moiety).

The term "conjugate" (or interchangeably "polypeptide conjugate" or "conjugated polypeptide") is intended to indicate a heterogeneous (in the sense of composite) molecule formed by the covalent attachment of one or more polypeptides of the invention to one or more non-polypeptide moieties. The term "covalent attachment" means that the polypeptide and the non-polypeptide moiety are either directly covalently joined to one another, or else are indirectly covalently joined to one another through an intervening moiety or moieties, such as a bridge, spacer, or linkage moiety or moieties. Preferably, a conjugated polypeptide is soluble at relevant concentrations and conditions, i.e. soluble in physiological fluids such as blood. Examples of conjugated polypeptides of the invention include glycosylated and/or PEGylated polypeptides. The term "non-conjugated polypeptide" may be used to refer to the polypeptide part of the conjugated polypeptide.

The term "non-polypeptide moiety" is intended to mean a molecule that is capable of conjugating to an attachment group of the polypeptide. Preferred examples of non-polypeptide moieties include polymer molecules, sugar moieties, lipophilic compounds, or organic derivatizing agents, in particular polymer molecules or sugar moieties. It will be understood that the non-polypeptide moiety is linked to the polypeptide through an attachment group of the polypeptide. Except where the number of non-polypeptide moieties, such as polymer molecule(s), attached to the polypeptide is expressly indicated, every reference to "a non-polypeptide moiety" attached to the polypeptide or otherwise used in the present invention shall be a reference to one or more non-polypeptide moieties attached to the polypeptide.

The term "polymer molecule" is defined as a molecule formed by covalent linkage of two or more monomers, wherein none of the monomers is an amino acid residue. The term "polymer" may be used interchangeably with the term "polymer molecule".

The term "sugar moiety" is intended to indicate a carbohydrate molecule attached by in vivo or in vitro glycosylation, such as N- or O-glycosylation. An "N-glycosylation site" has the sequence N—X—S/T/C, wherein X is any amino acid residue except proline, N is asparagine and S/T/C is either serine, threonine or cysteine, preferably serine or threonine, and most preferably threonine. An "O-glycosylation site" comprises the OH-group of a serine or threonine residue.

The term "attachment group" is intended to indicate an amino acid residue group capable of coupling to the relevant non-polypeptide moiety such as a polymer molecule or a sugar moiety.

For in vivo N-glycosylation, the term "attachment group" is used in an unconventional way to indicate the amino acid residues constituting an N-glycosylation site (with the sequence N—X—S/T/C, wherein X is any amino acid residue except proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site is present. Accordingly, when the non-polypeptide moiety is a sugar moiety and the conjugation is to be achieved by N-glycosylation, the term "amino acid residue comprising an attachment group for the non-polypeptide moiety" as used in connection with alterations of the amino acid sequence of the polypeptide of the invention is to be understood as one, two or all of the amino acid residues constituting an N-glycosylation site is/are to be altered in such a manner that either a functional N-glycosylation site is introduced into the amino acid sequence, removed from said sequence, or a functional N-glycosylation site is retained in the amino acid sequence (e.g. by substituting a serine residue, which already constitutes part of an N-glycosylation site, with a threonine residue and vice versa).

The term "introduce" (i.e., an "introduced" amino acid residue, "introduction" of an amino acid residue) is primarily intended to mean substitution of an existing amino acid residue for another amino acid residue, but may also mean insertion of an additional amino acid residue.

The term "remove" (i.e., a "removed" amino acid residue, "removal" of an amino acid residue) is primarily intended to mean substitution of the amino acid residue to be removed for another amino acid residue, but may also mean deletion (without substitution) of the amino acid residue to be removed.

The term "amino acid residue comprising an attachment group for the non-polypeptide moiety" is intended to indicate that the amino acid residue is one to which the non-polypeptide moiety binds (in the case of an introduced amino acid residue) or would have bound (in the case of a removed amino acid residue).

The term "functional in vivo half-life" is used in its normal meaning, i.e. the time at which 50% of the biological activity of the polypeptide is still present in the body/target organ, or the time at which the activity of the polypeptide is 50% of the initial value. The functional in vivo half-life may be determined in an experimental animal, such as rat, mouse, rabbit, dog or monkey. Preferably, the functional in vivo half-life is determined in a non-human primate, such as a monkey. Furthermore, the functional in vivo half-life may be determined for a sample that has been administered intravenously or subcutaneously.

As an alternative to determining functional in vivo half-life, "serum half-life" may be determined, i.e. the time at which 50% of the polypeptide circulates in the plasma or bloodstream prior to being cleared. Determination of serum half-life is often more simple than determining the functional in vivo half-life and the magnitude of serum half-life is usually a good indication of the magnitude of functional in vivo half-life. Alternatively terms to serum half-life include "plasma half-life", "circulating half-life", "serum clearance", "plasma clearance" and "clearance half-life".

The term "serum" is used in its normal meaning, i.e. as blood plasma without fibrinogen and other clotting factors.

The term "increased" as used about the functional in vivo half-life or serum half-life is used to indicate that the relevant half-life of the conjugate of the invention is statistically significantly increased relative to that of a reference molecule or the corresponding non-conjugated polypeptide. Thus, interesting conjugates of the invention include those which have an increased functional in vivo half-life or an increased serum half-life as compared to a reference molecule mentioned above.

The term "$AUC_{sc}$" or "Area Under the Curve when administered subcutaneously" is used in its normal meaning, i.e., as the area under the drug concentration vs. time curve, where the conjugated molecule has been administered subcutaneously to an experimental animal. Once the experimental drug concentration time points have been determined, the $AUC_{sc}$ may conveniently be calculated by a computer program, such as GraphPad Prism 3.01.

The term "increased" as used about the $AUC_{sc}$ is used to indicate that the Area Under the Curve for a conjugate of the invention, when administered subcutaneously, is statistically significantly increased relative to that of a reference molecule or the corresponding non-conjugated polypeptide, when determined under comparable conditions.

The term "$T_{max,sc}$" is used about the time point in the drug concentration vs. time curve where the highest drug concentration in serum is observed.

By removing and/or introducing amino acid residues comprising an attachment group for the non-polypeptide moiety it is possible to specifically adapt the polypeptide so as to make the molecule more susceptible to conjugation to the non-polypeptide moiety of choice, to optimize the conjugation pattern (e.g. to ensure an optimal distribution of non-polypeptide moieties on the surface of the oliagoadenylate synthetase molecule and thereby, e.g., effectively shield epitopes and other surface parts of the polypeptide without significantly impairing the function thereof). For instance, by introduction of attachment groups, the oligoadenylate synthetase polypeptide is altered in the content of the specific amino acid residues to which the relevant non-polypeptide moiety binds, whereby a more efficient, specific and/or extensive conjugation is achieved. By removal of one or more attachment groups it is possible to avoid conjugation to the non-polypeptide moiety in parts of the polypeptide in which such conjugation is disadvantageous, e.g., to an amino acid residue located at or near a functional site of the polypeptide (since conjugation at such a site may result in inactivation or reduced therapeutic or prophylactic activity of the resulting conjugate). Further, it may be advantageous to remove an attachment group located close to another attachment group.

It will be understood that the amino acid residue comprising an attachment group for a non-polypeptide moiety, whether it be removed or introduced, is selected on the basis of the nature of the non-polypeptide moiety and, in some instances, on the basis of the conjugation method to be used. For instance, when the non-polypeptide moiety is a polymer molecule, such as a polyethylene glycol or polyalkylene oxide derived molecule, amino acid residues capable of functioning as an attachment group may be selected from the group consisting of cysteine, lysine (and/or the N-terminal amino group of the polypeptide), aspartic acid, glutamic acid, histidine and arginine. When the non-polypeptide moiety is a sugar moiety, the attachment group is an in vivo or in vitro N- or O-glycosylation site, preferably an N-glycosylation site.

In case of removal of an attachment group, the relevant amino acid residue comprising such group and occupying a position as defined above may be substituted with a different amino acid residue that does not comprise an attachment group for the non-polypeptide moiety in question, or may be deleted. Removal of an N-glycosylation group, may also be accomplished by insertion or removal of an amino acid reside within the motif N—X—S/T/C. In case of introduction of an attachment group, an amino acid residue comprising such group is introduced into the position, such as by substitution of the amino acid residue occupying such position.

The exact number of attachment groups available for conjugation is dependent on the effect desired to be achieved by conjugation. The effect to be obtained is, e.g., dependent on the nature and degree of conjugation (e.g. the identity of the non-polypeptide moiety, the number of non-polypeptide moieties desirable or possible to conjugate to the polypeptide, where they should be conjugated or where conjugation should be avoided, etc.). For instance, if reduced immunogenicity is desired, the number (and location of) attachment groups should be sufficient to shield most or all epitopes. This is normally obtained when a greater proportion of the polypeptide is shielded. Effective shielding of epitopes is normally achieved when the total number of attachment groups available for conjugation is in the range of 1-6 attachment groups, e.g., 1-5, such as in the range of 1-3, such as 1, 2, or 3 attachment groups.

Functional in vivo half-life is i.a. dependent on the molecular weight of the conjugate, and the number of attachment groups needed for providing increased half-life thus depends on the molecular weight of the non-polypeptide moiety in question. Some such conjugates comprise 1-6, e.g., 1-5, such as 1-3, e.g. 1, 2, or 3 non-polypeptide moieties each having a MW of about 2-40 kDa, such as about 2 kDa, about 5 kDa, about 12 kDa, about 15 kDa, about 20 kDa, about 30 kDa, or about 40 kDa.

In the conjugate of the invention, some, most, or substantially all conjugatable attachment groups are occupied by the relevant non-polypeptide moiety.

The conjugate of the invention may exhibit one or more of the following improved properties. For example, the conjugate may exhibit a reduced immunogenicity as compared to the corresponding non-conjugated polypeptide, e.g. a reduction of at least 10%, such as a reduction of at least of 25%, such as a reduction of at least of 50%, e.g. a reduction of at least 75% compared to the non-conjugated polypeptide. In another aspect the conjugate may exhibit a reduced reaction or no reaction with neutralizing antibodies from patients treated with the parent polypeptide as compared to the corresponding non-conjugated polypeptide, e.g., a reduction of neutralization of at least 10%, such as at least 25%, such as of at least 50%, e.g., at least 75%.

In another aspect of the invention the conjugate may exhibit an increased functional in vivo half-life and/or increased serum half-life as compared to a reference molecule or as compared to the corresponding non-conjugated polypeptide. Particular preferred conjugates are such conjugates where the ratio between the functional in vivo half-life (or serum half-life) of said conjugate and the functional in vivo half-life (or serum half-life) of said reference molecule is at least 1.25, such as at least 1.50, such as at least 1.75, such as at least 2, such as at least 3, such as at least 4, such as at least 5, such as at least 6, such as at least 7, such as at least 8, such as at least 9, e.g. 10-100. As mentioned above, the half-life is conveniently determined in an experimental animal, such as rat or monkey, and may be based on intravenous, subcutaneous, or other route of administration.

In a further aspect the conjugate may exhibit an increased bioavailability as compared to a reference molecule or the corresponding non-conjugated polypeptide. For example, the conjugate may exhibit an increased $AUC_{sc}$ as compared to a reference molecule or the corresponding non-conjugated polypeptide. Thus, exemplary conjugates are such conjugates where the ratio between the $AUC_{sc}$ of said conjugate and the $AUC_{sc}$ of said reference molecule is at least 1.25, such as at least 1.5, such as at least 2, such as at least 3, such as at least 4, such as at least 5 or at least 6, such as at least 7, such as at least 8, such as at least 9 or at least 10, such as at least 12, such as at least 14, e.g. at least 16, at least 18 or at least 20 when administered subcutaneously, intravenously, intrathecally, intramuscularly, or intraperitoneally, or by ingestion or inhalation, in particular when administered subcutaneously in an experimental animal such as rat or monkey. Analogously, some conjugates of the invention are such conjugates wherein the ratio between $T_{max}$ for said conjugate and $T_{max}$ for said reference molecule, or the corresponding non-conjugated polypeptide, is at least 1.2, such as at least 1.4, e.g. at least 1.6, such as at least 1.8, such as at least 2, e.g., at least 2.5, such as at least 3, such as at least 4, e.g. at least 5, such as at least 6, such as at least 7, e.g. at least 8, such as at least 9, such as at least 10, when administered subcutaneously, intravenously, intrathecally, intramuscularly, or intraperitoneally, or by ingestion or inhalation, in particular when administered subcutaneously in an experimental animal such as rat or monkey.

In some instances, the magnitude of the antiviral, anticancer, anti-neoplastic, anti-inflammatory, pro-regenerative or other therapeutic activity of a conjugate of the invention may be reduced (e.g., by at least about 75%, at least about 50%, at least about 25%, at least about 10%) or increased (e.g. by at least about 10%) or is about equal (e.g. within about +/−10% or about +/−5%) to that of the corresponding non-conjugated polypeptide.

In one aspect, the invention relates to a conjugate comprising at least one non-polypeptide moiety conjugated to at least one lysine residue and/or to the N-terminal amino group of a polypeptide of the invention most particularly the polypeptides described in FIG. 1.

In another aspect, the invention relates to a conjugate comprising at least one non-polypeptide moiety conjugated to at least one lysine residue, or to the N-terminal amino group, of a polypeptide comprising a sequence which differs in 1 to 34 amino acid positions from SEQUENCE:1 (SEQ ID NO:1) of FIG. 1.

Some conjugates of the invention comprise a polypeptide sequence comprising a substitution of an amino acid residue for a different amino acid residue, or a deletion of an amino acid residue, which removes one or more lysines from a polypeptide of the invention. The one or more lysine residue(s) to be removed may be substituted with any other amino acid, may be substituted with an Arg (R), His(H) or Gln (Q), or may be deleted.

In instances where amine-reactive conjugation chemistries are employed, it may be advantageous to avoid or to minimize the potential for conjugation to histidine residues. Therefore, some conjugates of the invention comprise a polypeptide sequence comprising a substitution or a deletion which removes one or more histidines from any polypeptide sequence of the invention. The one or more histidine residue(s) to be removed may be substituted with any other amino acid, may be substituted with an Arg (R), Lys(L) or Gln (Q), or may be deleted.

Alternatively, or in addition, some conjugates of the invention comprise a polypeptide sequence comprising a modification which introduces a lysine into a position that is occupied in the parent sequence by an amino acid residue that is exposed to the surface of the molecule, e.g., one that has at least 25%, such as at least 50% of its side chain exposed to the surface.

Non-polypeptide moieties contemplated for this aspect of the invention include polymer molecules, such as PEG or mPEG or mPEG2. The conjugation between the lysine-containing polypeptide and the polymer molecule may be achieved in any suitable manner as known in the art. An exemplary method for PEGylating the polypeptide is to covalently attach PEG to lysine residues using lysine-reactive PEGs. A number of highly specific, lysine-reactive PEGs (such as for example, succinimidyl propionate (SPA), succinimidyl butanoate (SBA), N-hydroxylsuccinimide (NHS), and aldehyde (e.g., ButyrALD)) and different size linear or branched PEGs (e.g., 2-40 kDa, such as 2 kDa, 5 kDa, 12 kDa, 15 kDa, 20 kDa, 30 kDa, or 40 kDa) are commercially available, e.g. from Nektar Therapeutics Inc., Huntsville, Ala., USA, or SunBio, Anyang City, South Korea.

In another aspect, the invention includes a composition comprising a population of conjugates wherein the majority of the conjugates of said population each contain a single non-polypeptide moiety (such as, a single polymer molecule, e.g., a single PEG, such as a linear PEG or a branched PEG) covalently attached to a single lysine residue or N-terminal amino group of the polypeptide. For example, a "monoconjugated" (such as, a "monoPEGylated") composition of the invention comprises one or more "positional isomers" of said conjugate, wherein each positional isomer contains a single non-polypeptide moiety (e.g., a single PEG molecule) covalently attached to a single lysine residue of the polypeptide.

The invention includes a monoPEGylated composition comprising a population of conjugates, wherein the majority of the conjugates of said population are positional isomers each containing a single PEG molecule (such as, a linear or branched PEG, such as a 2 kDa, 5 kDa, 12 kDa, 15 kDa, 20 kDa, 30 kDa, or 40 kDa mPEG or mPEG2 molecule) covalently attached to a single lysine residue of a polypeptide of the invention.

In one aspect, the invention relates to a conjugate comprising at least one non-polypeptide moiety conjugated to at least one cysteine residue of a polypeptide of the invention or a polypeptide comprising a sequence which differs in 1 to 34 amino acid positions from SEQUENCE:1 (SEQ ID NO:1) of FIG. 1. Some conjugates according to this aspect comprise at least one introduced cysteine residue.

In another aspect, the invention relates to conjugation of the non-polypeptide moiety to one or more cysteine residues of the polypeptides of the invention including Cys25, Cys38, Cys45, Cys54, Cys109, Cys177, Cys189, Cys219, Cys269, or Cys331. Included among these conjugates are those defined as Class IV in FIG. 1 and as implemented in FIG. 6.

In another aspect, the invention relates to the addition of one or more cysteine residues to the polypeptides of the invention to enable conjugation of a non-polypeptide moiety at a location other than Cys25, Cys38, Cys45, Cys54, Cys109, Cys177, Cys189, Cys219, Cys269, or Cys331.

It is to be understood that while the examples of modifications or conjugations to the parent polypeptide are generally provided herein relative to the sequence SEQUENCE:1 (SEQ ID NO:1) of FIG. 1 (or relative to some other specified sequence), the disclosed modifications may also be made in equivalent amino acid positions of the other polypeptides of the invention described herein.

In some instances, only a single cysteine residue is introduced in order to avoid formation of disulfide bridges between two or more introduced cysteine residues.

Non-polypeptide moieties contemplated in this aspect of the invention include polymer molecules, such as PEG or mPEG and others as known to those skilled in the art and as described herein. The conjugation between the cysteine-containing polypeptide and the polymer molecule may be achieved in any suitable manner as known to those skilled in the art. An exemplary method for PEGylating the polypeptides of the invention is to covalently attach PEG to cysteine residues using cysteine-reactive PEGs. A number of highly specific, cysteine-reactive PEGs with different groups (e.g., orthopyridyl-disulfide (OPSS), maleimide (MAL) and vinylsulfone (VS)) and different size linear or branched PEGs (e.g., 2-40 kDa, such as 2 kDa, 5 kDa, 12 kDa, 15 kDa, 20 kDa, 30 kDa, or 40 kDa) are commercially available, e.g., from Nektar Therapeutics Inc., Huntsville, Ala., USA, or SunBio, Anyang City, South Korea.

As indicated above, the non-polypeptide moiety of the conjugate of the invention is generally selected from the group consisting of a polymer molecule, a lipophilic compound, a sugar moiety (e.g., by way of in vivo N-glycosylation) and an organic derivatizing agent. All of these agents may confer desirable properties to the polypeptide part of the conjugate, such as reduced immunogenicity, increased functional in vivo half-life, increased serum half-life, increased bioavailability and/or increased $AUC_{sc}$. The polypeptide part of the conjugate is often conjugated to only one type of non-polypeptide moiety, but may also be conjugated to two or more different types of non-polypeptide moieties, e.g., to a polymer molecule and a sugar moiety, etc. The conjugation to two or more different non-polypeptide moieties may be done simultaneously or sequentially. The choice of non-polypeptide moiety/moieties, depends especially on the effect desired to be achieved by the conjugation. For instance, sugar moieties have been found particularly useful for reducing immunogenicity, whereas polymer molecules such as PEG are of particular use for increasing functional in vivo half-life and/or serum half-life. Using a combination of a polymer molecule and a sugar moiety may enhance the reduction in immunogenicity and the increase in functional in vivo or serum half-life.

For conjugation to a lipophilic compound, the following polypeptide groups may function as attachment groups: the N-terminus or C-terminus of the polypeptide, the hydroxy groups of the amino acid residues Ser, Thr or Tyr, the epsilon-amino group of Lys, the SH group of Cys or the carboxyl group of Asp and Glu. The polypeptide and the lipophilic compound may be conjugated to each other either directly or by use of a linker. The lipophilic compound may be a natural compound such as a saturated or unsaturated fatty acid, a fatty acid diketone, a terpene, a prostaglandin, a vitamin, a carotenoid or steroid, or a synthetic compound such as a carbon acid, an alcohol, an amine and sulphonic acid with one or more alkyl, aryl, alkenyl or other multiple unsaturated compounds. The conjugation between the polypeptide and the lipophilic compound, optionally through a linker may be done according to methods known in the art, e.g. as described by Bodanszky in Peptide Synthesis, John Wiley, New York, 1976 and in WO 96/12505.

The polymer molecule to be coupled to the polypeptide may be any suitable polymer molecule, such as a natural or synthetic homo-polymer or heteropolymer, typically with a molecular weight in the range of about 300-100,000 Da, such as about 1000-50,000 Da, e.g. in the range of about 1000-40,000 Da. More particularly, the polymer molecule, such as PEG, in particular mPEG, will typically have a molecular weight of about 2, 5, 10, 12, 15, 20, 30, 40 or 50 kDa, in particular a molecular weight of about 5 kDa, about 10 kDa, about 12 kDa, about 15 kDa, about 20 kDa, about 30 kDa or about 40 kDa. The PEG molecule may be branched (e.g., mPEG2), or may be unbranched (i.e., linear).

When used about polymer molecules herein, the word "about" indicates an approximate average molecular weight and reflects the fact that there will normally be a certain molecular weight distribution in a given polymer preparation.

Examples of homo-polymers include a polyol (i.e., poly-OH), a polyamine (i.e. poly-$NH_2$) and a polycarboxylic acid (i.e. poly-COOH). A hetero-polymer is a polymer which comprises one or more different coupling groups, such as a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs (PEG2), poly-vinyl alcohol (PVA), poly-carboxylate, poly-(vinylpyrolidone), polyethylene-co-maleic acid anhydride, polystyrene-co-malic acid anhydride, dextran including carboxymethyl-dextran, or any other biopolymer suitable for reducing immunogenicity and/or increasing functional in vivo half-life and/or serum half-life. Generally, polyalkylene glycol-derived polymers are biocompatible, non-toxic, non-antigenic, non-immunogenic, have various water solubility properties, and are easily excreted from living organisms.

PEG is the preferred polymer molecule to be used, since it has only few reactive groups capable of cross-linking compared to e.g., polysaccharides such as dextran. In particular, monofunctional PEG, e.g., monomethoxypolyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl propionate (SPA), succinimidyl butanoate (SBA), succinimidyl carboxymethylate (SCM), benzotriazole carbonate (BTC), N-hydroxysuccinimide (NHS), aldehyde, nitrophenylcarbonate (NPC), and tresylate (TRES)). Suitably activated polymer molecules are commercially available, e.g., from Nektar Therapeutics, Inc., Huntsville, Ala., USA; PolyMASC Pharmaceuticals plc, UK; or SunBio Corporation, Anyang City, South Korea. Alternatively, the polymer molecules can be activated by conventional methods known in the art, e.g. as disclosed in WO 90/13540.

Specific examples of activated linear or branched polymer molecules suitable for use in the present invention are described in the Nektar Therapeutics, Inc. 2003 Catalog ("Nektar Molecule Engineering Polyethylene Glycol and Derivatives for Advanced Pegylation, Catalog 2003"), incorporated by reference herein. Specific examples of activated PEG polymers include the following linear PEGs: NHS-PEG, SPA-PEG, SSPA-PEG, SBA-PEG, SS-PEG, SSA-PEG, SC-PEG, SG-PEG, SCM-PEG, NOR-PEG, BTC-PEG, EPDX-PEG, NCO-PEG, NPC-PEG, CDI-PEG, ALD-PEG, TRES-PEG, VS-PEG, OPSS-PEG, IODO-PEG, and MAL-PEG, and branched PEGs, such as PEG2-NHS, PEG2-MAL, and those disclosed in U.S. Pat. No. 5,932,462 and U.S. Pat. No. 5,643,575, both of which are incorporated herein by reference.

Furthermore, the following publications, incorporated herein by reference, disclose useful polymer molecules and/or PEGylation chemistries: U.S. Pat. No. 5,824,778, U.S. Pat. No. 5,476,653, WO 97/32607, EP 229,108, EP 402,378, U.S. Pat. No. 4,902,502, U.S. Pat. No. 5,281,698, U.S. Pat. No. 5,122,614, U.S. Pat. No. 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. No. 5,473,034, U.S. Pat. No. 5,516,673, EP 605 963, U.S. Pat. No. 5,382,657, EP 510 356, EP 400 472, EP 183 503 and EP 154 316.

The conjugation of the polypeptide and the activated polymer molecules is conducted by use of any conventional method, e.g., as described in the following references (which also describe suitable methods for activation of polymer molecules): Harris and Zalipsky, eds., Poly(ethylene glycol) Chemistry and Biological Applications, AZC, Washington; R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, New York.

For PEGylation of cysteine residues, the polypeptide is usually treated with a reducing agent, such as dithiothreitol (DDT) prior to PEGylation. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to about 16 hours. Examples of activated PEG polymers for coupling to cysteine residues include the following linear and branched PEGs: vinylsulfone-PEG (PEG-VS), such as vinylsulfone-mPEG (mPEG-VS); orthopyridyl-disulfide-PEG (PEG-OPSS), such as orthopyridyl-disulfide-mPE-G (mPEG-OPSS); and maleimide-PEG (PEG-MAL), such as maleimide-mPEG (mPEG-MAL) and branched maleimide-mPEG2 (mPEG2-MAL).

Pegylation of lysines often employs PEG-N-hydroxylsuccinimide (e.g., mPEG-NHS or mPEG2-NHS), or esters such as PEG succinimidyl propionate (e.g., mPEG-SPA) or PEG succinimidyl butanoate (e.g., mPEG-SBA). One or more PEGs can be attached to a protein within 30 minutes at pH 8-9.5 at room temperature if about equimolar amounts of PEG and protein are mixed. A molar ratio of PEG to protein amino groups of 1-5 to 1 will usually suffice. Increasing pH increases the rate of reaction, while lowering pH reduces the rate of reaction. These highly reactive active esters can couple at physiological pH, but less reactive derivatives typically require higher pH. Low temperatures may also be employed if a labile protein is being used. Under low temperature conditions, a longer reaction time may be used.

N-terminal PEGylation is facilitated by the difference between the pKa values of the alpha-amino group of the N-terminal amino acid (about 6 to 8.0) and the epsilon-amino group of lysine (about 10). PEGylation of the N-terminal amino group often employs PEG-aldehydes (such as mPEG-propionaldehyde or mPEG-butylaldehyde), which are more selective for amines and thus are less likely to react with the imidazole group of histidine; in addition, PEG reagents used for lysine conjugation (such as mPEG-SPA, mPEG-SBA, or mPEG-NHS) may also be used for conjugation of the N-terminal amine. Conjugation of a PEG-aldehyde to the N-terminal amino group typically takes place in a suitable buffer (such as, 100 mM sodium acetate or 100 mM sodium bisphosphate buffer with 20 mM sodium cyanoborohydride) at pH about 5.0 overnight at temperatures varying from about 4° C. to 25° C. Useful N-terminal PEGylation methods and chemistries are also described in U.S. Pat. No. 5,985,265 and U.S. Pat. No. 6,077,939, both incorporated herein by reference.

Typically, linear PEG or mPEG polymers will have a molecular weight of about 5 kDa, about 10 kDa, about 12 kDa, about 15 kDa, about 20 kDa, or about 30 kDa. Branched PEG (PEG2 or mPEG2) polymers will typically have a molecular weight of about 10 kDa, about 20 kDa, or about 40 kDa. In some instances, the higher-molecular weight branched PEG2 reagents, such as 20 kDa or 40 kDa PEG2, including e.g. mPEG2-NHS for lysine PEGylation, mPEG2-MAL for cysteine PEGylation, or MPEG2-aldehyde for N-terminal PEGylation (all available from Nektar Therapeutics, Inc, Huntsville Ala.), may be used. The branched structure of the PEG2 compound results in a relatively large molecular volume, so fewer attached molecules (or, one attached molecule) may impart the desired characteristics of the PEGylated molecule.

The skilled person will be aware that the activation method and/or conjugation chemistry to be used depends on the attachment group(s) of the oligoadenylate synthetase polypeptide as well as the functional groups of the polymer (e.g., being amino, hydroxyl, carboxyl, aldehyde or sulfhydryl). The PEGylation may be directed towards conjugation to all available attachment groups on the polypeptide (i.e. such attachment groups that are exposed at the surface of the polypeptide) or may be directed towards specific attachment groups, e.g. cysteine residues, lysine residues, or the N-terminal amino group. Furthermore, the conjugation may be achieved in one step or in a stepwise manner (e.g., as described in WO 99/55377).

In some instances, the polymer conjugation is performed under conditions aiming at reacting as many of the available polymer attachment groups as possible with polymer molecules. This is achieved by means of a suitable molar excess of the polymer in relation to the polypeptide. Typical molar ratios of activated polymer molecules to polypeptide are up to about 1000-1, such as up to about 200-1 or up to about 100-1. In some cases, the ratio may be somewhat lower, however, such as up to about 50-1, 10-1 or 5-1. Also equimolar ratios may be used.

It is also contemplated according to the invention to couple the polymer molecules to the polypeptide through a linker. Suitable linkers are well known to the skilled person. A preferred example is cyanuric chloride (Abuchowski et al., (1977), J. Biol. Chem., 252, 3578-3581; U.S. Pat. No. 4,179, 337; Shafer et al., (1986), J. Polym. Sci. Polym. Chem. Ed., 24, 375-378).

Subsequent to the conjugation residual activated polymer molecules are blocked according to methods known in the art, e.g., by addition of primary amine to the reaction mixture, and the resulting inactivated polymer molecules removed by a suitable method.

Covalent in vitro coupling of a sugar moiety to amino acid residues of the polypeptides of the invention may be used to modify or increase the number or profile of sugar substituents. Depending on the coupling mode used, the carbohydrate(s) may be attached to: a) arginine and histidine (Lundblad and Noyes, Chemical Reagents for Protein Modification, CRC Press Inc. Boca Raton, Fla.), b) free carboxyl groups (e.g., of the C-terminal amino acid residue, asparagine or glutamine), c) free sulfhydryl groups such as that of cysteine, d) free hydroxyl groups such as those of serine, threonine, tyrosine or hydroxyproline, e) aromatic residues such as those of phenylalanine or tryptophan or f) the amide group of glutamine. These amino acid residues constitute examples of attachment groups for a sugar moiety, which may be introduced and/or removed in the polypeptides of the invention. Suitable methods of in vitro coupling are described in WO 87/05330 and in Aplin et al., CRC Crit. Rev. Biochem., pp. 259-306, 1981. The in vitro coupling of sugar moieties or PEG to protein- and peptide-bound Gln-residues can also be carried out by transglutaminases (TGases), e.g. as described by Sato et al., 1996 Biochemistry 35, 13072-13080 or in EP 725145.

In order to achieve in vivo glycosylation of an oligoadenylate synthetase polypeptide that has been modified by introduction of one or more glycosylation sites, the nucleotide sequence encoding the polypeptide part of the conjugate is inserted in a glycosylating, eukaryotic expression host. The expression host cell may be selected from fungal (filamentous fungal or yeast), insect, mammalian animal cells, from transgenic plant cells or from transgenic animals. Furthermore, the glycosylation may be achieved in the human body when using a nucleotide sequence encoding the polypeptide part of a conjugate of the invention or a polypeptide of the invention in gene therapy. In one aspect the host cell is a mammalian cell, such as a CHO cell, a COS cell, a BHK or HEK cell, e.g., HEK293, or an insect cell, such as an SF9 cell, or a yeast cell, e.g. *Saccharomyces cerevisiae, Pichia pastoris* or any other suitable glycosylating host, e.g. as described further below. Optionally, sugar moieties attached to the oligoadenylate synthetase polypeptide by in vivo glycosylation are further modified by use of glycosyltransferases, e.g., using the GlycoAdvance™ technology marketed by Neose, Horsham, Pa., USA. Thereby, it is possible to, e.g., increase the sialyation of the glycosylated oligoadenylate synthetase polypeptide following expression and in vivo glycosylation by CHO cells.

Covalent modification of the polypeptides of the invention may be performed by reacting (an) attachment group(s) of the polypeptide with an organic derivatizing agent. Suitable derivatizing agents and methods are well known in the art. For example, cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(4-imidozoyl-)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide is also useful; the reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues.

Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group.

Furthermore, these reagents may react with the groups of lysine as well as the arginine guanidino group. Carboxyl side groups (aspartyl or glutamyl or C-terminal amino acid residue) are selectively modified by reaction with carbodiimides (R—N-double bond-C-double bond-N—W), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Since excessive polymer conjugation may lead to a loss of activity of the oligoadenylate synthetase polypeptides to which the polymer is conjugated, it may be advantageous to remove attachment groups located at the functional site or to block the functional site prior to conjugation. These latter strategies constitute further aspects of the invention (the first strategy being exemplified further above, e.g. by removal of lysine residues which may be located close to a functional site). More specifically, according to the second strategy the conjugation between the oligoadenylate synthetase polypeptide and the non-polypeptide moiety is conducted under conditions where the functional site of the polypeptide is blocked by a helper molecule capable of binding to the functional site of the polypeptide. Preferably, the helper molecule is one which specifically recognizes a functional site of the polypeptide. Alternatively, the helper molecule may be an antibody, in particular a monoclonal antibody recognizing the polypeptide. In particular, the helper molecule may be a neutralizing monoclonal antibody.

The polypeptide is allowed to interact with the helper molecule before effecting conjugation. This ensures that the functional site of the polypeptide is shielded or protected and consequently unavailable for derivatization by the non-polypeptide moiety such as a polymer. Following its elution from the helper molecule, the conjugate between the non-polypeptide moiety and the polypeptide can be recovered with at least a partially preserved functional site. The subsequent conjugation of the polypeptide having a blocked functional site to a polymer, a lipophilic compound, an organic derivatizing agent or any other compound is conducted in the normal way.

Irrespective of the nature of the helper molecule to be used to shield the functional site of the polypeptide from conjugation, it is desirable that the helper molecule is free from or comprises only a few attachment groups for the non-polypeptide moiety of choice in parts of the molecule where the conjugation to such groups would hamper the desorption of the conjugated polypeptide from the helper molecule. Hereby, selective conjugation to attachment groups present in non-shielded parts of the polypeptide can be obtained and it is possible to reuse the helper molecule for repeated cycles of conjugation. For instance, if the non-polypeptide moiety is a polymer molecule such as PEG, which has the epsilon amino group of a lysine or N-terminal amino acid residue as an attachment group, it is desirable that the helper molecule is substantially free from conjugatable epsilon amino groups, preferably free from any epsilon amino groups. Accordingly, in some instances the helper molecule is a protein or peptide capable of binding to the functional site of the polypeptide, which protein or peptide is free from any conjugatable attachment groups for the non-polypeptide moiety of choice.

In a further aspect, the helper molecule is first covalently linked to a solid phase such as column packing materials, for instance Sephadex or agarose beads, or a surface, e.g. reaction vessel. Subsequently, the polypeptide is loaded onto the column material carrying the helper molecule and conjugation carried out according to methods known in the art. This procedure allows the polypeptide conjugate to be separated from the helper molecule by elution. The polypeptide conjugate is eluted by conventional techniques under physico-chemical conditions that do not lead to a substantive degradation of the polypeptide conjugate. The fluid phase containing the polypeptide conjugate is separated from the solid phase to which the helper molecule remains covalently linked.

The separation can be achieved in other ways. For instance, the helper molecule may be derivatized with a second molecule (e.g., biotin) that can be recognized by a specific binder (e.g., streptavidin). The specific binder may be linked to a solid phase thereby allowing the separation of the polypeptide conjugate from the helper molecule-second molecule complex through passage over a second helper-solid phase column which will retain, upon subsequent elution, the helper molecule-second molecule complex, but not the polypeptide conjugate. The polypeptide conjugate may be released from the helper molecule in any appropriate fashion. De-protection may be achieved by providing conditions in which the helper molecule dissociates from the functional site of the polypeptide to which it is bound; for instance, a complex between an antibody to which a polymer is conjugated and an anti-idiotypic antibody can be dissociated by adjusting the pH to an acid or alkaline pH.

In another aspect the oligoadenylate synthetase polypeptide is expressed as a fusion protein with a tag, i.e. an amino acid sequence or peptide made up of typically 1-30, such as 1-20 or 1-15 or 1-10 or 1-5 amino acid residues, e.g., added to the N-terminus or to the C-terminus of the polypeptide. Besides allowing for fast and easy purification, the tag is a convenient tool for achieving conjugation between the tagged polypeptide and the non-polypeptide moiety. In particular, the tag may be used for achieving conjugation in microtiter plates or other carriers, such as paramagnetic beads, to which the tagged polypeptide can be immobilised via the tag. The conjugation to the tagged polypeptide in, e.g., microtiter plates has the advantage that the tagged polypeptide can be immobilised in the microtiter plates directly from the culture broth (in principle without any purification) and subjected to conjugation. Thereby, the total number of process steps (from expression to conjugation) can be reduced. Furthermore, the tag may function as a spacer molecule ensuring an improved accessibility to the immobilised polypeptide to be conjugated. The conjugation using a tagged polypeptide may be to any of the non-polypeptide moieties disclosed herein, e.g. to a polymer molecule such as PEG.

The identity of the specific tag to be used is not critical as long as the tag is capable of being expressed with the polypeptide and is capable of being immunobilised on a suitable surface or carrier material. A number of suitable tags are commercially available, e.g. from Unizyme Laboratories, Denmark. Antibodies against such tags are commercially available, e.g. from ADI, Ayes Lab and Research Diagnostics.

The polypeptides of the invention include modified or mutant oligoadenylate synthetases with increased cell permeability, such increased cell permeability being affected by the addition of one or more basic amino acids residues (e.g., arginine, lysine, histidine), such as the addition of one basic residue, such as two basic residues, e.g., three basic residues, such as about four basic residues, e.g., five basic residues, such as about six basic residues, e.g., about 10 basic residues, e.g. 1-10 basic residues, such as about 5-10 basic residues, such as about 10-15 basic residues, e.g., 5-20 basic residues, said residues being added anywhere within the polypeptides of the invention, including but not limited to at the N-terminus or C-terminus.

Polynucleotides and Methods of Mutagenesis

The invention includes nucleic acids and polynucleotides that encode the polypeptides of the invention. The invention includes compositions produced by digesting one or more of any of the polynucleotides of the invention with a restriction endonuclease, an RNAse, or a DNAse (e.g., as is performed in certain of the recombination formats elsewhere in the specification); and compositions produced by fragmenting or shearing one or more polynucleotides of the invention by mechanical means (e.g., sonication, vortexing, and the like), which can also be used to provide substrates for recombination in the methods described herein. The invention also provides compositions produced by cleaving at least one of any of the polynucleotides of the invention. The cleaving may comprise mechanical, chemical, or enzymatic cleavage, and the enzymatic cleavage may comprise cleavage with a restriction endonuclease, an RNAse, or a DNAse.

Also included in the invention are compositions produced by a process comprising incubating one or more of the fragmented polynucleotides of the invention in the presence of ribonucleotide or deoxyribonucleotide triphosphates and a nucleic acid polymerase. This resulting composition forms a recombination mixture for many of the recombination formats noted above. The nucleic acid polymerase may be an RNA polymerase, a DNA polymerase, or an RNA-directed DNA polymerase (e.g., a "reverse transcriptase"); the polymerase can be, e.g., a thermostable DNA polymerase (e.g., VENT, TAQ, or the like).

Similarly, compositions comprising sets of oligonucleotides corresponding to more than one nucleic acids of the invention are useful as recombination substrates and are a feature of the invention. For convenience, these fragmented, sheared, or oligonucleotide synthesized mixtures are referred to as fragmented nucleic acid sets.

The invention also provides an isolated or recombinant nucleic acid encoding a polypeptide produced by mutating or recombining at least one polynucleotide of the invention.

Polynucleotides, oligonucleotides, and nucleic acid fragments of the invention can be prepared by standard solid-phase methods, according to known synthetic methods. Typically, fragments of up to about 100 bases are individually synthesized, then joined (e.g., by enzymatic or chemical ligation methods, or polymerase mediated recombination methods) to form essentially any desired continuous sequence. For example, the polynucleotides and oligonucleotides of the invention can be prepared by chemical synthesis using, e.g., classical phosphoramidite method described by, e.g., Beaucage et al. (1981) Tetrahedron Letters 22:1859-69, or the method described by Matthes et al. (1984) EMBO J. 3:801-05, e.g., as is typically practiced in automated synthetic methods. According to the phosphoramidite method, oligonucleotides are synthesized, e.g., in an automatic DNA synthesizer, purified, annealed, ligated and cloned into appropriate vectors.

In addition, essentially any polynucleotide can be custom ordered from any of a variety of commercial sources, such as Operon Technologies Inc. (Alameda, Calif.) and many others. Similarly, peptides and antibodies can be custom ordered from any of a variety of sources, e.g., Celtek Peptides (Nashville, Tenn.); Washington Biotechnology, Inc. (Baltimore Md.); Global Peptide Services (Ft. Collin Colo.), and many others.

Certain polynucleotides of the invention may also be obtained by screening cDNA libraries (e.g., libraries generated by recombining homologous nucleic acids as in typical recursive sequence recombination methods) using oligonucleotide probes that can hybridize to or PCR-amplify polynucleotides which encode OAS polypeptides and fragments of those polypeptides. Procedures for screening and isolating cDNA clones are well-known to those of skill in the art. Such techniques are described in, e.g., Berger and Kimmel, Guide to Molecular Cloning Techniques, Methods in Enzymol. Vol. 152, Acad. Press, Inc., San Diego, Calif. ("Berger"); J. Sambrook and D. W. Russell, Molecular Cloning: A Laboratory Manual, Third Edition. Cold Spring Harbor Press, Cold Spring Harbor, N.Y., ("Sambrook"); and F. M. Ausubel et al. (1987-2005) Current Protocols in Molecular Biology. Wiley Interscience, New York, N.Y. ("Ausubel"). Some polynucleotides of the invention can be obtained by altering a naturally occurring sequence, e.g., by mutagenesis, recursive sequence recombination (e.g., shuffling), or oligonucleotide recombination. In other cases, such polynucleotides can be made in silico or through oligonucleotide recombination methods as described in the references cited herein.

As described in more detail herein, the polynucleotides of the invention include polynucleotides that encode polypeptides of the invention, polynucleotide sequences complementary to these polynucleotide sequences, and polynucleotides that hybridize under at least stringent conditions to the sequences defined herein. A coding sequence refers to a polynucleotide sequence encoding a particular polypeptide or domain, region, or fragment of said polypeptide. The polynucleotides of the invention may be in the form of RNA or in the form of DNA, and include mRNA, cRNA, synthetic RNA and DNA, and cDNA. The polynucleotides may be double-stranded or single-stranded, and if single-stranded, can be the coding strand or the non-coding (anti-sense, complementary) strand. The polynucleotides of the invention include the coding sequence of a polypeptide of the invention (i) in isolation, (ii) in combination with one or more additional coding sequences, so as to encode, e.g., a fusion protein, a pre-protein, a prepro-protein, or the like, (iii) in combination with non-coding sequences, such as introns, control elements, such as a promoter (e.g., naturally occurring or recombinant or shuffled promoter), a terminator element, or 5' and/or 3' untranslated regions effective for expression of the coding sequence in a suitable host, and/or (iv) in a vector, cell, or host environment in which the coding sequence is a heterologous gene.

Polynucleotides of the invention can also be found in combination with typical compositional formulations of nucleic acids, including in the presence of carriers, buffers, adjuvants, excipients, and the like, as are known to those of ordinary skill in the art. Polynucleotide fragments typically comprise at least about 200 nucleotide bases, such as at least about 250, 300, 350, 400, 450, 460, 470, or more bases. The nucleotide fragments of polynucleotides of the invention may hybridize under highly stringent conditions to a polynucleotide sequence described herein and/or encode amino acid sequences having at least one of the properties of polypeptides of the invention described herein.

As will be understood by those of ordinary skill in the art, it can be advantageous to modify a coding sequence to enhance its expression in a particular host. The genetic code is redundant with 64 possible codons, but most organisms preferentially use a subset of these codons. The codons that are utilized most often in a species are considered optimal codons, and those not utilized very often are classified as rare or low-usage codons (see, e.g., Zhang, S. P. et al. (1991) Gene 105:61-72). Codons can be substituted to reflect the preferred codon usage of the host, a process sometimes termed "codon optimization" or "controlling for species codon bias."

Modified coding sequence containing codons preferred by a particular prokaryotic or eukaryotic host (see, e.g., Murray, E. et al. (1989) Nuc Acids Res 17:477-508; Griswold et al., (2003) Protein Expr. Purif. 27(1): 134-42) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA respectively. The preferred stop codon for monocotyledonous plants is UGA, whereas insects and *E. coli* prefer to use UAA as the stop codon (Dalphin, M. E. et al. (1996) Nucl. Acids Res. 24:216-218).

The polynucleotide sequences of the present invention can be engineered in order to alter a coding sequence of the invention for a variety of reasons, including but not limited to, alterations which modify the cloning, processing and/or expression of the gene product. For example, alterations may be introduced using techniques which are well known in the art, e.g., site-directed mutagenesis, to insert new restriction sites, to alter glycosylation patterns, to introduce or remove attachment groups (e.g., for pegylation or other conjugation), to change codon preference, to introduce splice sites, etc.

Because of the degeneracy of the genetic code, a large number of functionally identical nucleic acids encode any given polypeptide. For instance codons AGA, AGG, CGA, CGC, CGG, and CGU all encode the amino acid arginine. Thus, at every position in a nucleic acid sequence where an arginine is specified by a codon, the codon can be altered to any of the corresponding codons described above without altering the encoded polypeptide. Such nucleic acid variations are "silent variations". It is to be understood that U in an RNA sequence corresponds to T in a DNA sequence.

It will thus be appreciated by those skilled in the art that due to the degeneracy of the genetic code, a multitude of nucleic acids sequences encoding polypeptides of the invention may be produced, some of which may bear minimal sequence identity to the nucleic acid sequences explicitly disclosed herein. One of ordinary skill in the art will recognize that each codon in a nucleic acid (except AUG and UGC, which are ordinarily the only codon for methionine and tryptophan, respectively) can be modified by standard techniques to encode a functionally identical polypeptide. Accordingly, each silent variation of a nucleic acid which encodes a polypeptide is implicit in any described sequence. The invention also provides each and every possible variation of a nucleic acid sequence encoding a polypeptide of the invention that can be made by selecting combinations based on possible codon choices. These combinations are made in accordance with the standard triplet (codon) genetic code, as applied to the nucleic acid sequence encoding a polypeptide of the invention. All such variations of every nucleic acid herein are specifically provided and described by consideration of the sequence in combination with the genetic code. One of skill is fully able to generate any silent substitution of the sequences listed herein.

The polynucleotides of the invention have a variety of uses in, for example, recombinant production (i.e., expression) of the polypeptides of the invention typically through expression of a plasmid expression vector comprising a sequence encoding the polypeptide or fragment thereof; as therapeutics; as prophylactics; as diagnostic tools; as immunogens; as adjuvants; as diagnostic probes for the presence of complementary or partially complementary nucleic acids (including for detection of a wild-type oligoadenylate synthetase nucleic acid), as substrates for further reactions, e.g., recursive sequence recombination reactions or mutation reactions to produce new and/or improved variants, and the like.

Expression Vectors, Methods of Manufacturing, Gene Therapy

Recombinant methods for producing and isolating polypeptides of the invention are described herein. In addition to recombinant production, the polypeptides may be produced by direct peptide synthesis using solid-phase techniques (see, e.g., Stewart et al. (1969) Solid-Phase Peptide Synthesis, WH Freeman Co, San Francisco; Merrifield J. (1963) J Am Chem Soc 85:2149-2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. For example, subsequences may be chemically synthesized separately and combined using chemical methods to provide full-length polypeptides or fragments thereof. Alternatively, such sequences may be ordered from any number of companies which specialize in production of polypeptides. Most commonly, polypeptides of the invention may be produced by expressing coding nucleic acids and recovering polypeptides, e.g., as described below.

Methods for producing the polypeptides of the invention are also included. One such method comprises introducing into a population of cells any nucleic acid of the invention, which is operatively linked to a regulatory sequence effective to produce the encoded polypeptide, culturing the cells in a culture medium to express the polypeptide, and isolating the polypeptide from the cells or from the culture medium. An amount of nucleic acid sufficient to facilitate uptake by the cells (transfection) and/or expression of the polypeptide is utilized. The nucleic acid is introduced into such cells by any delivery method as is known in the art, including, e.g., injection, gene gun, passive uptake, etc. As one skilled in the art will recognize, the nucleic acid may be part of a vector, such as a recombinant expression vector, including a DNA plasmid vector, or any vector as known in the art.

The nucleic acid or vector comprising a nucleic acid of the invention may be prepared and formulated by standard recombinant DNA technologies and isolation methods as known in the art. Such a nucleic acid or expression vector may be introduced into a population of cells of a mammal in vivo, or selected cells of the mammal (e.g., tumor cells) may be removed from the mammal and the nucleic acid expression vector introduced ex vivo into the population of such cells in an amount sufficient such that uptake and expression of the encoded polypeptide results. Or, a nucleic acid or vector comprising a nucleic acid of the invention is produced using cultured cells in vitro. In one aspect, the method of producing a polypeptide of the invention comprises introducing into a population of cells a recombinant expression vector comprising any nucleic acid of the invention described herein in an amount and formula such that uptake of the vector and expression of the encoded polypeptide will result; administering the expression vector into a mammal by any introduction/delivery format described herein; and isolating the polypeptide from the mammal or from a byproduct of the mammal.

The invention provides isolated or recombinant nucleic acids (also referred to herein as polynucleotides), collectively referred to as "nucleic acids (or polynucleotides) of the invention", which encode polypeptides of the invention. The polynucleotides of the invention are useful in a variety of applications. As discussed above, the polynucleotides are useful in producing polypeptides of the invention. In addition, polynucleotides of the invention can be incorporated into expression vectors useful for gene therapy, DNA vaccination, and immunotherapy, as described elsewhere in this application.

Any of the polynucleotides of the invention (which includes those described above) may encode a fusion protein comprising at least one additional amino acid sequence, such as, for example, a secretion/localization sequence, a sequence useful for solubilization or immobilization (e.g., for cell surface display) of the polypeptide, a sequence useful for detection and/or purification of the polypeptide (e.g., a polypeptide purification subsequence, such as an epitope tag, a polyhistidine sequence, and the like). In another aspect, the invention provides cells comprising one or more of the polynucleotides of the invention. Such cells may express one or more polypeptides encoded by the polynucleotides of the invention.

The invention also provides vectors comprising any of the polynucleotides of the invention. Such vectors may comprise a plasmid, a cosmid, a phage, a virus, or a fragment of a virus. Such vectors may comprise an expression vector, and, if desired, the nucleic acid is operably linked to a promoter, including those discussed herein and below. Furthermore, in another aspect, the invention provides compositions comprising an excipient or carrier and at least one of any of the polynucleotides of the invention, or vectors, cells, or host comprising such nucleic acids. Such composition may be pharmaceutical compositions, and the excipient or carrier may be a pharmaceutically acceptable excipient or carrier.

The invention also includes compositions comprising two or more nucleic acids of the invention, or fragments thereof (e.g., as substrates for recombination). The composition can comprise a library of recombinant nucleic acids, where the library contains at least 2, at least 3, at least 5, at least 10, at least 20, at least 50, or at least 100 or more nucleic acids described above. The nucleic acids are optionally cloned into expression vectors, providing expression libraries.

The polynucleotides of the invention and fragments thereof, as well as vectors comprising such polynucleotides, may be employed for therapeutic or prophylactic uses in combination with a suitable carrier, such as a pharmaceutical carrier. Such compositions comprise a therapeutically and/or prophylactically effective amount of the compound, and a pharmaceutically acceptable carrier or excipient. Such a carrier or excipient includes, but is not limited to, saline, buffered saline, dextrose, water, glycerol, ethanol, and combinations thereof. The formulation should suit the mode of administration. Methods of administering nucleic acids, polypeptides, and proteins are well known in the art.

The present invention also includes recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), and the like, into which a nucleic acid sequence of the invention has been inserted, in a forward or reverse orientation. In some instances, the construct further comprises regulatory sequences, including, for example, a promoter, operably linked to the nucleic acid sequence. Large numbers of suitable vectors and promoters are known to those of skill in the art, and are commercially available.

General texts that describe molecular biological techniques useful herein, including the use of vectors, promoters and many other relevant topics, include Berger, supra; Sambrook (1989), supra, and Ausubel, supra. Examples of techniques sufficient to direct persons of skill through in vitro amplification methods, including the polymerase chain reaction (PCR) the ligase chain reaction (LCR), Q beta-replicase amplification and other RNA polymerase mediated techniques (e.g., NASBA), e.g., for the production of the homologous nucleic acids of the invention are found in Berger, Sambrook, and Ausubel, all supra, as well as Mullis et al. (1987) U.S. Pat. No. 4,683,202; PCR Protocols: A Guide to Methods and Applications (Innis et al., eds.) Academic Press Inc. San Diego, Calif. (1990) ("Innis"); Arnheim & Levinson (Oct. 1, 1990) C&EN 36-47; The Journal Of NIH Research (1991) 3:81-94; (Kwoh et al. (1989) Proc Natl Acad Sci USA 86:1173-1177; Guatelli et al. (1990) Proc Natl Acad Sci USA 87:1874-1878; Lomeli et al. (1989) J Clin Chem 35:1826-1831; Landegren et al. (1988) Science 241:1077-1080; Van Brunt (1990) Biotechnology 8:291-294; Wu and Wallace (1989) Gene 4:560-569; Barringer et al. (1990) Gene 89:117-122, and Sooknanan and Malek (1995) Biotechnology 13:563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369:684-685 and the references therein, in which PCR amplicons of up to 40 kilobases (kb) are generated. One of skill will appreciate that essentially any RNA can be converted into a double stranded DNA suitable for restriction digestion, PCR expansion and sequencing using reverse transcriptase and a polymerase. See Ausubel, Sambrook and Berger, all supra.

The present invention also provides host cells that are transduced with vectors of the invention, and the production of polypeptides of the invention by recombinant techniques. Host cells are genetically engineered (e.g., transduced, transformed or transfected) with the vectors of this invention, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying genes. The culture conditions, such as temperature, pH, and the like, are those previously used with the host cell selected for expression, and will be apparent to those skilled in the art and in the references cited herein, including, e.g., Freshney (1994) Culture of Animal Cells, a Manual of Basic Technique, third edition, Wiley-Liss, New York and the references cited therein.

The polypeptides of the invention can also be produced in non-animal cells such as plants, yeast, fungi, bacteria and the like. In addition to Sambrook, Berger and Ausubel, details regarding cell culture are found in, e.g., Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York); Atlas & Parks (eds.) The Handbook of Microbiological Media (1993) CRC Press, Boca Raton, Fla.

The polynucleotides of the present invention and fragments thereof may be included in any one of a variety of expression vectors for expressing a polypeptide. Such vectors include chromosomal, nonchromosomal and synthetic DNA sequences, e.g., derivatives of SV40, bacterial plasmids, phage DNA, baculovirus, yeast plasmids, vectors derived from combinations of plasmids and phage DNA, viral DNA such as vaccinia, adenovirus, fowl pox virus, pseudorabies, adeno-associated virus, retroviruses and many others. Any vector that transduces genetic material into a cell, and, if replication is desired, which is replicable and viable in the relevant host can be used.

The nucleic acid sequence in the expression vector is operatively linked to an appropriate transcription control sequence (promoter) to direct mRNA synthesis. Examples of such promoters include: LTR or SV40 promoter, E. coli lac or trp promoter, phage lambda PL promoter, CMV promoter, and other promoters known to control expression of genes in prokaryotic or eukaryotic cells or their viruses. The expression vector also contains a ribosome binding site for translation initiation, and a transcription terminator. The vector optionally includes appropriate sequences for amplifying expression, e.g., an enhancer. In addition, the expression vectors optionally comprise one or more selectable marker genes to provide a phenotypic trait for selection of transformed host cells, such as dihydrofolate reductase or neomycin resistance for eukaryotic cell culture, or such as tetracycline, kanamycin or ampicillin resistance in E. coli.

The vector containing the appropriate DNA sequence encoding a polypeptide of the invention, as well as an appropriate promoter or control sequence, may be employed to transform an appropriate host to permit the host to express the polypeptide. Examples of appropriate expression hosts include: bacterial cells, such as E. coli, Streptomyces, and Salmonella typhimurium; fungal cells, such as Saccharomyces cerevisiae, Pichia pastoris, and Neurospora crassa; insect cells such as Drosophila and Spodoptera frugiperda; mammalian cells such as CHO, COS, BHK, HEK 293 or Bowes melanoma; plant cells, etc. It is understood that not all cells or cell lines need to be capable of producing fully functional polypeptides of the invention or fragments thereof; for example, antigenic fragments of the polypeptide may be produced in a bacterial or other expression system. The invention is not limited by the host cells employed.

In bacterial systems, a number of expression vectors may be selected depending upon the use intended for the polypeptide or fragment thereof. For example, when large quantities of a polypeptide or fragments thereof are needed for the induction of antibodies, vectors which direct high level expression of fusion proteins that are readily purified may be desirable. Such vectors include, but are not limited to, multifunctional E. coli cloning and expression vectors such as BLUESCRIPT (Stratagene), in which the nucleotide coding sequence may be ligated into the vector in-frame with sequences for the amino-terminal Met and the subsequent 7 residues of beta-galactosidase so that a hybrid protein is produced; pIN vectors (Van Heeke & Schuster (1989) J Biol Chem 264:5503-5509); pET vectors (Novagen, Madison Wis.); and the like.

Similarly, in the yeast Saccharomyces cerevisiae a number of vectors containing constitutive or inducible promoters such as alpha factor, alcohol oxidase and PGH may be used for production of the polypeptides of the invention. For reviews, see Ausubel, supra, Berger, supra, and Grant et al. (1987) Methods in Enzymology 153:516-544.

In mammalian host cells, a number of expression systems, such as viral-based systems, may be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome results in a viable virus capable of expressing a polypeptide of the invention in infected host cells (Logan and Shenk (1984) Proc Natl Acad Sci USA 81:3655-3659). In addition, transcription enhancers, such as the rous sarcoma virus (RSV) enhancer, are used to increase expression in mammalian host cells. Host cells, media, expression systems, and methods of production include those known for cloning and expression of various mammalian proteins.

Specific initiation signals can aid in efficient translation of a polynucleotide coding sequence of the invention and/or fragments thereof. These signals can include, e.g., the ATG initiation codon and adjacent sequences. In cases where a coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous nucleic acid transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression can be enhanced by the inclusion of enhancers appropriate to the cell system in use (see, e.g., Scharf D. et al. (1994) Results Probl Cell Differ 20:125-62; and Bittner et al. (1987) Methods in Enzymol 153:516-544).

Polynucleotides encoding polypeptides of the invention can also be fused, for example, in-frame to nucleic acids encoding a secretion/localization sequence, to target polypeptide expression to a desired cellular compartment, membrane, or organelle, or to direct polypeptide secretion to the periplasmic space or into the cell culture media. Such sequences are known to those of skill, and include secretion leader or signal peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

In a further aspect, the present invention relates to host cells containing any of the above-described nucleic acids, vectors, or other constructs of the invention. The host cell can be a eukaryotic cell, such as a mammalian cell, a yeast cell, or a plant cell, or the host cell can be a prokaryotic cell, such as a bacterial cell. Introduction of the construct into the host cell can be effected by calcium phosphate transfection, DEAE-Dextran mediated transfection, electroporation, gene or vaccine gun, injection, or other common techniques (see, e.g., Davis, L., Dibner, M., and Battey, I. (1986) Basic Methods in Molecular Biology) for in vivo, ex vivo or in vitro methods.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "pre" or a "prepro" form of the protein may also be important for correct insertion, folding and/or function. Different host cells such as E. coli, Bacillus sp., yeast or mammalian cells such as CHO, HeLa, BHK, MDCK, HEK 293, W138, etc. have specific cellular machinery and characteristic mechanisms for such post-translational activities and may be chosen to ensure the correct modification and processing of the introduced foreign protein.

Stable expression can be used for long-term, high-yield production of recombinant proteins. For example, cell lines which stably express a polypeptide of the invention are transduced using expression vectors which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. For example, resistant clumps of stably transformed cells can be proliferated using tissue culture techniques appropriate to the cell type.

Host cells transformed with a nucleotide sequence encoding a polypeptide of the invention are optionally cultured under conditions suitable for the expression and recovery of the encoded protein from cell culture. The polypeptide produced by a recombinant cell may be secreted, membrane-bound, or contained intracellularly, depending on the sequence and/or the vector used. As will be understood by those of skill in the art, expression vectors containing polynucleotides encoding polypeptides of the invention can be designed with signal sequences which direct secretion of the mature polypeptides through a prokaryotic or eukaryotic cell membrane.

The polynucleotides of the present invention optionally comprise a coding sequence fused in-frame to a marker sequence which, e.g., facilitates purification and/or detection of the encoded polypeptide. Such purification subsequences include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson, I. et al. (1984) Cell 37:767), maltose binding protein sequences, the FLAG epitope utilized in the FLAGS extension/affinity purification system, and the like. The inclusion of a protease-cleavable polypeptide linker sequence between the purification domain and the polypeptide sequence is useful to facilitate purification.

For example, one expression vector possible to use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al. (1992) Protein Expression and Purification 3:263-281) while the enterokinase cleavage site provides a method for separating the desired polypeptide from the polyhistidine region. pGEX vectors (Promega; Madison, Wis.) are optionally used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

An additional construction in the compositions and methods described herein provides for proteins, and their encoding nucleic acids, comprising polypeptides of the invention (or one or more fragments thereof), e.g., as described herein, fused to an Ig molecule, e.g., human IgG Fc ("fragment crystallizable," or fragment complement binding) hinge, CH2 domain and CH3 domain (and nucleotide sequences encoding them). Fc is the portion of the antibody responsible for binding to antibody receptors on cells and the Clq component of complement. These fusion proteins or fragments thereof and their encoding nucleic acids are optionally useful as prophylactic and/or therapeutic drugs or as diagnostic tools (see also, e.g., Challita-Eid, P. et al. (1998) J Immunol 160: 3419-3426; Sturmhoefel, K. et al. (1999) Cancer Res 59:4964-4972).

Following transduction of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Eukaryotic or microbial cells employed in expression of the proteins can be disrupted by any convenient method, including freeze-thaw cycling, sonication, mechanical disruption, or use of cell lysing agents, or other methods, which are well know to those skilled in the art.

As noted, many references are available for the culture and production of many cells, including cells of bacterial, plant, animal (especially mammalian) and archebacterial origin. See, e.g., Sambrook, Ausubel, and Berger (all supra), as well as Freshney (1994) Culture of Animal Cells, a Manual of Basic Technique, third edition, Wiley-Liss, New York and the references cited therein; Doyle and Griffiths (1997) Mammalian Cell Culture: Essential Techniques John Wiley and Sons, New York; Humason (1979) Animal Tissue Techniques, fourth edition W.H. Freeman and Company; and Ricciardelli et al. (1989) In vitro Cell Dev Biol 25:1016-1024. For plant cell culture and regeneration see, e.g., Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York) and Plant Molecular Biology (1993) R. R. D. Croy (ed.) Bios Scientific Publishers, Oxford, U.K. ISBN 0 12 198370 6. Cell culture media in general are set forth in Atlas and Parks (eds.) The Handbook of Microbiological Media (1993) CRC Press, Boca Raton, Fla. Additional information for cell culture is found in available commercial literature such as the Life Science Research Cell Culture Catalogue from Sigma-Aldrich, Inc (St Louis, Mo.) ("Sigma-LSRCCC") and, e.g., the Plant Culture Catalogue and supplement also from Sigma-Aldrich, Inc (St Louis, Mo.) ("Sigma-PCCS"). Polypeptides of the invention can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein or fragments thereof. Finally, high performance liquid chromatography (HPLC) can be employed in the final purification steps. In addition to the references noted, supra, a variety of purification methods are well known in the art, including, e.g., those set forth in Sandana (1997) Bioseparation of Proteins, Academic Press, Inc.; Bollag et al. (1996) Protein Methods, 2.sup.nd Edition Wiley-Liss, New York; Walker (1996) The Protein Protocols Handbook Humana Press, New Jersey; Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3.sup.rd Edition Springer Verlag, New York; Janson and Ryden (1998) Protein Purification: Principles, High Resolution Methods and Applications, Second Edition Wiley-VCH, New York; and Walker (1998) Protein Protocols on CD-ROM Humana Press, New Jersey.

Cell-free transcription/translation systems can also be employed to produce polypeptides of the invention using polynucleotides of the present invention. Several such systems are commercially available. A general guide to in vitro transcription and translation protocols is found in Tymms (1995) In vitro Transcription and Translation Protocols: Methods in Molecular Biology Volume 37, Garland Publishing, New York.

Polynucleotides that encode a polypeptide of the invention, or complements of the polynucleotides (including e.g., antisense or ribozyme molecules), are optionally administered to a cell to accomplish a therapeutically useful process or to express a therapeutically useful product. These in vivo applications, including gene therapy, include a multitude of techniques by which gene expression may be altered in cells. Such methods include, for instance, the introduction of genes for expression of, e.g., therapeutically and/or prophylactically useful polypeptides, such as the polypeptides of the present invention.

Polynucleotides encoding polypeptides of the invention are particularly useful for in vivo therapeutic applications, using techniques well known to those skilled in the art. For example, cultured cells are engineered ex vivo with at least one polynucleotide (DNA or RNA) of the invention and/or other polynucleotide sequences encoding, e.g., at least one of an antigen, cytokine, other co-stimulatory molecule, adjuvant, etc., and the like, with the engineered cells then being returned to the patient. Cells may also be engineered in vivo for expression of one or more polypeptides in vivo, including polypeptides and/or antigenic peptides of the invention.

A number of viral vectors suitable for organismal in vivo transduction and expression are known. Such vectors include retroviral vectors (see, e.g., Miller, Curr Top Microbiol Immunol (1992) 158:1-24; Salmons and Gunzburg (1993) Human Gene Therapy 4:129-141; Miller et al. (1994) Methods in Enzymology 217:581-599) and adeno-associated vectors (reviewed in Carter (1992) Curr Opinion Biotech 3:533-539; Muzcyzka (1992) Curr Top Microbiol Immunol. 158: 97-129). Other viral vectors that are used include adenoviral vectors, herpes viral vectors and Sindbis viral vectors, as generally described in, e.g., Jolly (1994) Cancer Gene Therapy 1:51-64; Latchman (1994) Molec Biotechnol 2:179-195; and Johanning et al. (1995) Nucl Acids Res 23:1495-1501.

In one aspect, a pox virus vector can be used. The pox viral vector is transfected with a polynucleotide sequence encoding a polypeptide of the invention and is useful in prophylactic, therapeutic and diagnostic applications where enhancement of an immune response, such as e.g., increased or improved T cell proliferation is desired. See viral vectors discussed in, e.g., Berencsi et al., J Infect Dis (2001)183(8): 1171-9; Rosenwirth et al., Vaccine 2001 Feb. 8; 19(13-14): 1661-70; Kittlesen et al., J Immunol (2000) 164(8):4204-11; Brown et al. Gene Ther 2000 7(19):1680-9; Kanesa-thasan et al., Vaccine (2000) 19(4-5):483-91; Sten (2000) Drug 60(2): 249-71. Compositions comprising such vectors and an acceptable excipient are also a feature of the invention.

Gene therapy and genetic vaccines provide methods for combating chronic infectious diseases (e.g., HIV infection, viral hepatitis), as well as non-infectious diseases including cancer and some forms of congenital defects such as enzyme deficiencies, and such methods can be employed with polynucleotides of the invention, including, e.g., vectors and cells comprising such polynucleotides. Several approaches for introducing nucleic acids and vectors into cells in vivo, ex vivo and in vitro have been used and can be employed with polynucleotides of the invention, and vectors comprising such polynucleotides. These approaches include liposome based gene delivery (Debs and Zhu (1993) WO 93/24640 and U.S. Pat. No. 5,641,662; Mannino and Gould-Fogerite (1988) BioTechniques 6(7):682-691; Rose, U.S. Pat. No. 5,279,833; Brigham (1991) WO 91/06309; and Feigner et al. (1987) Proc Natl Acad Sci USA 84:7413-7414; Brigham et al. (1989) Am J Med Sci 298:278-281; Nabel et al. (1990) Science 249:1285-1288; Hazinski et al. (1991) Am J Resp Cell Molec Biol 4:206-209; and Wang and Huang (1987) Proc Natl Acad Sci USA 84:7851-7855); adenoviral vector mediated gene delivery, e.g., to treat cancer (see, e.g., Chen et al. (1994) Proc Natl Acad Sci USA 91:3054-3057; Tong et al. (1996) Gynecol Oncol 61:175-179; Clayman et al. (1995) Cancer Res. 5:1-6; O'Malley et al. (1995) Cancer Res 55:1080-1085; Hwang et al. (1995) Am J Respir Cell Mol Biol 13:7-16; Haddada et al. (1995) Curr Top Microbiol Immunol. 1995 (Pt. 3):297-306; Addison et al. (1995) Proc Natl Acad Sci USA 92:8522-8526; Colak et al. (1995) Brain Res 691:76-82; Crystal (1995) Science 270:404-410; Elshami et al. (1996) Human Gene Ther 7:141-148; Vincent et al. (1996) J Neurosurg 85:648-654), and many others. Replication-defective retroviral vectors harboring therapeutic polynucleotide sequence as part of the retroviral genome have also been used, particularly with regard to simple MuLV vectors. See, e.g., Miller et al. (1990) Mol Cell Biol 10:4239 (1990); Kolberg (1992) J NIH Res 4:43, and Cornetta et al. (1991) Hum Gene Ther 2:215). Nucleic acid transport coupled to ligand-specific, cation-based transport systems (Wu and Wu (1988) J Biol Chem, 263:14621-14624) has also been used. Naked DNA expression vectors have also been described (Nabel et al. (1990), supra); Wolff et al. (1990) Science, 247:1465-1468). In general, these approaches can be adapted to the invention by incorporating nucleic acids encoding the polypeptides of the invention into the appropriate vectors.

General texts which describe gene therapy protocols, which can be adapted to the present invention by introducing the nucleic acids of the invention into patients, include, e.g., Robbins (1996) Gene Therapy Protocols, Humana Press, New Jersey, and Joyner (1993) Gene Targeting: A Practical Approach, IRL Press, Oxford, England.

Antiviral Treatments

The polynucleotides and polypeptides of the invention may be used therapeutically or prophylactically to treat or prevent virus infection. Exemplary viruses include, but are not limited to, viruses of the Flaviviridae family, such as, for example, Hepatitis C Virus, Yellow Fever Virus, West Nile Virus, Japanese Encephalitis Virus, Dengue Virus, and Bovine Viral Diarrhea Virus; viruses of the Hepadnaviridae family, such as, for example, Hepatitis B Virus; viruses of the Picornaviridae family, such as, for example, Encephalomyocarditis Virus, Human Rhinovirus, and Hepatitis A Virus; viruses of the Retroviridae family, such as, for example, Human Immunodeficiency Virus, Simian Immunodeficiency Virus, Human T-Lymphotropic Virus, and Rous Sarcoma Virus; viruses of the Coronaviridae family, such as, for example, SARS coronavirus; viruses of the Rhabdoviridae family, such as, for example, Rabies Virus and Vesicular Stomatitis Virus, viruses of the Paramyxoviridae family, such as, for example, Respiratory Syncytial Virus and Parainfluenza Virus, viruses of the Papillomaviridae family, such as, for example, Human Papillomavirus, and viruses of the Herpesviridae family, such as, for example, Herpes Simplex Virus.

It is another object of the invention to provide conjugates, such conjugates comprising one or more non-polypeptide moiety linked to a polypeptide of the invention, which conjugate exhibits an antiviral property, and which optionally exhibits other desirable properties, such as increased serum half-life and/or functional in vivo half-life, and/or decreased antigenicity, compared to the non-conjugated polypeptide. Some such conjugates may exhibit enhanced efficacy in clearing a virus from cells infected with the virus, compared to a reference oligoadenylate synthetase. Some such conjugates may further have reduced toxicity compared to a reference oligoadenylate synthetase.

It is another object of the invention to provide a method of inhibiting viral replication in virus-infected cells, the method comprising administering to the virus-infected cells a polypeptide or conjugate of the invention in an amount effective to inhibit viral replication in said cells. The invention also provides a method of reducing the number of copies of a virus in virus-infected cells, comprising administering to the virus-infected cells a polypeptide or conjugate of the invention in an amount effective to reduce the number of copies of the virus in said cells. The cells may be in culture or otherwise isolated from a mammal (i.e., in vitro or ex vivo), or may be in vivo, e.g., in a subject, in a mammal, in a primate, or in man.

Anticancer and Inflammation Treatments

It has been demonstrated that the polypeptides of the invention can cause certain cell types and cell lines to undergo apoptosis or to affect growth retardation of said cell lines or cell types. Such cell lines or cell types include in an exemplary embodiment those derived from the prostate and breast.

The invention provides a method of inhibiting proliferation of a cell population, comprising contacting the cell population with a polypeptide of the invention in an amount effective to decrease proliferation of the cell population. The cell population may be in culture or otherwise isolated from a mammal (i.e., in vitro or ex vivo), or may be in vivo, e.g., in a subject, in a mammal, a primate, or man.

The invention provides for treating cancers and neoplastic diseases using the polypeptides and polynucleotides of the invention. Exemplary cancers and neoplastic diseases include but are not limited to: adrenocortical carcinoma, AIDS related cancers, such as for example, Kaposi's sarcoma, AIDS-related lymphoma, anal cancer, astrocytoma, basal cell carcinoma, bile duct cancers, such as for example those of an extrahepatic nature, bladder cancer, bone cancers, such as for example osteosarcomas and malignant fibrous histiocytomas, brain stem glioma, brain tumors, such as for example gliomas, astrocytomas, malignant gliomas, ependymomas, medulloblastomas, and neuroblastomas, supratentorial primitive neuroectodermal tumor, visual pathway and hypothalamic glioma, breast cancer, bronchial adenoma, Burkitt's lymphoma, carcinoid tumors, central nervous system lymphoma, cervical cancer, leukemias, such as for example, hairy cell leukemia, acute lymphoblastic leukemia, acute myeloid leukemia, chronic lymphocytic leukemia and chronic myelogenous leukemia, chronic myeloproliferative disorders, colorectal cancer, cutaneous T-cell lymphoma, endometrial cancer, esophageal cancer, Ewing's family of tumors, extracranial germ cell tumor, extragonadal germ cell tumor, eye cancers, such as for example, intraocular melanoma and retinoblastoma, gallbladder cancer, stomach cancer, gestational trophoblastic tumor, head and neck cancer, hepatocellular carcinoma, Hodgkin's lymphoma, Non-Hodgkin's lymphoma, primary CNS lymphoma, nasopharyngeal cancer, islet cell carcinoma, kidney (renal cell) cancer, laryngeal cancer, lip and oral cancer, liver cancer, lung cancer, such as for example non-small cell and small cell lung cancers, Waldenstrom's macroglobulinemia, Merkel cell carcinoma, mesothelioma, metastatic squamous neck cancer, multiple endocrine neoplasia, multiple myeloma, plasma cell neoplasm, mycosis fungoides, myelodysplastic syndromes, myeloproliferative diseases, nasal cavity and paranasal sinus cancer, ovarian cancer, such as germ cell and epithelial, low-malignant potential ovarian tumor, pancreatic cancer, parathyroid cancer, penile cancer, pheochromocytoma, pituitary tumor, pleuropulmonary blastoma, prostate cancer, rhabdomyosarcoma, salivary gland cancer, sarcomas, Sezary syndrome, skin cancer, such as for example melanoma and squamous cell carcinoma, testicular cancer, thymoma, thymic carcinoma, thyroid cancer, transitional cell cancer, trophoblastic tumor, urethral cancer, uterine cancer, vaginal cancer, vulvar cancer, and Wilms' tumor.

The invention further provides for treating autoimmune diseases and inflammation using the polypeptides and polynucleotides of the invention, said autoimmune and inflammatory diseases include but are not limited to: asthma, Crohn's disease, Guillain-Barre syndrome, multiple sclerosis, myasthenia gravis, optic neuritis, psoriasis, rheumatoid arthritis, Grave's disease, Hashimoto's (thyroiditis) disease, Ord's thyroiditis, diabetes, diabetes mellitus, Reiter's syndrome, autoimmune hepatitis, primary biliary cirrhosis, liver cirrhosis, liver fibrosis, antiphospholipd antibody syndrome, opsoclonus myoclonus syndrome, temporal arteritis, acute disseminated encephalomyelitis, Goodpasture's syndrome, Wegener's granulomatosis, coeliac disease, pemphigus, polyarthritis, warm autoimmune hemolytic anemia, Takayasu's arteritis, coronary artery disease, endometriosis, interstitial cystitis, neuromyotonia, scleroderma, vitiligo, vulvodynia, Chagas' disease, sarcoidosis, chronic fatigue syndrome, acute respiratory distress syndrome, tendonitis, bursitis, polymyalgia rheumatica, inflammatory bowel disease, chronic obstructive pulmonary disease, allergic rhinitis, cardiovascular disease, chronic cholecystitis, bronchiectasis, pneumoconiosis, such as for example, silicosis, osteoarthritis, atherosclerosis, dysautonomia, ankylosing spondylitis, acute anterior uveitis, systemic lupus erythematosus, insulin-dependent diabetes mellitus, pemphigus vulgaris, experimental allergic encephalomyelitis, experimental autoimmune uveorenitis, mixed connective tissue disease, Sjørgen's syndrome, autoimmune hemolytic anemia, autoimmune thrombocytopenic purpura, acute rheumatic fever, mixed essential cryoglobulinemia, juvenile rheumatoid arthritis, degenerative joint disease, ankylosing spondylitis, psoriatic arthritis, neuralgia, synoviitis, glomerulonephritis, vasculitis, inflammations that occur as sequellae to influenza, the common cold and other viral infections, gout, contact dermatitis, low back and neck pain, dysmenorrhea, headache, toothache, sprains, strains, myositis, burns, injuries, and pain and inflammation that follow surgical and dental procedures in a subject.

Cell Growth and Tissue Regeneration Treatments

The polypeptides of the invention have been shown to stimulate a mitogenic, cell growth-promoting program in specific cell types and cell lines, such as for example, Huh7 hepatoma cells and MRC5 fetal lung fibroblast cells. This mitogenic program is identified using expression microarray analysis and cell viability assays of cells and cell lines treated with the polypeptides of the invention. The invention provides for uses of the polypeptides of the invention to stimulate cell growth and tissue regeneration in vitro, in vivo, and ex vivo using tissues and cells derived from subjects or mammals.

Derivatives of the Polypeptides of the Invention

The invention provides for polypeptides that differ from the polypeptides of FIG. 1 by 1 to 34 amino acids, such differences may include substitutions, insertions, deletions, the incorporation of modified amino acids or amino acid derivatives, and the addition or deletion of amino acids from the C-terminus or N-terminus of the polypeptides. One or more amino acid substitutions may be made to the polypeptides of the invention according to, for example, a substitution group (such as, a conservative substitution group), such as one set forth below. Alternatively, or in addition, one or more amino acid substitutions may made in the polypeptides which introduces or removes an amino acid residue comprising an attachment group for a non-polypeptide moiety. Examples include introduction of one or more N-glycosylation site(s), introduction of one or more cysteine residue(s) or lysine residue(s), removal of one or more N-glycosylation site(s), and/or or removal of one or more lysine(s) or histidine(s). Some such polypeptides exhibit an oligoadenylate synthetase activity. Conservative substitutions groups include: Group 1, Alanine (A) Glycine (G) Serine (S) Threonine (T), Group 2, Aspartic acid (D) Glutamic acid (E), Group 3, Asparagine (N) Glutamine (Q), Group 4, Arginine (R) Lysine (K) Histidine (H), Group 5, Isoleucine (I) Leucine (L) Methionine (M) Valine (V), and Group 6, Phenylalanine (F) Tyrosine (Y) Tryptophan (W). Other substitution groups of amino acids can be envisioned. For example, amino acids can be grouped by similar function or chemical structure or composition (e.g., acidic, basic, aliphatic, aromatic, sulfur-containing). For example, an Aliphatic grouping may comprise: Glycine (G), Alanine (A), Valine (V), Leucine (L), Isoleucine (I). Other groups containing amino acids that are considered conservative substitutions for one another include: Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also Creighton (1984) Proteins, W.H. Freeman and Company, for additional groupings of amino acids. Listing of a polypeptide sequence herein, in conjunction with the above substitution groups, provides an express listing of all conservatively substituted polypeptide sequences.

In one aspect, the invention provides isolated or recombinant polypeptides each comprising a sequence having at least 90% sequence identity (e.g., at least about 91%, at least about 92%, at least about 93%, at least about 94%, at least about 95%, at least about 96%, at least about 97%, at least about 98%, or at least about 99% amino acid sequence identity) to any one of the polypeptides of FIG. 1. In some instances the polypeptide exhibits oligoadenylate synthetase activity.

The degree to which a sequence (polypeptide or nucleic acid) is similar to another provides an indication of similar structural and functional properties for the two sequences. Accordingly, in the context of the present invention, sequences which have a similar sequence to any given exemplar sequence are a feature of the present invention. In particular, sequences that have percent sequence identities as defined below are a feature of the invention. A variety of methods of determining sequence relationships can be used, including manual alignment and computer assisted sequence alignment and analysis. A variety of computer programs for performing sequence alignments are available, or an alignment can be prepared manually by one of skill.

As noted above, the sequences of the polypeptides and nucleic acids employed in the subject invention need not be identical, but can be substantially identical to the corresponding sequence of a polypeptide of the invention or nucleic acid of the invention. For example, polypeptides of the invention can be subject to various changes, such as one or more amino acid insertions, deletions, and/or substitutions, either conservative or non-conservative, including where, e.g., such changes might provide for certain advantages in their use, such as, in their therapeutic or prophylactic use or administration or diagnostic application. The nucleic acids of the invention can also be subject to various changes, such as one or more substitutions of one or more nucleic acids in one or more codons such that a particular codon encodes the same or a different amino acid, resulting in either a silent variation (as defined herein) or non-silent variation, or one or more deletions of one or more nucleic acids (or codons) in the sequence. The nucleic acids can also be modified to include one or more codons that provide for optimum expression in an expression system (e.g., bacterial or mammalian), while, if desired, said one or more codons still encode the same amino acid(s). Such nucleic acid changes might provide for certain advantages in their therapeutic or prophylactic use or administration, or diagnostic application. The nucleic acids and polypeptides can be modified in a number of ways so long as they comprise a sequence substantially identical (as defined below) to a sequence in a respective nucleic acid or polypeptide of the invention.

The term "identical" or "identity," in the context of two or more nucleic acid or polypeptide sequences, refers to two or more sequences that are the same or have a specified percentage of amino acid residues or nucleotides that are the same, when compared and aligned for maximum similarity, as determined using a sequence comparison algorithm or by visual inspection.

The "percent sequence identity" ("% identity") of a subject sequence to a reference (i.e. query) sequence means that the subject sequence is identical (i.e., on an amino acid-by-amino acid basis for a polypeptide sequence, or a nucleotide-by-nucleotide basis for a polynucleotide sequence) by a specified percentage to the query sequence over a comparison length.

Site Directed Mutagenesis to Create the Polypeptides of the Invention

The polypeptides of the present invention can be engineered using any standard method of site-directed mutagenesis. The nucleic acid sequences corresponding to the polypeptides of the invention are synthetized using specific oligonucleotide primers and a high fidelity DNA polymerase. The target sequence is contained on a double stranded plasmid isolated from a methylation-competent *E. coli* strain. Complimentary oligonucleotides containing the desired mutation are synthesized and purified using polyacrylamide gel electrophoresis. A thermal cycler is used to control the temperature for alternating cycles of denaturation of the double stranded plasmid template (94° C. for 30 seconds), annealing of the oligonucleotide primers (55° C. for 1 minute), and extension of the primers with a high fidelity polymerase (68° C. for 1 minute/kb of plasmid length). After approximately 15 cycles, the mixture of newly synthetized and input DNA are treated with a restriction enzyme specific for methylated residues (Dpn I) to digest the parental plasmid. The resulting DNA is introduced into chemically or electrically competent bacterial strains for screening and isolation of plasmids containing the desired mutation. Plasmid DNA is isolated from the transformants and screened via fluorescent dye-terminator sequencing to confirm the mutant sequence.

Bulk Drug Product Expression, Fermentation, and Purification

An *E. coli* strain containing a lysogen of kDE3, and therefore carrying a chromosomal copy of the T7 RNA polymerase gene under the control of the lacUV5 promoter, is transformed with a bacterial expression vector containing an IPTG-inducible promoter encoding a nucleic acid sequence corresponding to one or more of the polypeptides of the present invention. Cultures are grown in luria broth medium supplemented with 34 μg/mL chloroamphenicol and 15 μg/mL kanamycin at 37° C. When the OD600 reaches >0.4, the temperature is reduced to 18° C. and the cells are induced with 0.5 mM IPTG for 17 hours. The bacterial cells are then resuspended in buffer containing 50 mM $NaH_2PO_4$, pH 8, 300 mM NaCl, 20 mM imidazole, 10% glycerol, 0.1% NP40, 2 mM DTT and protease inhibitors (VWR), lysed in a Gaulin homogenizer, and centrifuged to remove cell debris before protein purification.

In one embodiment, purification of the polypeptides of the present invention can be achieved using a polyhistidine tag at the amino-terminus. A nickel column is used in affinity purifications of polyhistidine tags, with, for example, a 5 mL column being utilized for lysate generated by 4 L of *E. coli*. The lysate is loaded onto the column and then washed with Buffer A (50 mM $NaH_2PO_4$, 300 mM NaCl, 30% glycerol, 20 mM imidazole, 2 mM DTT at pH 7.5). A step elution to 7% Buffer B (50 mM $NaH_2PO_4$, 300 mM NaCl, 30% glycerol, 2 M imidazole, 2 mM DTT at pH 6.8), for 3.2 column volumes is then carried out. A gradient to 100% Buffer B over 3 column volumes is then carried out. The polypeptide of the present invention can then be gel-filtered into Buffer C (50 mM $NaH_2PO_4$, 150 mM NaCl, 40% glycerol, 1 mM EDTA, 2 mM DTT at pH 6.8) and loaded onto a cation exchange column for further purification. After the protein is loaded, the column is washed with Buffer C followed by a step elution to 75% of Buffer D (50 mM $NaH_2PO_4$, 1 M NaCl, 40% glycerol, 1 mM EDTA, 2 mM DTT at pH 6.8), then a 5 column volume gradient to 100% Buffer D. The protein is then gel filtered into Buffer E (50 mM $NaH_2PO_4$, 300 mM NaCl, 40% glycerol, 1 mM EDTA, 2 mM DTT at pH 6.8) and stored at −20° C.

Different embodiments of the polypeptides of the invention, including but not limited to: those lacking a polyhistidine tag, those possessing a polyarginine tag, those with reduced cysteine content, those with amino acid sequence variations designed to make the drug candidate more thermally stable, those with modifications to enhance or reduce a particular activity of the drug candidate, may require alternative purification strategies. Embodiments of the polypeptide drug candidate lacking a polyhistidine tag, for example, may be directly applied to a cation exchange column. Additional steps, for example the use of hydrophobic interaction chromatography, may be utilized by taking the protein in Buffer F (50 mM $NaH_2PO_4$, 300 mM NaCl, 1 M $(NH_4)_2SO_4$, 30% glycerol, 1 mM EDTA, 2 mM DTT at pH 6.8) and running a 10 column volume gradient to 100% Buffer E. Other affinity columns or sizing columns may be used to purify different embodiments of the polypeptide drug candidates.

Alternative techniques may also be used for exchange of buffers, concentration of the drug candidates and purification of the drug candidates. These could include, but are not limited to, ultrafiltration, tangential flow filtration and diafiltration for the concentration of the drug candidate and for exchange of buffers. Techniques such a precipitation of the drug candidates by $(NH_4)_2SO_4$ or some other chemical agent may also be used. Denaturing the drug candidate in urea or some other denaturant and refolding it may also be used.

The polypeptides of the present invention are stabilized by excipients containing salts; solutions stable at 300 mM NaCl can begin to precipitate at 150 mM NaCl. For this reason excipient mixtures will favor these stabilizing salt concentrations, which could include but are not limited to sodium phosphate, sodium chloride, calcium chloride, and magnesium chloride.

The addition of amino acid-based excipients such as arginine have proven to be stabilizing to the polypeptides of the present invention. A 10% solution of sucrose allows the polypeptides of the invention to be stable at 1 mg/mL, the addition of 2% w/v arginine allows some embodiments of the polypeptides to be stable at 3 mg/mL. For this reason, other amino acid based compounds, including but not limited to histidine, glutamine, glycine and human albumin, may be used as excipients.

The addition of excipients such as glycerol is stabilizing to polypeptides of the present invention. For example, in one embodiment, a polypeptide has a maximum concentration with 10% glycerol (v/v) of 1 mg/mL; while at 40% glycerol, the drug candidates are stable up to 12 mg/mL. Excipient mixtures containing compounds with similar chemical properties are envisioned that include but are not limited to polyols such as mannitol, xylitol and sorbitol. Disaccharides such as sucrose have been found to be stabilizing at 10% w/v; other disaccharides including but not limited to maltose and trehalose can also be used. Monosaccharides can also be used in the present invention. Polysorbates, polyethyleneglycols and similar compounds can also be used to practice the present invention.

As one skilled in the art will recognize, the use of antioxidants and preservatives may also be used to ensure stability of the polypeptides during storage. Antioxidants, including but not limited to sodium citrate, may be stabilizing for long term storage of the polypeptides of the invention. Preservatives, including but not limited to, benzyl alcohol may also be stabilizing to the polypeptides during storage and may be used in final excipient mixtures.

Measurement of Oligoadenylate Synthetase Activity of Polypeptides

The oligoadenylate synthetase activities of the polypeptides of the invention are measured according to previously published methods (Justesen, J., et al. Nuc Acids Res. 8:3073-3085, 1980). Briefly, protein is activated with 200 μg/ml polyinosinic:polycytidylic acid in buffer containing 20 mM Tris-HCl, pH 7.8, 50 mM Mg(OAc)$_2$, 1 mM DTT, 0.2 mM EDTA, 2.5 mM ATP, α[$^{32}$P]ATP, 0.5 mg/ml BSA, and 10% glycerol. The reaction proceeds at 37° C. for 30 minutes to 24 hours and is terminated by heating to 90° C. for 3 minutes. 2-4 μl of the reaction mixture is spotted onto a PEI-cellulose thin layer plate. After drying, the plate is developed with 0.4 M Tris-HCl, 30 mM MgCl$_2$, pH 8.7. The plate is dried and visualized by phosphorimager analysis. Alternatively, the reaction mixture can be further incubated with 0.05 U/μl calf intestinal phosphatase to remove the terminal phosphate. Thin layer chromatographic separation is achieved using a 0.76 M KH$_2$PO$_4$, pH 3.6 developing buffer system. The plate is then dried and visualized by phosphorimager analysis.

Measurement of Antiviral Activity of Polypeptides

The ability of the polypeptides of the present invention to protect cultured cells from cytotoxic viruses is demonstrated using a murine encephalomyocarditis virus (EMCV, ATCC strain VR-129B) infection model. Other in vitro virus infection models include but are not limited to flaviviruses such as bovine diarrheal virus, West Nile Virus, and GBV-C virus, other RNA viruses such as respiratory syncytial virus, and the HCV replicon systems (e.g. Blight, K. J., et al. 2002. J. Virology, 76:13001-13014). Any appropriate cultured cell competent for viral replication can be utilized in the antiviral assays.

Human Huh7 hepatoma cells are seeded at a density of 1×10$^4$ cells/well in 96 well culture plates and incubated overnight in complete medium (DMEM containing 10% fetal bovine serum). The following morning, the media is replaced with complete medium containing 0-10 μM protein or equivalent amounts of protein dilution buffer. When desired, alpha-interferon is added at a concentration of 100 μl/ml. Cells are pretreated for 2-8 hours preceding viral infection. After pretreatment, an equal volume of medium containing dilutions of EMC virus in complete medium is added to the wells. In the experiments described herein, a range of 50-500 plaque forming units (pfu) is added per well.

Viral infection is allowed to proceed overnight (approximately 18 hours), and the proportion of viable cells is calculated using any available cell viability or cytotoxicity reagents. The results described herein are obtained using a cell viability assay that measures conversion of a tetrazolium compound [3-(4,5-dimethyl-2-yl)-5-(3-carboxymethoxyphenyl)-2-(4-sulfophenyl)-2H-tetrazolium, inner salt; MTS] to a colored formazan compound in viable cells. The conversion of MTS to formazan is detected in a 96-well plate reader at an absorbance of 492 nm. The resulting optical densities either are plotted directly to estimate cell viability or are normalized by control-treated samples to calculate a percentage of viable cells after treatment.

Figure 3:
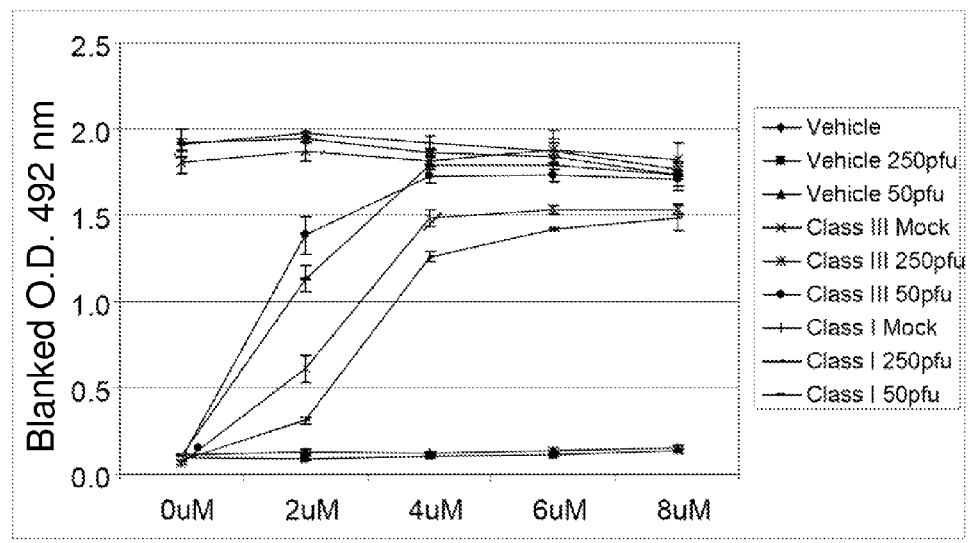
FIG. 3 demonstrates inhibition of EMCV-induced cell death in Huh7 cells by a Class I-Class III combination mutant polypeptide (the result of cloning SEQUENCE:4 of FIG. 7 into the NcoI and BamHI sites of the pET9d vector, followed by transformation into the Rosetta DE3 bacterial host and expression and purification according to the invention) and a reference Class III modified polypeptide variant polypeptides reacted at 0.5:1, 1:1, 2:1, 5:1, and 10:1 molar ratios, respectively. Lanes 7-11, mPEG-MAL 20 kDa-conjugated polypeptides reacted at 0.5:1, 1:1, 2:1, 5:1, and 10:1 molar ratios, respectively. As can be seen from the figure, the polypeptides of the invention retain full enzymatic activity when conjugated to polyethylene glycol at reactive cysteines.

FIG. 3 shows representative data from experiments comparing the antiviral activity of a Class I enzymatically inactive mutant to a reference polypeptide which is identical except for the Class I modification. In this particular case, the reference is itself a Class III mutant polypeptide of the invention. Treatment of cells with protein or vehicle containing medium alone did not result in significant decreases in cell viability. Conversely, pretreatment of cells with increasing concentrations of vehicle containing medium did not protect against EMCV-induced cell death when infected with either 50 or 250 pfu EMCV. Pretreatment with either the reference polypeptide or a Class I mutant polypeptide resulted in very similar dose-dependent increases in cell viability of Huh7 cells, with half-maximal inhibitory doses of approximately 1 μM and 2.5-3 μM at viral doses of 50 and 250 pfu, respectively.

Polypeptide Pegylation; Sulfhydryl

Conjugation of polyethylene glycol (PEG) to the polypeptides of the invention was achieved by mixing diothiothreitol (DTT)-free purified polypeptide with activated mPEG-MAL (Nektar Therapeutics) at a 0.5-10:1 molar ratio. The reaction proceeded at room temperature for 5 min-2 hours and was quenched by the addition of 2 mM DTT. Conjugation occurred at multiple cysteine sites using linear 20 kDa and branched 40 kDa PEGs (FIGS. 6A and 6B). Non-pegylated forms and forms containing one or more PEG can be separated from each other using a variety of chromatographic methodologies as known to those skilled in the art. In exemplary embodiments of the present invention, ion exchange columns, hydrophobic interactions columns, gel filtration and size exclusion chromatography, each alone or in combination with one another, can be utilized for isolation of the different PEG forms.

Polypeptide Pegylation; N-Terminal

Polypeptides of the invention can be peglyated at the N-terminal amine. To polypeptides in 50 mM NaH$_2$PO$_4$, 300 mM NaCl, 30% glycerol, 1 mM EDTA, 2 mM DTT at pH 5 containing 20 mM sodium cyanobororohydride and stirring in an ice bath are added a 5-fold excess of mPEG butyrALD-40K. The reaction is allowed to proceed for up to ten hours and then quenched by the addition of a 50-fold excess of glycine. Reaction products are analyzed by SDS-PAGE.

The following examples are offered by way of illustration and not by way of limitation.

EXAMPLES

Example 1

Site Directed Mutagenesis

The polypeptides of the present invention can be engineered using any standard method of site-directed mutagenesis. The nucleic acid sequences corresponding to the polypeptides of the invention were synthesized using specific oligonucleotide primers and a high fidelity DNA polymerase. The target sequence was contained on a double stranded plasmid isolated from a methylation-competent *E. coli* strain. Complimentary oligonucleotides containing the desired mutation were synthesized and purified using polyacrylamide gel electrophoresis. A thermal cycler was used to control the temperature for alternating cycles of denaturation of the double stranded plasmid template (94° C. for 30 seconds), annealing of the oligonucleotide primers (55° C. for 1 minute), and extension of the primers with a high fidelity polymerase (68° C. for 1 minute/kb of plasmid length). After approximately 15 cycles, the mixture of newly synthetized and input DNA were treated with a restriction enzyme specific for methylated residues (Dpn I) to digest the parental plasmid. The resulting DNA was introduced into chemically or electrically competent bacterial strains for screening and isolation of plasmids containing the desired mutation. Plasmid DNA was isolated from the transformants and screened via fluorescent dye-terminator sequencing to confirm the mutant sequence.

Example 2

Bulk Drug Product Expression, Fermentation, and Purification

An *E. coli* strain containing a lysogen of λDE3, and therefore carrying a chromosomal copy of the T7 RNA polymerase gene under the control of the lacUV5 promoter, was transformed with a bacterial expression vector containing an IPTG-inducible promoter encoding a nucleic acid sequence corresponding to one or more of the polypeptides of the present invention. Cultures were grown in luria broth medium supplemented with 34 μg/mL chloroamphenicol and 15 kanamycin at 37° C. When the OD600 reaches >0.4, the temperature was reduced to 18° C. and the cells were induced with 0.5 mM IPTG for 17 hours. The bacterial cells were then resuspended in buffer containing 50 mM $NaH_2PO_4$, pH 8, 300 mM NaCl, 20 mM imidazole, 10% glycerol, 0.1% NP40, 2 mM DTT and protease inhibitors (VWR), lysed in a Gaulin homogenizer, and centrifuged to remove cell debris before protein purification.

Purification of Histidine Tagged Polypeptides:

Purification of the polypeptides of the present invention was achieved using a polyhistidine tag at the amino-terminus. A nickel column, specifically a GE Healthcare 5 mL HisTrap FF column (17-5255-01), was used with two stacked 5 mL columns. The lysate was loaded onto the column with a 1.5 mL/min flowrate. The column was then washed with 15 column volumes (CV) of Buffer A (50 mM $NaH_2PO_4$, 300 mM NaCl, 30% glycerol, 20 mM imidazole, 2 mM DTT at pH 7.5). A step elution to 7% Buffer B (50 mM $NaH_2PO_4$, 300 mM NaCl, 30% glycerol, 2 M imidazole, 2 mM DTT at pH 7.5) was run for 2.5 CV. A gradient to 100% B over 2.5 CV was then carried out. All purification steps were carried out at room temperature.

The peak fractions from the nickel column containing the polypeptide were mixed and diluted 1:1 with Buffer A. $CaCl_2$ (from sterile filtered 1 M stock solution) was added to a 2 mM final concentration. Filtration was done to clarify. The filtrate was loaded onto an octyl FF column (GE Healthcare 17-1359-01) equilibrated in buffer A at a 0.5 mL/min flowrate, the polypeptide was in the flowthrough fractions.

The octyl column flowthrough was added to 5 volumes of Buffer C (10 mM $NaH_2PO_4$, 30% glycerol, 2 mM DTT, pH 8.8). The polypeptide was loaded onto a DEAE FF (GE Healthcare 17-5154-01) 5 mL column for endotoxin removal, at a 1.5 mL/min flowrate. This was followed by a 5 CV Buffer C wash, 1.5 mL/min flowrate, then a 10 CV gradient from 10 mM NaH2PO4, 30% glycerol, 2 mM DTT, pH 8.8 to 50 mM $NaH_2PO_4$, 1 M NaCl, 30% glycerol, 2 mM DTT, pH 8.0 was run.

The flowthrough fractions were pooled and diluted 1:1 with Buffer C while gently mixing, and the pH was adjusted to 6.8 with 2 N HCl. Then the polypeptide was loaded onto a 5 mL HiTrap SP FF (GE Healthcare 17-5157-01) column at a 1.5 mL/min flowrate. After the polypeptide was loaded, the column was washed with 5 CV of Buffer C (adjusted to pH 6.8) followed by a step elution to 75% of Buffer D (50 mM $NaH_2PO_4$, 1 M NaCl, 40% glycerol, 1 mM EDTA, 2 mM DTT at pH 6.8), then a 5 CV gradient to 100% Buffer D. The polypeptide was then gel filtered into Buffer E (50 mM $NaH_2PO_4$, 300 mM NaCl, 40% glycerol, 1 mM EDTA, 2 mM DTT at pH 6.8) and stored at –20° C.

Purification of Non-Tagged or Native Polypeptides:

Purification of polypeptides lacking an affinity tag was also achieved. Growth and preparation of clarified lysate was performed as previously described.

Alternatively, to clarify extracts and remove endotoxin, tangential flow filtration through a hollow fiber filtration device was carried out. Lysate was mixed with $CaCl_2$ to a final $CaCl_2$ concentration of 2 mM. Tangential flow filtration was performed with a GE Healthcare Midgee-UFP-500-E-MM01A (56-4100-56) which has a 500 kDa cutoff. The flowrate was 190 mL/min and the filtrate was collected and taken to the next step.

The protocol utilized GE Healthcare HITRAP SP FF 5 ml columns (17-5157-01), for the initial capture step, with a 5 mL column volume utilized for the amount of lysate generated by a 4 L growth/induction. The lysate was loaded onto the column with a 1.5 mL/min flowrate. The column was then washed with 5 column volumes of Buffer A (50 mM $NaH_2PO_4$, 25 mM NaCl, 30% glycerol, 2 mM DTT at pH 6.4). The polypeptide was eluted via a step gradient to 33% Buffer B (50 mM $NaH_2PO_4$, 1 M NaCl, 30% glycerol, 2 mM DTT at pH 6.8) which was run for 3 CV.

All subsequent steps subsequent were carried out under endotoxin free conditions.

Peak fractions from the cation exchange step were pooled and diluted 1:1 v/v with Buffer C (50 mM $NaH_2PO_4$, 300 mM mM NaCl, 30% glycerol, 2 mM DTT, 1 M $(NH_4)_2SO_4$, pH 6.8) and adjusted to 1 M $(NH_4)_2SO_4$ by adding the appropriate volume of 4 M $(NH_4)_2SO_4$ at pH 6.8. $CaCl_2$ was added to a 2 mM final concentration in the gently stirring solution then filtered to clarify. The polypeptide was then loaded onto a 5 mL HiTrap Phenyl HP (GE Healthcare 17-5195-01) column at a 0.5 mL/min flowrate, and the column was washed with 5 CV of Buffer C, then a 0.25 CV gradient to 33% Buffer D (50 mM $NaH_2PO_4$, 300 mM NaCl, 30% glycerol, 2 mM DTT, at pH 6.8) was performed. 33% Buffer D was run for 2 CV, followed by a 1 CV gradient to 55% D. The polypeptide was then eluted with a 5 CV elution at 55% Buffer D.

The polypeptide then went through a flowthrough anion exchange step to remove impurities and any remaining endotoxin. It was diluted 5:1 with Buffer E (10 mM $NaH_2PO_4$, 20% glycerol, 2 mM DTT, at pH 8) and adjusted to a final pH of 7.2 by slow addition of 2 N HCl to a gently stirred solution. The polypeptide was loaded on a 5 mL HiTrap DEAE FF (GE Healthcare 17-5154-01) column at 1.5 mL/min and washed with 5 CV of Buffer E. The polypeptide was in the flowthrough fractions.

The flowthrough fractions were pooled and diluted 1:1 with Buffer E and adjusted to pH 6.4. The protein was loaded onto a HITRAP SP FF 5 ml column (GE Healthcare 17-5157-01) at a 1.0 mL/min flowrate and washed with 2 CV of Buffer E. The polypeptide was eluted with a 10 CV gradient to 100% Buffer F (50 mM $NaH_2PO_4$, 500 mM NaCl, 30% glycerol, 2 mM DTT, 1 mM EDTA at pH 6.4) at a 0.5 mL/min flowrate.

The peak fractions were pooled and gel-filtered at a 2 mL/min flowrate, using a GE Healthcare HiTrap Desalting column (17-1408-01) into Buffer G (50 mM $NaH_2PO_4$, 300 mM NaCl, 25% glycerol, 1 mM EDTA, 2 mM DTT at pH 6.4) and stored at −80° C.

Alternatively, the cation exchange fractions were pooled and uniformly concentrated via ultrafiltration using an Amicon polethersulfone 10,000 NMWL membrane (PBGC02510). Buffer exchange into Buffer G was carried out via diafiltration or gel-filtration.

The addition of excipients such as glycerol was stabilizing to polypeptides of the present invention. For example, in one embodiment, a polypeptide with a polyhistidine affinity tag had a maximum concentration with 10% glycerol (v/v) of 1 mg/mL; while at 40% glycerol, the polypeptide was stable up to 12 mg/mL. Amino acid-based excipients such as arginine have proven to be stabilizing to this polypeptide. A 10% solution of sucrose allows the polypeptides of the invention to be stable at 1 mg/mL, the addition of 2% w/v arginine allowed an embodiment of the polypeptides to be stable at 3 mg/mL.

An embodiment of the polypeptides lacking an affinity tag for purification was also stabilized by particular excipients. The use of 50 mM $NaH_2PO_4$, 300 mM NaCl, 25% glycerol, 1 mM EDTA, 2 mM DTT at pH 6.4 was found to stabilize the polypeptide at 6 mg/mL. The use of 50 mM $NaH_2PO_4$, 300 mM NaCl, 10% mannitol, 1 mM EDTA, 0.5 mM DTT, 2% (w/v) arginine at pH 6.4 was found to stabilize the polypeptide at 4 mg/mL.

Example 3

Measurement of Oligoadenylate Synthetase Activity of Polypeptides

The oligoadenylate synthetase activities of the polypeptides of the invention were measured according to previously published methods (Justesen, J., et al. Nuc Acids Res. 8:3073-3085, 1980). Briefly, protein was activated with 200 μg/ml polyinosinic:polycytidylic acid in buffer containing 20 mM Tris-HCl, pH 7.8, 50 mM $Mg(OAc)_2$, 1 mM DTT, 0.2 mM EDTA, 2.5 mM ATP, $\alpha[^{32}P]ATP$, 0.5 mg/ml BSA, and 10% glycerol. The reaction proceeded at 37° C. for 30 minutes to 24 hours and was terminated by heating to 90° C. for 3 minutes. 2-4 μl of the reaction mixture was spotted onto a PEI-cellulose thin layer plate. After drying, the plate was developed with 0.4 M Tris-HCl, 30 mM $MgCl_2$, pH 8.7. The plate was dried and visualized by phosphorimager analysis. Alternatively, the reaction mixture was further incubated with 0.05 U/μl calf intestinal phosphatase to remove the terminal phosphate. Thin layer chromatographic separation was achieved using a 0.76 M $KH_2PO_4$, pH 3.6 developing buffer system. The plate was then dried and visualized by phosphorimager analysis.

Example 4

Measurement of Antiviral Activity of Polypeptides

The ability of the polypeptides of the present invention to protect cultured cells from cytotoxic viruses was demonstrated using a murine encephalomyocarditis virus (EMCV, ATCC strain VR-129B) infection model.

Human Huh7 hepatoma cells were seeded at a density of $1\times10^4$ cells/well in 96 well culture plates and incubated overnight in complete medium (DMEM containing 10% fetal bovine serum). The following morning, the media was replaced with complete medium containing 0-10 μM protein or equivalent amounts of protein dilution buffer. When appropriate, alpha-interferon was added at a concentration of 100 IU/ml. Cells were pretreated for 2-8 hours preceding viral infection. After pretreatment, an equal volume of medium containing dilutions of EMC virus in complete medium was added to the wells. In the experiments described herein, a range of 50-500 plaque forming units (pfu) was added per well.

Viral infections were allowed to proceed overnight (approximately 18 hours), and the proportion of viable cells was calculated using a cell viability assay that measures conversion of a tetrazolium compound [3-(4,5-dimethyl-2-yl)-5-(3-carboxymethoxyphenyl)-2-(4-sulfophenyl)-2H-tetrazolium, inner salt; MTS] to a colored formazan compound in viable cells. The conversion of MTS to formazan was detected in a 96-well plate reader at an absorbance of 492 nm. The resulting optical densities either were plotted directly to estimate cell viability or were normalized by control-treated samples to calculate a percentage of viable cells after treatment.

FIG. 3 shows representative data from experiments comparing the antiviral activity of a Class I enzymatically inactive mutant (the result of expression of SEQUENCE:4 (SEQ ID NO:4) of the invention by cloning into the NcoI and BamHI sites of the pET9d vector and transformation into the Rosetta DE3 bacterial host, followed by expression and purification according to the invention) to a reference polypeptide which is identical except for the Class I modification (the result of expression of SEQUENCE:2 (SEQ ID NO:2) of the invention by cloning into the NcoI and BamHI sites of the pET9d vector and transformation into the Rosetta DE3 bacterial host, followed by expression and purification according to the invention). In this particular case, the reference is itself a Class III mutant polypeptide of the invention.

Treatment of cells with protein or vehicle-containing medium alone did not result in significant decreases in cell viability. Conversely, pretreatment of cells with increasing concentrations of vehicle-containing medium did not protect against EMCV-induced cell death when infected with either 50 or 250 pfu EMCV. Pretreatment with either the reference polypeptide or a Class I mutant polypeptide resulted in very similar dose-dependent increases in cell viability of Huh7 cells, with half-maximal inhibitory doses of approximately 1 μM and 2.5-3 μM at viral doses of 50 and 250 pfu, respectively.

Example 5

Polypeptide Pegylation; Sulfhydryl

Conjugation of polyethylene glycol (PEG) to the polypeptides of the invention was achieved by mixing diothiothreitol (DTT)-free purified polypeptide with activated mPEG-MAL (Nektar Therapeutics) at a 0.5-10:1 molar ratio. The reaction proceeded at room temperature for 5 min-2 hours and was quenched by the addition of 2 mM dithiothreitol. Conjugation occurred at multiple cysteine sites using linear 20 kDa and branched 40 kDa PEGs (FIGS. 6A and 6B). Non-pegylated forms and forms containing one or more PEG groups were separated from each other using SDS-PAGE.

Example 6

Toxicology Analysis

The objective of this study was to assess the 7-day acute toxicity of a protein-based drug ("test article" or "TA1") in out-bred mice. "TA1" or "test article" refers to a Class III polypeptide of the invention, expressed and purified by cloning SEQUENCE:2 (SEQ ID NO:2) of the invention into the NcoI and BamHI sites of pET9d, followed by transformation of the recombinant clone into the Rosetta DE3 bacterial strain. Protein expression and purification was effected as described elsewhere in the specification.

The study was comprised of three groups (N=10, 5 male and 5 female) of CD-1 mice (6-7 weeks, Simonsen Laboratories, Gilroy, Calif.). On Day 0, the animals were weighed and given permanent study numbers. Their dosages were calculated based on group's average body weights. The mice were dosed once daily by the intraperitoneal route (IP) for seven days with vehicle, TA1 at 5 mg/kg, or TA1 at 25 mg/kg. The animals were monitored for clinical signs and mortality following each dose. On day 7, all mice were weighed, sacrificed and underwent necropsy. Target organs were collected and fixed in 10% formalin for histology processing, which included brain, lungs, heart, thymus, liver, spleen, kidneys, stomach, testes (male)/ovaries (female).

The vehicle for this study was a clear solution composed of: 50 mM $NaH_2PO_4$, 300 mM NaCl, 10% Sucrose, 2% glutamine, 1 mM EDTA, 0.5 mM DTT in deionized $H_2O$.

TA1 was provided in 7 tubes of 4.5 ml solution each. TA1 was dissolved into the vehicle at the concentration of 2.5 mg/ml. Upon delivery it was stored in the non-GLP compartment of the −80° C. freezer until needed for the study.

Thirty (30) CD-1 mice (15 male and 15 female) (*Mus musculus*) were used in the study. Mice were selected for the study since mice are an accepted species frequently used in the pre-clinical evaluation of drugs intended for human use.

All animals were weighed on Day 0, Day 3 and Day 7. Each animal received a single IP dose of test article daily for seven days. Dose volumes were calculated based on the average body weights for each group. Clinical observations, including morbidity, mortality, and overt signs of toxic or pharmacologic effect(s) were recorded for animals periodically throughout the in-life portion of the study.

Body weights ranged from 24.3 to 38.0 g. There were no drug related effects on body weights. There was no mortality observed during the course of this study. All animals appeared bright, alert, active and responsive, no significant observations were recorded during the in-life phase.

According to the body weights and clinical observations, no observable toxic effect of compound TA1 was detected at the dose levels evaluated. Histopathology examination of major organs by a certified pathologist also determined that no detectable toxicity on histologic level was present. Briefly, brain, heart, stomach, kidney, liver, spleen, and gonads were prepared as hematoxylin-eosin stained glass slides and evaluated histopathologically. All protocol-specified tissues from all animals were examined. There were no toxicologically relevant lesions seen in the tissues examined in any of the groups. The test article appears to be well-tolerated at the doses given under the conditions of this study.

Example 7

Antibody Development

Monoclonal antibodies were developed against a polypeptide of the invention. With respect to the development of antibodies, "HIS-OAS1" and "his-tagged OAS1" refer to the polypeptide product resulting from expression of SEQUENCE:2 (SEQ ID NO:2) as cloned into the NcoI and BamHI sites of the pET9d expression vector and expressed in and purified from the Rosetta DE3 bacterial host (Novagen, La Jolla, Calif.) according to the specification. "Non-HIS-OAS1" and "non-his tagged OAS1" refer to the polypeptide product resulting from expression of SEQUENCE:3 (SEQ ID NO:3) as cloned into the NcoI and BamHI sites of the pET9d expression vector and expressed in and purified from the Rosetta DE3 bacterial host (Novagen, La Jolla, Calif.) according to the specification.

Materials:

Criteria for acceptability for hybridoma development components are as follows: received from companies certified according to DIN EN ISO 9001; delivered at the correct storage temperature; received with a certificate of analysis; AND passing in-house testing in cell culture and test fusions.

Chemicals:

Not listed chemicals are pro analysi (p.a.) quality and were received from Fluka, Merck, Sigma and Riedel-de Haen. Aminopterin Hybri-Max $2 \times 10^{-5}$ M (50×), SIGMA; Antibiotic/Antimycotic: 10000 I.E. Penicillin, 10000 µg/ml Streptomycin, 25 µg/ml Amphotericin (100×), GIBCO/BRL; BSA (Bovine Serum Albumin), SIGMA; DMEM (Dulbecco's Modified Eagle Medium), SIGMA; DMSO Hybri-Max, SIGMA; FCS (Fetal Calf Serum), PAA; Freund's Complete, Incomplete Adjuvant, SIGMA; GlutaMAX-I Supplement 2×10-1 M (100×), GIBCO/BRL; L-Glutamine 2×10-1 M (100×), GIBCO/BRL; Goat anti-Mouse IgG (mouse Fc specific)-AP (alkaline phosphatase), SIGMA; HT Supplement (50×): Hypoxanthine (5×10-3 M), Thymidine (0.8×10-3 M), GIBCO/BRL MEM Non-essential Amino acid Solution (100×), GIBCO/BRL; 2-Mercaptoethanol, SIGMA; Sodium pyruvate MEM 10-1 M mM (100×), GIBCO/BRL; 4-Nitrophenyl Phosphate, SIGMA; Polyethylene glycol (PEG) Hybri-Max (3550), SIGMA Mice:

For generation of hybridomas, BALB/C mice (female, about 8 weeks old) from Charles River Laboratories (Germany) were used.

Myeloma Cell Line:

For fusion the myeloma cell line SP2/0-Ag14 from German Collection of Microorganisms and Cell Cultures (DSMZ GmbH, Braunschweig) was used. This cell line is a hybrid between BALB/c spleen cells and the myeloma cell line P3x63Ag8. The cells were described as not synthesizing or secreting immunoglobulin chains, being resistant to 8-azaguanine at 20 and not growing in HAT (Hypoxanthine, Aminopterin, Thymidine) medium.

The SP2/0 cells are routinely maintained in tissue culture flasks in standard growth medium (with 10% FCS). Regularly a new aliquot of frozen SP2/0 cells was used in order to avoid the development of HGPRT-positive revertants. Myeloma cells are negative in all mycoplasma tests performed by DSMZ GmbH.

Antigen:

A preparation of his-tagged OAS1 (concentration 3 mg/ml in 50 mM $NaH_2PO_4$/300 mM NaCl/40% glycerol/1 mM EDTA/2 mM DTT at pH 6.8) was used for immunization and screening.

For negative selection of clones reacting to his-tag, his-beta galactosidase (concentration 2.36 mg/ml in 25 mM HEPES/200 mM NaCl/1 Mm EDTA/5% glycerol, pH 6.8), and for positive selection non-his-tagged human OAS1 (concentration 4.3 mg/ml in 50 mM NaH$_2$PO$_4$/300 mM NaCl/40% glycerol/1 mM EDTA/2 mM DTT at pH 6.8), were used.

Immunization:

Six mice were immunized intraperitoneal over a period of 39 days. For immunization a water-in-oil emulsion of equal volumes of antigen and Freund's complete or incomplete adjuvant was prepared. The mice with the highest antiserum titer were chosen for fusion and stimulated over 4 days.

Preparation of the Antiserum:

The blood from the immunized mice was allowed to stay for 1 h at RT. After incubation overnight at 4° C., the blood was centrifuged for 10 min at 10000 g. The supernatant (antiserum) was collected and tested in ELISA as described below.

General Handling of Cells and Cell Culture Supernatants:

Cells were handled under sterile conditions using laminar air flow system, sterile materials and sterile solutions. Cells were incubated at 37° C. in a humid atmosphere containing 5% carbon dioxide. For cultivation of the hybridoma cells, a complete growth medium (CGM) containing DMEM with supplements 2-mercaptoethanol, L-Glutamin, GlutaMax, HT, non essential amino acids, sodium pyruvate, antibiotics/antimycotic solution (in concentrations recommended by the supplier) and FCS at different concentrations (10%, 15% or 20%) were used.

The cell culture supernatants from hybridoma cells contained usually 12 to 20 µg/ml antibody. Determination of the suitable cell culture supernatant dilution was recommended for every experiment (dilution range: from undiluted to 1:1000).

Preparation of Spleen Cells and Cell Fusion:

A single cell suspension of pooled spleens was prepared. The spleen cells and the myeloma cells were washed several times with DMEM and fused in the presence of 1 ml 50% (w/v) PEG 3550 (ratio spleen cells to SP2/0 3:1). The resulting hybridomas were resuspended in CGM containing 20% FCS and aminopterin (HAT medium). The cell suspension (140 µl/well) was plated out into eight 96-well tissue culture flat-bottom plates (Corning-Costar) containing 140 µl/well CGM (20% FCS) with peritoneal exudate cells as feeder cells. The plates were incubated for 10 days. During this period, cells were fed two times with HAT medium. An aliquot of the spleen cell preparation was cultivated 10 days in a T-flask, and the cell culture supernatant served as a positive control in ELISA. Another aliquot of the spleen cell preparation was frozen in freezing medium (FCS+10% dimethyl sulfoxide) and stored in liquid nitrogen.

Screening Assay:

An ELISA was used for screening of IgG in cell culture supernatants. 96 well flat-bottom polystyrene microtiter plates (Greiner, Cat. No 655061) were coated with 50 µl/well antigen (2 µg/ml) in 0.5 M carbonate/bicarbonate buffer, pH 9.6. After incubation overnight (o/n) in a moist chamber at 4° C. the plates were washed with tris-buffered saline (TBS, 50 mM Tris, pH 7.8, 500 mM sodium chloride) containing 0.01% Triton X-100 (washing buffer) and blocked with 200 µl/well 2% FCS in TBS (blocking buffer) for 1 hour at room temperature (RT) on a shaker. The wells were washed with washing buffer and 100 µl cell culture supernatant antisera (a 2-fold dilution series in blocking buffer, starting with 1:100) were added in the appropriate well.

Cell culture supernatant from SP 2/0 myeloma cells was used as negative control. As positive control cell culture supernatant from spleen cells culture was used. The plates were incubated on a shaker for 1 h at RT, followed by several washes. For detection of bound antibodies plates were incubated with 50 µl/well goat anti-mouse IgG conjugated to alkaline phosphatase (1:5000) in blocking buffer for 1 h at RT on a shaker, followed by several washes and addition of 150 µl/well substrate buffer (2 mM 4-nitrophenyl phosphate in 5% diethanolamine+0.5 mM MgCl$_2$, pH 9.8). The optical density (OD) was estimated in a 12-channel Dynex Opsys MR microplate reader at 405 nm. Wells with OD405 nm two-fold higher than the OD405 nm of the average plate value were selected as positive.

Selection of Stable Antibody Producers:

Cells from positive wells were transferred into wells of 24 well plates and cultivated for a few days. An ELISA on his-tagged OAS 1, non-his-tagged OAS1 and his-beta galactosidase in order to select the specific binders was carried out. Because of the high probability of chromosome loss in the hybrids this phase was kept as short as possible.

Limiting Dilution Cloning:

As soon as positive wells were identified, hybridoma cells were cloned to reduce the risk of overgrowth by non-producing cells (first cloning). To ensure that the antibodies are truly monoclonal, the hybridomas were cloned again (second cloning).

The method of limiting dilution was used for both cloning procedures. IgG producing cells were distributed into one 96 well plate containing feeder cells at a concentration of 1-3 cells per well. After 8-10 days (depending on growths characteristics), all plates were visually inspected under the microscope for detection of monoclonal growth. Culture supernatants from such wells were screened for specific immunoglobulin content by the above described screening assay. The appropriate clones concerning growth characteristic and ELISA signal were selected, transferred into wells of a 24 well plate and cultivated for some days. A screening assay was performed. This procedure was repeated two to three times. The appropriate subclone was selected respectively for the second cloning procedure and cryopreservation/production.

Antiserum Results:

The ELISA results of the antisera are shown in Table 1, which provides ELISA results (OD405 nm) of antisera against OAS1 after 15 min incubation with substrate.

TABLE 1

| Antisera Dilution | Mouse 1 | Mouse 2 | Mouse 3 | Mouse 4 | Mouse 5 | Mouse 6 |
|---|---|---|---|---|---|---|
| 1:100 | 1.533 | 1.026 | 1.176 | 0.420 | 0.201 | 0.195 |
| 1:200 | 1.261 | 0.666 | 0.650 | 0.216 | 0.122 | 0.121 |
| 1:400 | 0.907 | 0.473 | 0.497 | 0.148 | 0.091 | 0.091 |
| 1:800 | 0.540 | 0.306 | 0.308 | 0.097 | 0.061 | 0.063 |
| 1:1600 | 0.314 | 0.202 | 0.204 | 0.079 | 0.049 | 0.060 |
| 1:3200 | 0.183 | 0.135 | 0.126 | 0.062 | 0.042 | 0.045 |
| 1:6400 | 0.106 | 0.098 | 0.088 | 0.042 | 0.036 | 0.039 |
| blank | 0.038 | 0.038 | 0.037 | 0.039 | 0.033 | 0.037 |

The mice 1, 2 and 3 were chosen for fusion.

Results after Fusion and Selection of Stable Antibody Producers:

The fusion resulted in a number of good growing hybridomas. After the selection of stable antibody producers, three primary cultures were identified as positive. These primary cultures were screened on his-tagged and non-his-tagged OAS1, and his-tagged beta galactosidase. The OD405 values are shown in Table 2. which shows the ELISA signals of primary cultures OD405 nm after 1 h incubation with substrate.

TABLE 2

| culture | his-OAS1 | non-his OAS1 | his-beta gal |
|---|---|---|---|
| 1 | 1.601 | 1.617 | 0.017 |
| 2 | 0.314 | 1.153 | 0.010 |
| 11 | 0.230 | 0.018 | 0.298 |
| splenocyte cell culture | 1.247 | 1.555 | 0.526 |
| negative control | 0.012 | 0.008 | 0.009 |

The antibodies of primary cultures 1 and 2 bind specifically to OAS1 protein; therefore these cells were taken into 1st cloning. The antibodies of primary culture 11 bind his-tag and were excluded.

From the foregoing, although specific embodiments of the invention have been described herein for purposes of illustration, various modifications may be made without departing from the spirit and scope of the invention. Accordingly, the invention is not limited except as by the appended claims. All publications, published patent applications, and patent documents disclosed herein are hereby incorporated by reference.

What is claimed is:

1. A method of treating a viral infection in a mammal in need thereof, comprising administering to said mammal a pharmaceutical composition comprising an antiviral but enzymatically inactive 2',5' oligoadenylate synthetase (OAS) polypeptide consisting of SEQ ID NO. 1 except that the OAS polypeptide has (a) a mutation at position 75 and/or 77, and (b) an amino acid mutation at one or more of positions 1, 25, 31, 38, 45, 54, 109, 115, 127, 162, 177, 189, 219, 269, 280, 330, 331, and 346.

2. The method of claim 1, wherein the mutation replaces Asp with Ala at positions 75 and/or 77.

3. The method of claim 1, wherein the amino acid mutation is the substitution of Gly with Ser at position 162.

4. The method of claim 1, wherein said viral infection is caused by a member of the Flaviviridae family, the Hepadnaviridae family, the Picornaviridae family, the Retroviridae family, the Coronaviridae family, the Rhabdoviridae family, the Paramyxoviridae family, the Papillomaviridae family, or the Herpesviridae family.

5. The method of claim 1, wherein said viral infection is caused by Hepatitis C Virus, Yellow Fever Virus, West Nile Virus, Japanese Encephalitis Virus, Dengue Virus, Bovine Viral Diarrhea Virus, Hepatitis B Virus, Encephalomyocarditis Virus, Human Rhinovirus, Hepatitis A Virus, Human Immunodeficiency Virus, Simian Immunodeficiency Virus, Human T-Lymphotropic Virus, Rous Sarcoma Virus, SARS coronavirus, Rabies Virus, Vesicular Stomatitis Virus, Respiratory Syncytial Virus, Parainfluenza Virus, Human Papillomavirus, or Herpes Simplex Virus.

6. The method of claim 1, wherein said treating is therapeutic or prophylactic.

7. The method of claim 3, wherein the amino acid mutation is the deletion of Met at position 1.

8. The method of claim 3, wherein the amino acid mutation is the substitution of Cys with Ala, Gly, Met, Ser, Thr, or no amino acid at position 25, 38, 45, 54, 109, 177, 189, 219, 269, or 331.

9. The method of claim 3, wherein the amino acid mutation is the substitution of Asn with Asp at position 31.

10. The method of claim 3, wherein the amino acid mutation is the substitution of Phe with Leu at position 115.

11. The method of claim 1, wherein the amino acid mutation is the substitution of Gly with Arg at position 127.

12. The method of claim 3, wherein the amino acid mutation is the substitution of Asn with Thr at position 280.

13. The method of claim 3, wherein the amino acid mutation is the substitution of Pro with Ser at position 330.

14. The method of claim 3, wherein the amino acid mutation is the deletion of Leu at position 346.

* * * * *

SEQUENCE LISTING

```
<160> NUMBER OF SEQ ID NOS: 17

<210> SEQ ID NO 1
<211> LENGTH: 346
<212> TYPE: PRT
<213> ORGANISM: Homo sapiens
<220> FEATURE:
<221> NAME/KEY: VARIANT
<222> LOCATION: (1)..(1)
<223> OTHER INFORMATION: Xaa = Met OR -Met (Met deleted)
<220> FEATURE:
<221> NAME/KEY: VARIANT
<222> LOCATION: (25)..(25)
<223> OTHER INFORMATION: Xaa = Cys OR Ala OR Gly OR Met OR
      Ser OR Thr OR -Cys (Cys Deleted)
<220> FEATURE:
<221> NAME/KEY: VARIANT
<222> LOCATION: (31)..(31)
<223> OTHER INFORMATION: Xaa  = Asn OR Asp
<220> FEATURE:
<221> NAME/KEY: VARIANT
<222> LOCATION: (38)..(54)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (75)..(77)
<223> OTHER INFORMATION: Xaa = Asp OR Ala
<220> FEATURE:
<221> NAME/KEY: VARIANT
<222> LOCATION: (109)..(109)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (115)..(115)
<223> OTHER INFORMATION: Xaa = Phe OR Leu
<220> FEATURE:
<221> NAME/KEY: VARIANT
<222> LOCATION: (127)..(127)
<223> OTHER INFORMATION: Xaa  = Gly OR Arg
<220> FEATURE:
<221> NAME/KEY: VARIANT
<222> LOCATION: (162)..(162)
<223> OTHER INFORMATION: Xaa = Gly OR Ser
<220> FEATURE:
<221> NAME/KEY: VARIANT
<222> LOCATION: (177)..(269)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (280)..(280)
<223> OTHER INFORMATION: Xaa = Asn OR Thr
<220> FEATURE:
<221> NAME/KEY: VARIANT
<222> LOCATION: (330)..(330)
<223> OTHER INFORMATION: Xaa = Pro OR Ser
<220> FEATURE:
<221> NAME/KEY: VARIANT
<222> LOCATION: (331)..(331)
<223> OTHER INFORMATION: Xaa = Cys OR Ala OR Gly OR Met OR Ser OR Thr OR
      -Cys (Cys Deleted)
<220> FEATURE:
```

<221> NAME/KEY: VARIANT
<222> LOCATION: (346)..(346)
<223> OTHER INFORMATION: Xaa = Leu OR -Leu (Leu Deleted)

<400> SEQUENCE: 1

```
Xaa Met Asp Leu Arg Asn Thr Pro Ala Lys Ser Leu Asp Lys Phe Ile
1               5                   10                  15

Glu Asp Tyr Leu Leu Pro Asp Thr Xaa Phe Arg Met Gln Ile Xaa His
            20                  25                  30

Ala Ile Asp Ile Ile Xaa Gly Phe Leu Lys Glu Arg Xaa Phe Arg Gly
        35                  40                  45

Ser Ser Tyr Pro Val Xaa Val Ser Lys Val Val Lys Gly Gly Ser Ser
    50                  55                  60

Gly Lys Gly Thr Thr Leu Arg Gly Arg Ser Xaa Ala Xaa Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Xaa Gln Arg Glu
            100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
                165                 170                 175

Xaa Thr Asp Leu Gln Lys Glu Gly Glu Phe Ser Thr Xaa Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Xaa Lys Lys Lys Leu Gly
    210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Xaa Ile Tyr Trp
            260                 265                 270

Thr Lys Tyr Tyr Asp Phe Lys Xaa Pro Ile Ile Glu Lys Tyr Leu Arg
        275                 280                 285

Arg Gln Leu Thr Lys Pro Arg Pro Val Ile Leu Asp Pro Ala Asp Pro
    290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Xaa Xaa Phe Lys Asn Trp Asp
                325                 330                 335

Gly Ser Pro Val Ser Ser Trp Ile Leu Xaa
            340                 345
```

<210> SEQ ID NO 2
<211> LENGTH: 1115
<212> TYPE: DNA
<213> ORGANISM: Homo sapiens

<400> SEQUENCE: 2

```
ccatgggcca tcatcatcat catcatcatc atcatcacag cagcggccat atcgaaggtc      60
gtcatatgat ggatctcaga aatacccag ccaaatctct ggacaagttc attgaagact     120
atctcttgcc agacacgtgt ttccgcatgc aaatcaacca tgccattgac atcatctgtg    180
ggttcctgaa ggaaaggtgc ttccgaggta gctcctaccc tgtgtgtgtg tccaaggtgg    240
taaagggtgg ctcctcaggc aagggcacca ccctcagagg ccgatctgac gctgacctgg    300
ttgtcttcct cagtcctctc accactttc aggatcagtt aaatcgccgg ggagagttca    360
tccaggaaat taggagacag ctggaagcct gtcaaagaga gagagcattt ccgtgaagt     420 ttgaggtcca ggctccacgc tggggcaacc cccgtgcgct cagcttcgta ctgagttcgc    480
tccagctcgg ggaggggggtg gagttcgatg tgctgcctgc ctttgatgcc ctgggtcagt   540
tgactggcgg ctataaacct aacccccaaa tctatgtcaa gctcatcgag gagtgcaccg    600
acctgcagaa agagggcgag ttctccacct gcttcacaga actacagaga gacttcctga    660
agcagcgccc caccaagctc aagagcctca tccgcctagt caagcactgg taccaaaatt    720
gtaagaagaa gcttgggaag ctgccaccte agtatgccct ggagctcctg acggtctatg    780
cttgggagcg agggagcatg aaaacacatt tcaacacagc ccagggattt cggacggtct    840
tggaattagt cataaactac cagcaactct gcatctactg gacaaagtat tatgactta    900 aaaccccat tattgaaaag tacctgagaa ggcagctcac gaaacccagg cctgtgatcc     960
tggacccggc ggaccctaca ggaaacttgg gtggtggaga cccaaagggt tggaggcagc   1020
tggcacaaga ggctgaggcc tggctgaatt acccatgctt taagaattgg gatgggtccc   1080
cagtgagctc ctggattctg ctgtgatctg gatcc                              1115

<210> SEQ ID NO 3
<211> LENGTH: 1049
<212> TYPE: DNA
<213> ORGANISM: Homo sapiens

<400> SEQUENCE: 3
ccatggatct cagaaatacc ccagccaaat ctctggacaa gttcattgaa gactatctct      60
tgccagacac gtgtttccgc atgcaaatca accatgccat tgacatcatc tgtgggttcc    120
tgaaggaaag gtgcttccga ggtagctcct accctgtgtg tgtgtccaag gtggtaaagg    180
gtggctcctc aggcaagggc accaccctca gaggccgatc tgacgctgac ctggttgtct    240
tcctcagtcc tctcaccact tttcaggatc agttaaatcg ccggggagag ttcatccagg    300
aaattaggag acagctggaa gcctgtcaaa gagagagagc attttccgtg aagtttgagg    360
tccaggctcc acgctggggc aaccccgtg cgctcagctt cgtactgagt tcgctccagc    420
tcggggaggg ggtggagttc gatgtgctgc ctgccttga tgccctgggt cagttgactg     480
gcggctataa acctaacccc caaatctatg tcaagctcat cgaggagtgc accgacctgc    540
agaaagaggg cgagttctcc acctgcttca gaactacaga gagacttc ctgaagcagc    600 gccccaccaa gctcaagagc ctcatccgcc tagtcaagca ctggtaccaa aattgtaaga    660
agaagcttgg gaagctgcca cctcagtatg ccctggagct cctgacggtc tatgcttggg    720
agcgagggag catgaaaaca catttcaaca cagcccaggg atttcggacg gtcttggaat    780 agtcataaa ctaccagcaa ctctgcatct actggacaaa gtattatgac tttaaaaacc    840
ccattattga aaagtacctg agaaggcagc tcacgaaacc caggcctgtg atcctggacc    900
cggcggaccc tacaggaaac ttgggtggtg gagacccaaa gggttggagg cagctggcac    960
```

```
aagaggctga ggcctggctg aattacccat gctttaagaa ttgggatggg tccccagtga    1020
gctcctggat tctgctgtga tctggatcc                                     1049

<210> SEQ ID NO 4
<211> LENGTH: 1115
<212> TYPE: DNA
<213> ORGANISM: Homo sapiens

<400> SEQUENCE: 4
ccatgggcca tcatcatcat catcatcatc atcatcacag cagcggccat atcgaaggtc      60
gtcatatgat ggatctcaga atacccccag ccaaatctct ggacaagttc attgaagact     120
atctcttgcc agacacgtgt ttccgcatgc aaatcaacca tgccattgac atcatctgtg     180
ggttcctgaa ggaaaggtgc ttccgaggta gctcctaccc tgtgtgtgtg tccaaggtgg     240
taaagggtgg ctcctcaggc aagggcacca ccctcagagg ccgatctgcc gctgcgctgg     300
ttgtcttcct cagtcctctc accactttt aggatcagtt aaatcgccgg ggagagttca      360
tccaggaaat taggagacag ctggaagcct gtcaaagaga gagagcattt ccgtgaagt      420 ttgaggtcca ggctccacgc tggggcaacc cccgtgcgct cagcttcgta ctgagttcgc     480
tccagctcgg gagggggtg gagttcgatg tgctgcctgc ctttgatgcc ctgggtcagt      540
tgactggcgg ctataaacct aaccccccaaa tctatgtcaa gctcatcgag gagtgcaccg    600
acctgcagaa agagggcgag ttctccacct gcttcacaga actacagaga gacttcctga    660
agcagcgccc caccaagctc aagagcctca tccgcctagt caagcactgg taccaaaatt    720
gtaagaagaa gcttgggaag ctgccacctc agtatgccct ggagctcctg acggtctatg    780
cttgggagcg agggagcatg aaaacacatt tcaacacagc ccagggattt cggacggtct    840
tggaattagt cataaactac cagcaactct gcatctactg gacaaagtat tatgacttta    900 aaaccccat tattgaaaag tacctgagaa ggcagctcac gaaacccagg cctgtgatcc      960
tggacccggc ggaccctaca ggaaacttgg gtggtggaga cccaaagggt tggaggcagc    1020
tggcacaaga ggctgaggcc tggctgaatt acccatgctt taagaattgg gatgggtccc    1080
cagtgagctc ctggattctg ctgtgatctg gatcc                              1115

<210> SEQ ID NO 5
<211> LENGTH: 362
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = His or -His (His deleted)
<220> FEATURE:
<221> NAME/KEY: VARIANT
<222> LOCATION: (41)..(41)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (47)..(47)
<223> OTHER INFORMATION: Xaa  = Asn OR Asp
<220> FEATURE:
<221> NAME/KEY: VARIANT
<222> LOCATION: (54)..(70)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (91)..(93)
<223> OTHER INFORMATION: Xaa = Asp OR Ala
<220> FEATURE:
<221> NAME/KEY: VARIANT
```

```
<222> LOCATION: (125)..(125)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (131)..(131)
<223> OTHER INFORMATION: Xaa = Phe OR Leu
<220> FEATURE:
<221> NAME/KEY: VARIANT
<222> LOCATION: (143)..(143)
<223> OTHER INFORMATION: Xaa = Gly OR Arg
<220> FEATURE:
<221> NAME/KEY: VARIANT
<222> LOCATION: (178)..(178)
<223> OTHER INFORMATION: Xaa = Gly OR Ser
<220> FEATURE:
<221> NAME/KEY: VARIANT
<222> LOCATION: (193)..(285)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (296)..(296)
<223> OTHER INFORMATION: Xaa = Asn OR Thr
<220> FEATURE:
<221> NAME/KEY: VARIANT
<222> LOCATION: (346)..(346)
<223> OTHER INFORMATION: Xaa = Pro OR Ser
<220> FEATURE:
<221> NAME/KEY: VARIANT
<222> LOCATION: (347)..(347)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (362)..(362)
<223> OTHER INFORMATION: Xaa = Leu OR -Leu (Leu Deleted)

<400> SEQUENCE: 5

Met His Xaa Xaa Xaa Xaa Xaa Xaa Xaa Xaa Xaa Xaa Xaa Xaa Xaa Xaa
1               5                   10                  15

Met Met Asp Leu Arg Asn Thr Pro Ala Lys Ser Leu Asp Lys Phe Ile
            20                  25                  30

Glu Asp Tyr Leu Leu Pro Asp Thr Xaa Phe Arg Met Gln Ile Xaa His
        35                  40                  45

Ala Ile Asp Ile Ile Xaa Gly Phe Leu Lys Glu Arg Xaa Phe Arg Gly
    50                  55                  60

Ser Ser Tyr Pro Val Xaa Val Ser Lys Val Val Lys Gly Gly Ser Ser
65                  70                  75                  80

Gly Lys Gly Thr Thr Leu Arg Gly Arg Ser Xaa Ala Xaa Leu Val Val
                85                  90                  95

Phe Leu Ser Pro Leu Thr Thr Phe Gln Asp Gln Leu Asn Arg Arg Gly
            100                 105                 110

Glu Phe Ile Gln Glu Ile Arg Arg Gln Leu Glu Ala Xaa Gln Arg Glu
        115                 120                 125

Arg Ala Xaa Ser Val Lys Phe Glu Val Gln Ala Pro Arg Trp Xaa Asn
    130                 135                 140

Pro Arg Ala Leu Ser Phe Val Leu Ser Ser Leu Gln Leu Gly Glu Gly
145                 150                 155                 160

Val Glu Phe Asp Val Leu Pro Ala Phe Asp Ala Leu Gly Gln Leu Thr
                165                 170                 175

Gly Xaa Tyr Lys Pro Asn Pro Gln Ile Tyr Val Lys Leu Ile Glu Glu
            180                 185                 190

Xaa Thr Asp Leu Gln Lys Glu Gly Glu Phe Ser Thr Xaa Phe Thr Glu
        195                 200                 205
```

```
Leu Gln Arg Asp Phe Leu Lys Gln Arg Pro Thr Lys Leu Lys Ser Leu
    210                 215                 220
Ile Arg Leu Val Lys His Trp Tyr Gln Asn Xaa Lys Lys Lys Leu Gly
225                 230                 235                 240
Lys Leu Pro Pro Gln Tyr Ala Leu Glu Leu Leu Thr Val Tyr Ala Trp
                245                 250                 255
Glu Arg Gly Ser Met Lys Thr His Phe Asn Thr Ala Gln Gly Phe Arg
            260                 265                 270
Thr Val Leu Glu Leu Val Ile Asn Tyr Gln Gln Leu Xaa Ile Tyr Trp
        275                 280                 285
Thr Lys Tyr Tyr Asp Phe Lys Xaa Pro Ile Ile Glu Lys Tyr Leu Arg
    290                 295                 300
Arg Gln Leu Thr Lys Pro Arg Pro Val Ile Leu Asp Pro Ala Asp Pro
305                 310                 315                 320
Thr Gly Asn Leu Gly Gly Gly Asp Pro Lys Gly Trp Arg Gln Leu Ala
                325                 330                 335
Gln Glu Ala Glu Ala Trp Leu Asn Tyr Xaa Xaa Phe Lys Asn Trp Asp
            340                 345                 350
Gly Ser Pro Val Ser Ser Trp Ile Leu Xaa
        355                 360

<210> SEQ ID NO 6
<211> LENGTH: 361
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = His OR -His (His deleted)
<220> FEATURE:
<221> NAME/KEY: VARIANT
<222> LOCATION: (40)..(40)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (46)..(46)
<223> OTHER INFORMATION: Xaa  = Asn OR Asp
<220> FEATURE:
<221> NAME/KEY: VARIANT
<222> LOCATION: (53)..(69)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (90)..(92)
<223> OTHER INFORMATION: Xaa = Asp OR Ala
<220> FEATURE:
<221> NAME/KEY: VARIANT
<222> LOCATION: (124)..(124)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (130)..(130)
<223> OTHER INFORMATION: Xaa = Phe OR Leu
<220> FEATURE:
<221> NAME/KEY: VARIANT
<222> LOCATION: (142)..(142)
<223> OTHER INFORMATION: Xaa  = Gly OR Arg
<220> FEATURE:
<221> NAME/KEY: VARIANT
<222> LOCATION: (177)..(177)
<223> OTHER INFORMATION: Xaa = Gly OR Ser
<220> FEATURE:
<221> NAME/KEY: VARIANT
<222> LOCATION: (192)..(284)
<223> OTHER INFORMATION: Xaa = Cys OR Ala OR Gly OR Met OR Ser OR Thr OR
      -Cys (Cys Deleted)
```

```
<220> FEATURE:
<221> NAME/KEY: VARIANT
<222> LOCATION: (295)..(295)
<223> OTHER INFORMATION: Xaa = Asn OR Thr
<220> FEATURE:
<221> NAME/KEY: VARIANT
<222> LOCATION: (345)..(345)
<223> OTHER INFORMATION: Xaa = Pro OR Ser
<220> FEATURE:
<221> NAME/KEY: VARIANT
<222> LOCATION: (346)..(346)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (361)..(361)
<223> OTHER INFORMATION: Xaa = Leu OR -Leu (Leu Deleted)

<400> SEQUENCE: 6

Met His Xaa Xaa Xaa Xaa Xaa Xaa Xaa Xaa Xaa Xaa Xaa Xaa
1               5                   10                  15

Met Asp Leu Arg Asn Thr Pro Ala Lys Ser Leu Asp Lys Phe Ile Glu
            20                  25                  30

Asp Tyr Leu Leu Pro Asp Thr Xaa Phe Arg Met Gln Ile Xaa His Ala
        35                  40                  45

Ile Asp Ile Ile Xaa Gly Phe Leu Lys Glu Arg Xaa Phe Arg Gly Ser
    50                  55                  60

Ser Tyr Pro Val Xaa Val Ser Lys Val Val Lys Gly Ser Ser Gly
65                  70                  75                  80

Lys Gly Thr Thr Leu Arg Gly Arg Ser Xaa Ala Xaa Leu Val Val Phe
                85                  90                  95

Leu Ser Pro Leu Thr Thr Phe Gln Asp Gln Leu Asn Arg Arg Gly Glu
            100                 105                 110

Phe Ile Gln Glu Ile Arg Arg Gln Leu Glu Ala Xaa Gln Arg Glu Arg
        115                 120                 125

Ala Xaa Ser Val Lys Phe Glu Val Gln Ala Pro Arg Trp Xaa Asn Pro
    130                 135                 140

Arg Ala Leu Ser Phe Val Leu Ser Ser Leu Gln Leu Gly Glu Gly Val
145                 150                 155                 160

Glu Phe Asp Val Leu Pro Ala Phe Asp Ala Leu Gly Gln Leu Thr Gly
                165                 170                 175

Xaa Tyr Lys Pro Asn Pro Gln Ile Tyr Val Lys Leu Ile Glu Glu Xaa
            180                 185                 190

Thr Asp Leu Gln Lys Glu Gly Glu Phe Ser Thr Xaa Phe Thr Glu Leu
        195                 200                 205

Gln Arg Asp Phe Leu Lys Gln Arg Pro Thr Leu Lys Ser Leu Ile
    210                 215                 220

Arg Leu Val Lys His Trp Tyr Gln Asn Xaa Lys Lys Lys Leu Gly Lys
225                 230                 235                 240

Leu Pro Pro Gln Tyr Ala Leu Glu Leu Leu Thr Val Tyr Ala Trp Glu
                245                 250                 255

Arg Gly Ser Met Lys Thr His Phe Asn Thr Ala Gln Gly Phe Arg Thr
            260                 265                 270

Val Leu Glu Leu Val Ile Asn Tyr Gln Gln Leu Xaa Ile Tyr Trp Thr
        275                 280                 285

Lys Tyr Tyr Asp Phe Lys Xaa Pro Ile Ile Glu Lys Tyr Leu Arg Arg
    290                 295                 300

Gln Leu Thr Lys Pro Arg Pro Val Ile Leu Asp Pro Ala Asp Pro Thr
305                 310                 315                 320
```

```
Gly Asn Leu Gly Gly Gly Asp Pro Lys Gly Trp Arg Gln Leu Ala Gln
            325                 330                 335

Glu Ala Glu Ala Trp Leu Asn Tyr Xaa Xaa Phe Lys Asn Trp Asp Gly
        340                 345                 350

Ser Pro Val Ser Ser Trp Ile Leu Xaa
        355                 360

<210> SEQ ID NO 7
<211> LENGTH: 362
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = Arg OR -Arg (Arg deleted)
<220> FEATURE:
<221> NAME/KEY: VARIANT
<222> LOCATION: (41)..(41)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (47)..(47)
<223> OTHER INFORMATION: Xaa  = Asn OR Asp
<220> FEATURE:
<221> NAME/KEY: VARIANT
<222> LOCATION: (54)..(70)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (91)..(93)
<223> OTHER INFORMATION: Xaa = Asp OR Ala
<220> FEATURE:
<221> NAME/KEY: VARIANT
<222> LOCATION: (125)..(125)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (131)..(131)
<223> OTHER INFORMATION: Xaa = Phe OR Leu
<220> FEATURE:
<221> NAME/KEY: VARIANT
<222> LOCATION: (143)..(143)
<223> OTHER INFORMATION: Xaa  = Gly OR Arg
<220> FEATURE:
<221> NAME/KEY: VARIANT
<222> LOCATION: (178)..(178)
<223> OTHER INFORMATION: Xaa = Gly OR Ser
<220> FEATURE:
<221> NAME/KEY: VARIANT
<222> LOCATION: (193)..(285)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (296)..(296)
<223> OTHER INFORMATION: Xaa = Asn OR Thr
<220> FEATURE:
<221> NAME/KEY: VARIANT
<222> LOCATION: (346)..(346)
<223> OTHER INFORMATION: Xaa = Pro OR Ser
<220> FEATURE:
<221> NAME/KEY: VARIANT
<222> LOCATION: (347)..(347)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (362)..(362)
<223> OTHER INFORMATION: Xaa = Leu OR -Leu (Leu Deleted)

<400> SEQUENCE: 7
```

```
Met Arg Xaa Xaa Xaa Xaa Xaa Xaa Xaa Xaa Xaa Xaa Xaa Xaa Xaa
1               5                   10                  15
Met Met Asp Leu Arg Asn Thr Pro Ala Lys Ser Leu Asp Lys Phe Ile
            20                  25                  30
Glu Asp Tyr Leu Leu Pro Asp Thr Xaa Phe Arg Met Gln Ile Xaa His
            35                  40                  45
Ala Ile Asp Ile Ile Xaa Gly Phe Leu Lys Glu Arg Xaa Phe Arg Gly
50                  55                  60
Ser Ser Tyr Pro Val Xaa Val Ser Lys Val Val Lys Gly Gly Ser Ser
65                  70                  75                  80
Gly Lys Gly Thr Thr Leu Arg Gly Arg Ser Xaa Ala Xaa Leu Val Val
            85                  90                  95
Phe Leu Ser Pro Leu Thr Thr Phe Gln Asp Gln Leu Asn Arg Arg Gly
            100                 105                 110
Glu Phe Ile Gln Glu Ile Arg Arg Gln Leu Glu Ala Xaa Gln Arg Glu
            115                 120                 125
Arg Ala Xaa Ser Val Lys Phe Glu Val Gln Ala Pro Arg Trp Xaa Asn
130                 135                 140
Pro Arg Ala Leu Ser Phe Val Leu Ser Ser Leu Gln Leu Gly Glu Gly
145                 150                 155                 160
Val Glu Phe Asp Val Leu Pro Ala Phe Asp Ala Leu Gly Gln Leu Thr
            165                 170                 175
Gly Xaa Tyr Lys Pro Asn Pro Gln Ile Tyr Val Lys Leu Ile Glu Glu
            180                 185                 190
Xaa Thr Asp Leu Gln Lys Glu Gly Glu Phe Ser Thr Xaa Phe Thr Glu
            195                 200                 205
Leu Gln Arg Asp Phe Leu Lys Gln Arg Pro Thr Lys Leu Lys Ser Leu
            210                 215                 220
Ile Arg Leu Val Lys His Trp Tyr Gln Asn Xaa Lys Lys Lys Leu Gly
225                 230                 235                 240
Lys Leu Pro Pro Gln Tyr Ala Leu Glu Leu Leu Thr Val Tyr Ala Trp
            245                 250                 255
Glu Arg Gly Ser Met Lys Thr His Phe Asn Thr Ala Gln Gly Phe Arg
            260                 265                 270
Thr Val Leu Glu Leu Val Ile Asn Tyr Gln Gln Leu Xaa Ile Tyr Trp
            275                 280                 285
Thr Lys Tyr Tyr Asp Phe Lys Xaa Pro Ile Ile Glu Lys Tyr Leu Arg
            290                 295                 300
Arg Gln Leu Thr Lys Pro Arg Pro Val Ile Leu Asp Pro Ala Asp Pro
305                 310                 315                 320
Thr Gly Asn Leu Gly Gly Gly Asp Pro Lys Gly Trp Arg Gln Leu Ala
            325                 330                 335
Gln Glu Ala Glu Ala Trp Leu Asn Tyr Xaa Xaa Phe Lys Asn Trp Asp
            340                 345                 350
Gly Ser Pro Val Ser Ser Trp Ile Leu Xaa
            355                 360

<210> SEQ ID NO 8
<211> LENGTH: 361
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = Arg OR -Arg (Arg deleted)
<220> FEATURE:
```

```
<221> NAME/KEY: VARIANT
<222> LOCATION: (40)..(40)
<223> OTHER INFORMATION: Xaa = Cys OR Ala OR Gly OR Met OR Ser OR Thr OR
      -Cys (Cys
      Deleted)
<220> FEATURE:
<221> NAME/KEY: VARIANT
<222> LOCATION: (46)..(46)
<223> OTHER INFORMATION: Xaa = Asn OR Asp
<220> FEATURE:
<221> NAME/KEY: VARIANT
<222> LOCATION: (53)..(69)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (90)..(92)
<223> OTHER INFORMATION: Xaa = Asp OR Ala
<220> FEATURE:
<221> NAME/KEY: VARIANT
<222> LOCATION: (124)..(124)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (130)..(130)
<223> OTHER INFORMATION: Xaa = Phe OR Leu
<220> FEATURE:
<221> NAME/KEY: VARIANT
<222> LOCATION: (142)..(142)
<223> OTHER INFORMATION: Xaa = Gly OR Arg
<220> FEATURE:
<221> NAME/KEY: VARIANT
<222> LOCATION: (177)..(177)
<223> OTHER INFORMATION: Xaa = Gly OR Ser
<220> FEATURE:
<221> NAME/KEY: VARIANT
<222> LOCATION: (192)..(284)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (295)..(295)
<223> OTHER INFORMATION: Xaa = Asn OR Thr
<220> FEATURE:
<221> NAME/KEY: VARIANT
<222> LOCATION: (345)..(345)
<223> OTHER INFORMATION: Xaa = Pro OR Ser
<220> FEATURE:
<221> NAME/KEY: VARIANT
<222> LOCATION: (346)..(346)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (361)..(361)
<223> OTHER INFORMATION: Xaa = Leu OR -Leu (Leu Deleted)

<400> SEQUENCE: 8

Met Arg Xaa Xaa Xaa Xaa Xaa Xaa Xaa Xaa Xaa Xaa Xaa Xaa Xaa
1               5                   10                  15

Met Asp Leu Arg Asn Thr Pro Ala Lys Ser Leu Asp Lys Phe Ile Glu
            20                  25                  30

Asp Tyr Leu Leu Pro Asp Thr Xaa Phe Arg Met Gln Ile Xaa His Ala
        35                  40                  45

Ile Asp Ile Ile Xaa Gly Phe Leu Lys Glu Arg Xaa Phe Arg Gly Ser
    50                  55                  60

Ser Tyr Pro Val Xaa Val Ser Lys Val Val Lys Gly Gly Ser Ser Gly
65                  70                  75                  80

Lys Gly Thr Thr Leu Arg Gly Arg Ser Xaa Ala Xaa Leu Val Val Phe
                85                  90                  95

Leu Ser Pro Leu Thr Thr Phe Gln Asp Gln Leu Asn Arg Arg Gly Glu
```

```
                100                 105                 110
Phe Ile Gln Glu Ile Arg Arg Gln Leu Glu Ala Xaa Gln Arg Glu Arg
            115                 120                 125
Ala Xaa Ser Val Lys Phe Glu Val Gln Ala Pro Arg Trp Xaa Asn Pro
        130                 135                 140
Arg Ala Leu Ser Phe Val Leu Ser Ser Leu Gln Leu Gly Glu Gly Val
145                 150                 155                 160
Glu Phe Asp Val Leu Pro Ala Phe Asp Ala Leu Gly Gln Leu Thr Gly
                165                 170                 175
Xaa Tyr Lys Pro Asn Pro Gln Ile Tyr Val Lys Leu Ile Glu Glu Xaa
            180                 185                 190
Thr Asp Leu Gln Lys Glu Gly Glu Phe Ser Thr Xaa Phe Thr Glu Leu
        195                 200                 205
Gln Arg Asp Phe Leu Lys Gln Arg Pro Thr Lys Leu Lys Ser Leu Ile
210                 215                 220
Arg Leu Val Lys His Trp Tyr Gln Asn Xaa Lys Lys Leu Gly Lys
225                 230                 235                 240
Leu Pro Pro Gln Tyr Ala Leu Glu Leu Leu Thr Val Tyr Ala Trp Glu
                245                 250                 255
Arg Gly Ser Met Lys Thr His Phe Asn Thr Ala Gln Gly Phe Arg Thr
            260                 265                 270
Val Leu Glu Leu Val Ile Asn Tyr Gln Gln Leu Xaa Ile Tyr Trp Thr
        275                 280                 285
Lys Tyr Tyr Asp Phe Lys Xaa Pro Ile Ile Glu Lys Tyr Leu Arg Arg
        290                 295                 300
Gln Leu Thr Lys Pro Arg Pro Val Ile Leu Asp Pro Ala Asp Pro Thr
305                 310                 315                 320
Gly Asn Leu Gly Gly Asp Pro Lys Gly Trp Arg Gln Leu Ala Gln
                325                 330                 335
Glu Ala Glu Ala Trp Leu Asn Tyr Xaa Xaa Phe Lys Asn Trp Asp Gly
            340                 345                 350
Ser Pro Val Ser Ser Trp Ile Leu Xaa
        355                 360

<210> SEQ ID NO 9
<211> LENGTH: 362
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = Lys OR -Lys (Lys deleted)
<220> FEATURE:
<221> NAME/KEY: VARIANT
<222> LOCATION: (41)..(41)
<223> OTHER INFORMATION: Xaa = Cys OR Ala OR Gly OR Met OR Ser OR Thr OR
    -Cys (Cys Deleted)
<220> FEATURE:
<221> NAME/KEY: VARIANT
<222> LOCATION: (47)..(47)
<223> OTHER INFORMATION: Xaa  = Asn OR Asp
<220> FEATURE:
<221> NAME/KEY: VARIANT
<222> LOCATION: (54)..(70)
<223> OTHER INFORMATION: Xaa = Cys OR Ala OR Gly OR Met OR Ser OR Thr OR
    -Cys (Cys Deleted)
<220> FEATURE:
<221> NAME/KEY: VARIANT
<222> LOCATION: (91)..(93)
<223> OTHER INFORMATION: Xaa = Asp OR Ala
<220> FEATURE:
<221> NAME/KEY: VARIANT
```

```
<222> LOCATION: (125)..(125)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (131)..(131)
<223> OTHER INFORMATION: Xaa = Phe OR Leu
<220> FEATURE:
<221> NAME/KEY: VARIANT
<222> LOCATION: (143)..(143)
<223> OTHER INFORMATION: Xaa = Gly OR Arg
<220> FEATURE:
<221> NAME/KEY: VARIANT
<222> LOCATION: (178)..(178)
<223> OTHER INFORMATION: Xaa = Gly OR Ser
<220> FEATURE:
<221> NAME/KEY: VARIANT
<222> LOCATION: (193)..(285)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (296)..(296)
<223> OTHER INFORMATION: Xaa = Asn OR Thr
<220> FEATURE:
<221> NAME/KEY: VARIANT
<222> LOCATION: (346)..(346)
<223> OTHER INFORMATION: Xaa = Pro OR Ser
<220> FEATURE:
<221> NAME/KEY: VARIANT
<222> LOCATION: (347)..(347)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (362)..(362)
<223> OTHER INFORMATION: Xaa = Leu OR -Leu (Leu Deleted)

<400> SEQUENCE: 9

Met Lys Xaa Xaa Xaa Xaa Xaa Xaa Xaa Xaa Xaa Xaa Xaa Xaa Xaa
1               5                   10                  15

Met Met Asp Leu Arg Asn Thr Pro Ala Lys Ser Leu Asp Lys Phe Ile
                20                  25                  30

Glu Asp Tyr Leu Leu Pro Asp Thr Xaa Phe Arg Met Gln Ile Xaa His
            35                  40                  45

Ala Ile Asp Ile Ile Xaa Gly Phe Leu Lys Glu Arg Xaa Phe Arg Gly
    50                  55                  60

Ser Ser Tyr Pro Val Xaa Val Ser Lys Val Val Lys Gly Gly Ser Ser
65                  70                  75                  80

Gly Lys Gly Thr Thr Leu Arg Gly Arg Ser Xaa Ala Xaa Leu Val Val
                85                  90                  95

Phe Leu Ser Pro Leu Thr Thr Phe Gln Asp Gln Leu Asn Arg Arg Gly
            100                 105                 110

Glu Phe Ile Gln Glu Ile Arg Arg Gln Leu Glu Ala Xaa Gln Arg Glu
        115                 120                 125

Arg Ala Xaa Ser Val Lys Phe Glu Val Gln Ala Pro Arg Trp Xaa Asn
    130                 135                 140

Pro Arg Ala Leu Ser Phe Val Leu Ser Ser Leu Gln Leu Gly Glu Gly
145                 150                 155                 160

Val Glu Phe Asp Val Leu Pro Ala Phe Asp Ala Leu Gly Gln Leu Thr
                165                 170                 175

Gly Xaa Tyr Lys Pro Asn Pro Gln Ile Tyr Val Lys Leu Ile Glu Glu
            180                 185                 190

Xaa Thr Asp Leu Gln Lys Glu Gly Glu Phe Ser Thr Xaa Phe Thr Glu
        195                 200                 205
```

```
Leu Gln Arg Asp Phe Leu Lys Gln Arg Pro Thr Lys Leu Lys Ser Leu
    210                 215                 220
Ile Arg Leu Val Lys His Trp Tyr Gln Asn Xaa Lys Lys Lys Leu Gly
225                 230                 235                 240
Lys Leu Pro Pro Gln Tyr Ala Leu Glu Leu Leu Thr Val Tyr Ala Trp
                245                 250                 255
Glu Arg Gly Ser Met Lys Thr His Phe Asn Thr Ala Gln Gly Phe Arg
                260                 265                 270
Thr Val Leu Glu Leu Val Ile Asn Tyr Gln Gln Leu Xaa Ile Tyr Trp
            275                 280                 285
Thr Lys Tyr Tyr Asp Phe Lys Xaa Pro Ile Ile Glu Lys Tyr Leu Arg
        290                 295                 300
Arg Gln Leu Thr Lys Pro Arg Pro Val Ile Leu Asp Pro Ala Asp Pro
305                 310                 315                 320
Thr Gly Asn Leu Gly Gly Gly Asp Pro Lys Gly Trp Arg Gln Leu Ala
                325                 330                 335
Gln Glu Ala Glu Ala Trp Leu Asn Tyr Xaa Xaa Phe Lys Asn Trp Asp
                340                 345                 350
Gly Ser Pro Val Ser Ser Trp Ile Leu Xaa
                355                 360

<210> SEQ ID NO 10
<211> LENGTH: 361
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = Lys OR -Lys (Lys deleted)
<220> FEATURE:
<221> NAME/KEY: VARIANT
<222> LOCATION: (40)..(40)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (46)..(46)
<223> OTHER INFORMATION: Xaa  = Asn OR Asp
<220> FEATURE:
<221> NAME/KEY: VARIANT
<222> LOCATION: (53)..(69)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (90)..(92)
<223> OTHER INFORMATION: Xaa = Asp OR Ala
<220> FEATURE:
<221> NAME/KEY: VARIANT
<222> LOCATION: (124)..(124)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (130)..(130)
<223> OTHER INFORMATION: Xaa = Phe OR Leu
<220> FEATURE:
<221> NAME/KEY: VARIANT
<222> LOCATION: (142)..(142)
<223> OTHER INFORMATION: Xaa  = Gly OR Arg
<220> FEATURE:
<221> NAME/KEY: VARIANT
<222> LOCATION: (177)..(177)
<223> OTHER INFORMATION: Xaa = Gly OR Ser
<220> FEATURE:
<221> NAME/KEY: VARIANT
<222> LOCATION: (192)..(284)
<223> OTHER INFORMATION: Xaa = Cys OR Ala OR Gly OR Met OR Ser OR Thr OR
      -Cys (Cys Deleted)
```

```
<220> FEATURE:
<221> NAME/KEY: VARIANT
<222> LOCATION: (295)..(295)
<223> OTHER INFORMATION: Xaa = Asn OR Thr
<220> FEATURE:
<221> NAME/KEY: VARIANT
<222> LOCATION: (345)..(345)
<223> OTHER INFORMATION: Xaa = Pro OR Ser
<220> FEATURE:
<221> NAME/KEY: VARIANT
<222> LOCATION: (346)..(346)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (361)..(361)
<223> OTHER INFORMATION: Xaa = Leu OR -Leu (Leu Deleted)

<400> SEQUENCE: 10

Met Lys Xaa Xaa Xaa Xaa Xaa Xaa Xaa Xaa Xaa Xaa Xaa Xaa Xaa Xaa
  1               5                  10                  15

Met Asp Leu Arg Asn Thr Pro Ala Lys Ser Leu Asp Lys Phe Ile Glu
             20                  25                  30

Asp Tyr Leu Leu Pro Asp Thr Xaa Phe Arg Met Gln Ile Xaa His Ala
         35                  40                  45

Ile Asp Ile Ile Xaa Gly Phe Leu Lys Glu Arg Xaa Phe Arg Gly Ser
     50                  55                  60

Ser Tyr Pro Val Xaa Val Ser Lys Val Val Lys Gly Ser Ser Gly
 65                  70                  75                  80

Lys Gly Thr Thr Leu Arg Gly Arg Ser Xaa Ala Xaa Leu Val Val Phe
             85                  90                  95

Leu Ser Pro Leu Thr Thr Phe Gln Asp Gln Leu Asn Arg Arg Gly Glu
            100                 105                 110

Phe Ile Gln Glu Ile Arg Arg Gln Leu Glu Ala Xaa Gln Arg Glu Arg
        115                 120                 125

Ala Xaa Ser Val Lys Phe Glu Val Gln Ala Pro Arg Trp Xaa Asn Pro
130                 135                 140

Arg Ala Leu Ser Phe Val Leu Ser Ser Leu Gln Leu Gly Glu Gly Val
145                 150                 155                 160

Glu Phe Asp Val Leu Pro Ala Phe Asp Ala Leu Gly Gln Leu Thr Gly
                165                 170                 175

Xaa Tyr Lys Pro Asn Pro Gln Ile Tyr Val Lys Leu Ile Glu Glu Xaa
            180                 185                 190

Thr Asp Leu Gln Lys Glu Gly Glu Phe Ser Thr Xaa Phe Thr Glu Leu
            195                 200                 205

Gln Arg Asp Phe Leu Lys Gln Arg Pro Thr Leu Leu Lys Ser Leu Ile
        210                 215                 220

Arg Leu Val Lys His Trp Tyr Gln Asn Xaa Lys Lys Lys Leu Gly Lys
225                 230                 235                 240

Leu Pro Pro Gln Tyr Ala Leu Glu Leu Leu Thr Val Tyr Ala Trp Glu
                245                 250                 255

Arg Gly Ser Met Lys Thr His Phe Asn Thr Ala Gln Gly Phe Arg Thr
            260                 265                 270

Val Leu Glu Leu Val Ile Asn Tyr Gln Gln Leu Xaa Ile Tyr Trp Thr
        275                 280                 285

Lys Tyr Tyr Asp Phe Lys Xaa Pro Ile Ile Glu Lys Tyr Leu Arg Arg
        290                 295                 300

Gln Leu Thr Lys Pro Arg Pro Val Ile Leu Asp Pro Ala Asp Pro Thr
305                 310                 315                 320
```

Gly Asn Leu Gly Gly Gly Asp Pro Lys Gly Trp Arg Gln Leu Ala Gln
                325                 330                 335

Glu Ala Glu Ala Trp Leu Asn Tyr Xaa Xaa Phe Lys Asn Trp Asp Gly
            340                 345                 350

Ser Pro Val Ser Ser Trp Ile Leu Xaa
        355                 360

<210> SEQ ID NO 11
<211> LENGTH: 363
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = His OR -His (His deleted)
<220> FEATURE:
<221> NAME/KEY: VARIANT
<222> LOCATION: (42)..(42)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (48)..(48)
<223> OTHER INFORMATION: Xaa = Asn OR Asp
<220> FEATURE:
<221> NAME/KEY: VARIANT
<222> LOCATION: (55)..(71)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (92)..(94)
<223> OTHER INFORMATION: Xaa = Asp OR Ala
<220> FEATURE:
<221> NAME/KEY: VARIANT
<222> LOCATION: (126)..(126)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (132)..(132)
<223> OTHER INFORMATION: Xaa = Phe OR Leu
<220> FEATURE:
<221> NAME/KEY: VARIANT
<222> LOCATION: (144)..(144)
<223> OTHER INFORMATION: Xaa = Gly OR Arg
<220> FEATURE:
<221> NAME/KEY: VARIANT
<222> LOCATION: (179)..(179)
<223> OTHER INFORMATION: Xaa = Gly OR Ser
<220> FEATURE:
<221> NAME/KEY: VARIANT
<222> LOCATION: (194)..(286)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (297)..(297)
<223> OTHER INFORMATION: Xaa = Asn OR Thr
<220> FEATURE:
<221> NAME/KEY: VARIANT
<222> LOCATION: (347)..(347)
<223> OTHER INFORMATION: Xaa = Pro OR Ser
<220> FEATURE:
<221> NAME/KEY: VARIANT
<222> LOCATION: (348)..(348)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (363)..(363)
<223> OTHER INFORMATION: Xaa = Leu OR -Leu (Leu Deleted)

<400> SEQUENCE: 11

```
Met His Xaa Xaa Xaa Xaa Xaa Xaa Xaa Xaa Xaa Xaa Xaa Xaa Xaa Xaa
1               5                   10                  15

Gly Met Met Asp Leu Arg Asn Thr Pro Ala Lys Ser Leu Asp Lys Phe
            20                  25                  30

Ile Glu Asp Tyr Leu Leu Pro Asp Thr Xaa Phe Arg Met Gln Ile Xaa
            35                  40                  45

His Ala Ile Asp Ile Ile Xaa Gly Phe Leu Lys Glu Arg Xaa Phe Arg
 50                  55                  60

Gly Ser Ser Tyr Pro Val Xaa Val Ser Lys Val Lys Gly Gly Ser
 65                  70                  75                  80

Ser Gly Lys Gly Thr Thr Leu Arg Gly Arg Ser Xaa Ala Xaa Leu Val
                85                  90                  95

Val Phe Leu Ser Pro Leu Thr Thr Phe Gln Asp Gln Leu Asn Arg Arg
            100                 105                 110

Gly Glu Phe Ile Gln Glu Ile Arg Arg Gln Leu Glu Ala Xaa Gln Arg
            115                 120                 125

Glu Arg Ala Xaa Ser Val Lys Phe Glu Val Gln Ala Pro Arg Trp Xaa
        130                 135                 140

Asn Pro Arg Ala Leu Ser Phe Val Leu Ser Ser Leu Gln Leu Gly Glu
145                 150                 155                 160

Gly Val Glu Phe Asp Val Leu Pro Ala Phe Asp Ala Leu Gly Gln Leu
                165                 170                 175

Thr Gly Xaa Tyr Lys Pro Asn Pro Gln Ile Tyr Val Lys Leu Ile Glu
            180                 185                 190

Glu Xaa Thr Asp Leu Gln Lys Glu Gly Glu Phe Ser Thr Xaa Phe Thr
        195                 200                 205

Glu Leu Gln Arg Asp Phe Leu Lys Gln Arg Pro Thr Lys Leu Lys Ser
        210                 215                 220

Leu Ile Arg Leu Val Lys His Trp Tyr Gln Asn Xaa Lys Lys Lys Leu
225                 230                 235                 240

Gly Lys Leu Pro Pro Gln Tyr Ala Leu Glu Leu Leu Thr Val Tyr Ala
            245                 250                 255

Trp Glu Arg Gly Ser Met Lys Thr His Phe Asn Thr Ala Gln Gly Phe
            260                 265                 270

Arg Thr Val Leu Glu Leu Val Ile Asn Tyr Gln Gln Leu Xaa Ile Tyr
        275                 280                 285

Trp Thr Lys Tyr Tyr Asp Phe Lys Xaa Pro Ile Ile Glu Lys Tyr Leu
        290                 295                 300

Arg Arg Gln Leu Thr Lys Pro Arg Pro Val Ile Leu Asp Pro Ala Asp
305                 310                 315                 320

Pro Thr Gly Asn Leu Gly Gly Asp Pro Lys Gly Trp Arg Gln Leu
            325                 330                 335

Ala Gln Glu Ala Glu Ala Trp Leu Asn Tyr Xaa Xaa Phe Lys Asn Trp
            340                 345                 350

Asp Gly Ser Pro Val Ser Ser Trp Ile Leu Xaa
            355                 360

<210> SEQ ID NO 12
<211> LENGTH: 362
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = His OR -His (His deleted)
<220> FEATURE:
```

```
<221> NAME/KEY: VARIANT
<222> LOCATION: (41)..(41)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (47)..(47)
<223> OTHER INFORMATION: Xaa = Asn OR Asp
<220> FEATURE:
<221> NAME/KEY: VARIANT
<222> LOCATION: (54)..(70)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (91)..(93)
<223> OTHER INFORMATION: Xaa = Asp OR Ala
<220> FEATURE:
<221> NAME/KEY: VARIANT
<222> LOCATION: (125)..(125)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (131)..(131)
<223> OTHER INFORMATION: Xaa = Phe OR Leu
<220> FEATURE:
<221> NAME/KEY: VARIANT
<222> LOCATION: (143)..(143)
<223> OTHER INFORMATION: Xaa = Gly OR Arg
<220> FEATURE:
<221> NAME/KEY: VARIANT
<222> LOCATION: (178)..(178)
<223> OTHER INFORMATION: Xaa = Gly OR Ser
<220> FEATURE:
<221> NAME/KEY: VARIANT
<222> LOCATION: (193)..(285)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (296)..(296)
<223> OTHER INFORMATION: Xaa = Asn OR Thr
<220> FEATURE:
<221> NAME/KEY: VARIANT
<222> LOCATION: (346)..(346)
<223> OTHER INFORMATION: Xaa = Pro OR Ser
<220> FEATURE:
<221> NAME/KEY: VARIANT
<222> LOCATION: (347)..(347)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (362)..(362)
<223> OTHER INFORMATION: Xaa = Leu OR -Leu (Leu Deleted)

<400> SEQUENCE: 12

Met His Xaa Xaa Xaa Xaa Xaa Xaa Xaa Xaa Xaa Xaa Xaa Xaa Xaa Xaa
1               5                   10                  15

Gly Met Asp Leu Arg Asn Thr Pro Ala Lys Ser Leu Asp Lys Phe Ile
            20                  25                  30

Glu Asp Tyr Leu Leu Pro Asp Thr Xaa Phe Arg Met Gln Ile Xaa His
        35                  40                  45

Ala Ile Asp Ile Ile Xaa Gly Phe Leu Lys Glu Arg Xaa Phe Arg Gly
    50                  55                  60

Ser Ser Tyr Pro Val Xaa Val Ser Lys Val Val Lys Gly Gly Ser Ser
65                  70                  75                  80

Gly Lys Gly Thr Thr Leu Arg Gly Arg Ser Xaa Ala Xaa Leu Val Val
            85                  90                  95

Phe Leu Ser Pro Leu Thr Thr Phe Gln Asp Gln Leu Asn Arg Arg Gly
            100                 105                 110
```

-continued

```
Glu Phe Ile Gln Glu Ile Arg Arg Gln Leu Glu Ala Xaa Gln Arg Glu
            115                 120                 125

Arg Ala Xaa Ser Val Lys Phe Glu Val Gln Ala Pro Arg Trp Xaa Asn
        130                 135                 140

Pro Arg Ala Leu Ser Phe Val Leu Ser Ser Leu Gln Leu Gly Glu Gly
145                 150                 155                 160

Val Glu Phe Asp Val Leu Pro Ala Phe Asp Ala Leu Gly Gln Leu Thr
                165                 170                 175

Gly Xaa Tyr Lys Pro Asn Pro Gln Ile Tyr Val Lys Leu Ile Glu Glu
            180                 185                 190

Xaa Thr Asp Leu Gln Lys Glu Gly Glu Phe Ser Thr Xaa Phe Thr Glu
        195                 200                 205

Leu Gln Arg Asp Phe Leu Lys Gln Arg Pro Thr Lys Leu Lys Ser Leu
210                 215                 220

Ile Arg Leu Val Lys His Trp Tyr Gln Asn Xaa Lys Lys Leu Gly
225                 230                 235                 240

Lys Leu Pro Pro Gln Tyr Ala Leu Glu Leu Leu Thr Val Tyr Ala Trp
                245                 250                 255

Glu Arg Gly Ser Met Lys Thr His Phe Asn Thr Ala Gln Gly Phe Arg
            260                 265                 270

Thr Val Leu Glu Leu Val Ile Asn Tyr Gln Gln Leu Xaa Ile Tyr Trp
        275                 280                 285

Thr Lys Tyr Tyr Asp Phe Lys Xaa Pro Ile Ile Glu Lys Tyr Leu Arg
290                 295                 300

Arg Gln Leu Thr Lys Pro Arg Pro Val Ile Leu Asp Pro Ala Asp Pro
305                 310                 315                 320

Thr Gly Asn Leu Gly Gly Gly Asp Pro Lys Gly Trp Arg Gln Leu Ala
                325                 330                 335

Gln Glu Ala Glu Ala Trp Leu Asn Tyr Xaa Xaa Phe Lys Asn Trp Asp
            340                 345                 350

Gly Ser Pro Val Ser Ser Trp Ile Leu Xaa
        355                 360

<210> SEQ ID NO 13
<211> LENGTH: 363
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = Arg OR -Arg (Arg deleted)
<220> FEATURE:
<221> NAME/KEY: VARIANT
<222> LOCATION: (42)..(42)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (48)..(48)
<223> OTHER INFORMATION: Xaa  = Asn OR Asp
<220> FEATURE:
<221> NAME/KEY: VARIANT
<222> LOCATION: (55)..(71)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (92)..(94)
<223> OTHER INFORMATION: Xaa = Asp OR Ala
<220> FEATURE:
<221> NAME/KEY: VARIANT
<222> LOCATION: (126)..(126)
```

```
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (132)..(132)
<223> OTHER INFORMATION: Xaa = Phe OR Leu
<220> FEATURE:
<221> NAME/KEY: VARIANT
<222> LOCATION: (144)..(144)
<223> OTHER INFORMATION: Xaa  = Gly OR Arg
<220> FEATURE:
<221> NAME/KEY: VARIANT
<222> LOCATION: (179)..(179)
<223> OTHER INFORMATION: Xaa = Gly OR Ser
<220> FEATURE:
<221> NAME/KEY: VARIANT
<222> LOCATION: (194)..(286)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (297)..(297)
<223> OTHER INFORMATION: Xaa = Asn OR Thr
<220> FEATURE:
<221> NAME/KEY: VARIANT
<222> LOCATION: (347)..(347)
<223> OTHER INFORMATION: Xaa = Pro OR Ser
<220> FEATURE:
<221> NAME/KEY: VARIANT
<222> LOCATION: (348)..(348)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (363)..(363)
<223> OTHER INFORMATION: Xaa = Leu OR -Leu (Leu Deleted)

<400> SEQUENCE: 13

Met Arg Xaa Xaa Xaa Xaa Xaa Xaa Xaa Xaa Xaa Xaa Xaa Xaa
1               5                   10                  15

Gly Met Met Asp Leu Arg Asn Thr Pro Ala Lys Ser Leu Asp Lys Phe
            20                  25                  30

Ile Glu Asp Tyr Leu Leu Pro Asp Thr Xaa Phe Arg Met Gln Ile Xaa
        35                  40                  45

His Ala Ile Asp Ile Ile Xaa Gly Phe Leu Lys Glu Arg Xaa Phe Arg
    50                  55                  60

Gly Ser Ser Tyr Pro Val Xaa Val Ser Lys Val Val Lys Gly Gly Ser
65                  70                  75                  80

Ser Gly Lys Gly Thr Thr Leu Arg Gly Arg Ser Xaa Ala Xaa Leu Val
                85                  90                  95

Val Phe Leu Ser Pro Leu Thr Thr Phe Gln Asp Gln Leu Asn Arg Arg
                100                 105                 110

Gly Glu Phe Ile Gln Glu Ile Arg Arg Gln Leu Glu Ala Xaa Gln Arg
            115                 120                 125

Glu Arg Ala Xaa Ser Val Lys Phe Glu Val Gln Ala Pro Arg Trp Xaa
        130                 135                 140

Asn Pro Arg Ala Leu Ser Phe Val Leu Ser Ser Leu Gln Leu Gly Glu
145                 150                 155                 160

Gly Val Glu Phe Asp Val Leu Pro Ala Phe Asp Ala Leu Gly Gln Leu
                165                 170                 175

Thr Gly Xaa Tyr Lys Pro Asn Pro Gln Ile Tyr Val Lys Leu Ile Glu
                180                 185                 190

Glu Xaa Thr Asp Leu Gln Lys Glu Gly Glu Phe Ser Thr Xaa Phe Thr
        195                 200                 205

Glu Leu Gln Arg Asp Phe Leu Lys Gln Arg Pro Thr Lys Leu Lys Ser
```

```
                    210                 215                 220
Leu Ile Arg Leu Val Lys His Trp Tyr Gln Asn Xaa Lys Lys Lys Leu
225                 230                 235                 240

Gly Lys Leu Pro Pro Gln Tyr Ala Leu Glu Leu Thr Val Tyr Ala
                245                 250                 255

Trp Glu Arg Gly Ser Met Lys Thr His Phe Asn Thr Ala Gln Gly Phe
                260                 265                 270

Arg Thr Val Leu Glu Leu Val Ile Asn Tyr Gln Gln Leu Xaa Ile Tyr
                275                 280                 285

Trp Thr Lys Tyr Tyr Asp Phe Lys Xaa Pro Ile Ile Glu Lys Tyr Leu
290                 295                 300

Arg Arg Gln Leu Thr Lys Pro Arg Pro Val Ile Leu Asp Pro Ala Asp
305                 310                 315                 320

Pro Thr Gly Asn Leu Gly Gly Gly Asp Pro Lys Gly Trp Arg Gln Leu
                325                 330                 335

Ala Gln Glu Ala Glu Ala Trp Leu Asn Tyr Xaa Xaa Phe Lys Asn Trp
                340                 345                 350

Asp Gly Ser Pro Val Ser Ser Trp Ile Leu Xaa
        355                 360

<210> SEQ ID NO 14
<211> LENGTH: 362
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = Arg OR -Arg (Arg deleted)
<220> FEATURE:
<221> NAME/KEY: VARIANT
<222> LOCATION: (41)..(41)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (47)..(47)
<223> OTHER INFORMATION: Xaa  = Asn OR Asp
<220> FEATURE:
<221> NAME/KEY: VARIANT
<222> LOCATION: (54)..(70)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (91)..(93)
<223> OTHER INFORMATION: Xaa = Asp OR Ala
<220> FEATURE:
<221> NAME/KEY: VARIANT
<222> LOCATION: (125)..(125)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (131)..(131)
<223> OTHER INFORMATION: Xaa = Phe OR Leu
<220> FEATURE:
<221> NAME/KEY: VARIANT
<222> LOCATION: (143)..(143)
<223> OTHER INFORMATION: Xaa  = Gly OR Arg
<220> FEATURE:
<221> NAME/KEY: VARIANT
<222> LOCATION: (178)..(178)
<223> OTHER INFORMATION: Xaa = Gly OR Ser
<220> FEATURE:
<221> NAME/KEY: VARIANT
<222> LOCATION: (193)..(285)
<223> OTHER INFORMATION: Xaa = Cys OR Ala OR Gly OR Met OR Ser OR Thr OR
      -Cys (Cys Deleted)
<220> FEATURE:
```

```
<221> NAME/KEY: VARIANT
<222> LOCATION: (296)..(296)
<223> OTHER INFORMATION: Xaa = Asn OR Thr
<220> FEATURE:
<221> NAME/KEY: VARIANT
<222> LOCATION: (346)..(346)
<223> OTHER INFORMATION: Xaa = Pro OR Ser
<220> FEATURE:
<221> NAME/KEY: VARIANT
<222> LOCATION: (347)..(347)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (362)..(362)
<223> OTHER INFORMATION: Xaa = Leu OR -Leu (Leu Deleted)

<400> SEQUENCE: 14

Met Arg Xaa Xaa Xaa Xaa Xaa Xaa Xaa Xaa Xaa Xaa Xaa Xaa
1               5                   10                  15

Gly Met Asp Leu Arg Asn Thr Pro Ala Lys Ser Leu Asp Lys Phe Ile
            20                  25                  30

Glu Asp Tyr Leu Leu Pro Asp Thr Xaa Phe Arg Met Gln Ile Xaa His
            35                  40                  45

Ala Ile Asp Ile Ile Xaa Gly Phe Leu Lys Glu Arg Xaa Phe Arg Gly
50                  55                  60

Ser Ser Tyr Pro Val Xaa Val Ser Lys Val Val Lys Gly Gly Ser Ser
65                  70                  75                  80

Gly Lys Gly Thr Thr Leu Arg Gly Arg Ser Xaa Ala Xaa Leu Val Val
            85                  90                  95

Phe Leu Ser Pro Leu Thr Thr Phe Gln Asp Gln Leu Asn Arg Arg Gly
            100                 105                 110

Glu Phe Ile Gln Glu Ile Arg Arg Gln Leu Glu Ala Xaa Gln Arg Glu
            115                 120                 125

Arg Ala Xaa Ser Val Lys Phe Glu Val Gln Ala Pro Arg Trp Xaa Asn
            130                 135                 140

Pro Arg Ala Leu Ser Phe Val Leu Ser Ser Leu Gln Leu Gly Glu Gly
145                 150                 155                 160

Val Glu Phe Asp Val Leu Pro Ala Phe Asp Ala Leu Gly Gln Leu Thr
            165                 170                 175

Gly Xaa Tyr Lys Pro Asn Pro Gln Ile Tyr Val Lys Leu Ile Glu Glu
            180                 185                 190

Xaa Thr Asp Leu Gln Lys Glu Gly Glu Phe Ser Thr Xaa Phe Thr Glu
            195                 200                 205

Leu Gln Arg Asp Phe Leu Lys Gln Arg Pro Thr Lys Leu Lys Ser Leu
            210                 215                 220

Ile Arg Leu Val Lys His Trp Tyr Gln Asn Xaa Lys Lys Lys Leu Gly
225                 230                 235                 240

Lys Leu Pro Pro Gln Tyr Ala Leu Glu Leu Leu Thr Val Tyr Ala Trp
            245                 250                 255

Glu Arg Gly Ser Met Lys Thr His Phe Asn Thr Ala Gln Gly Phe Arg
            260                 265                 270

Thr Val Leu Glu Leu Val Ile Asn Tyr Gln Gln Leu Xaa Ile Tyr Trp
            275                 280                 285

Thr Lys Tyr Tyr Asp Phe Lys Xaa Pro Ile Ile Glu Lys Tyr Leu Arg
            290                 295                 300

Arg Gln Leu Thr Lys Pro Arg Pro Val Ile Leu Asp Pro Ala Asp Pro
305                 310                 315                 320
```

```
Thr Gly Asn Leu Gly Gly Gly Asp Pro Lys Gly Trp Arg Gln Leu Ala
            325                 330                 335

Gln Glu Ala Glu Ala Trp Leu Asn Tyr Xaa Xaa Phe Lys Asn Trp Asp
        340                 345                 350

Gly Ser Pro Val Ser Ser Trp Ile Leu Xaa
        355                 360

<210> SEQ ID NO 15
<211> LENGTH: 363
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = Lys OR -Lys (Lys deleted)
<220> FEATURE:
<221> NAME/KEY: VARIANT
<222> LOCATION: (42)..(42)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (48)..(48)
<223> OTHER INFORMATION: Xaa  = Asn OR Asp
<220> FEATURE:
<221> NAME/KEY: VARIANT
<222> LOCATION: (55)..(71)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (92)..(94)
<223> OTHER INFORMATION: Xaa = Asp OR Ala
<220> FEATURE:
<221> NAME/KEY: VARIANT
<222> LOCATION: (126)..(126)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (132)..(132)
<223> OTHER INFORMATION: Xaa = Phe OR Leu
<220> FEATURE:
<221> NAME/KEY: VARIANT
<222> LOCATION: (144)..(144)
<223> OTHER INFORMATION: Xaa  = Gly OR Arg
<220> FEATURE:
<221> NAME/KEY: VARIANT
<222> LOCATION: (179)..(179)
<223> OTHER INFORMATION: Xaa = Gly OR Ser
<220> FEATURE:
<221> NAME/KEY: VARIANT
<222> LOCATION: (194)..(286)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (297)..(297)
<223> OTHER INFORMATION: Xaa = Asn OR Thr
<220> FEATURE:
<221> NAME/KEY: VARIANT
<222> LOCATION: (347)..(347)
<223> OTHER INFORMATION: Xaa = Pro OR Ser
<220> FEATURE:
<221> NAME/KEY: VARIANT
<222> LOCATION: (348)..(348)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (363)..(363)
<223> OTHER INFORMATION: Xaa = Leu OR -Leu (Leu Deleted)

<400> SEQUENCE: 15

Met Lys Xaa Xaa Xaa Xaa Xaa Xaa Xaa Xaa Xaa Xaa Xaa Xaa Xaa Xaa
```

```
            1               5                  10                  15
          Gly Met Met Asp Leu Arg Asn Thr Pro Ala Lys Ser Leu Asp Lys Phe
                       20                  25                  30
          Ile Glu Asp Tyr Leu Leu Pro Asp Thr Xaa Phe Arg Met Gln Ile Xaa
                       35                  40                  45
          His Ala Ile Asp Ile Ile Xaa Gly Phe Leu Lys Glu Arg Xaa Phe Arg
                       50                  55                  60
          Gly Ser Ser Tyr Pro Val Xaa Val Ser Lys Val Val Lys Gly Gly Ser
           65                  70                  75                  80
          Ser Gly Lys Gly Thr Thr Leu Arg Gly Arg Ser Xaa Ala Xaa Leu Val
                       85                  90                  95
          Val Phe Leu Ser Pro Leu Thr Thr Phe Gln Asp Gln Leu Asn Arg Arg
                       100                 105                 110
          Gly Glu Phe Ile Gln Glu Ile Arg Arg Gln Leu Glu Ala Xaa Gln Arg
                       115                 120                 125
          Glu Arg Ala Xaa Ser Val Lys Phe Glu Val Gln Ala Pro Arg Trp Xaa
                       130                 135                 140
          Asn Pro Arg Ala Leu Ser Phe Val Leu Ser Ser Leu Gln Leu Gly Glu
          145                 150                 155                 160
          Gly Val Glu Phe Asp Val Leu Pro Ala Phe Asp Ala Leu Gly Gln Leu
                       165                 170                 175
          Thr Gly Xaa Tyr Lys Pro Asn Pro Gln Ile Tyr Val Lys Leu Ile Glu
                       180                 185                 190
          Glu Xaa Thr Asp Leu Gln Lys Glu Gly Glu Phe Ser Thr Xaa Phe Thr
                       195                 200                 205
          Glu Leu Gln Arg Asp Phe Leu Lys Gln Arg Pro Thr Lys Leu Lys Ser
                       210                 215                 220
          Leu Ile Arg Leu Val Lys His Trp Tyr Gln Asn Xaa Lys Lys Lys Leu
          225                 230                 235                 240
          Gly Lys Leu Pro Pro Gln Tyr Ala Leu Glu Leu Leu Thr Val Tyr Ala
                       245                 250                 255
          Trp Glu Arg Gly Ser Met Lys Thr His Phe Asn Thr Ala Gln Gly Phe
                       260                 265                 270
          Arg Thr Val Leu Glu Leu Val Ile Asn Tyr Gln Gln Leu Xaa Ile Tyr
                       275                 280                 285
          Trp Thr Lys Tyr Tyr Asp Phe Lys Xaa Pro Ile Ile Glu Lys Tyr Leu
                       290                 295                 300
          Arg Arg Gln Leu Thr Lys Pro Arg Pro Val Ile Leu Asp Pro Ala Asp
          305                 310                 315                 320
          Pro Thr Gly Asn Leu Gly Gly Asp Pro Lys Gly Trp Arg Gln Leu
                       325                 330                 335
          Ala Gln Glu Ala Glu Ala Trp Leu Asn Tyr Xaa Xaa Phe Lys Asn Trp
                       340                 345                 350
          Asp Gly Ser Pro Val Ser Ser Trp Ile Leu Xaa
                       355                 360
```

<210> SEQ ID NO 16
<211> LENGTH: 362
<212> TYPE: PRT
<213> ORGANISM: Homo sapiens
<220> FEATURE:
<221> NAME/KEY: VARIANT
<222> LOCATION: (3)..(16)
<223> OTHER INFORMATION: Xaa = Lys OR -Lys (Lys deleted)
<220> FEATURE:
<221> NAME/KEY: VARIANT

```
<222> LOCATION: (41)..(41)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (47)..(47)
<223> OTHER INFORMATION: Xaa  = Asn OR Asp
<220> FEATURE:
<221> NAME/KEY: VARIANT
<222> LOCATION: (54)..(70)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (91)..(93)
<223> OTHER INFORMATION: Xaa = Asp OR Ala
<220> FEATURE:
<221> NAME/KEY: VARIANT
<222> LOCATION: (125)..(125)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (131)..(131)
<223> OTHER INFORMATION: Xaa = Phe OR Leu
<220> FEATURE:
<221> NAME/KEY: VARIANT
<222> LOCATION: (143)..(143)
<223> OTHER INFORMATION: Xaa  = Gly OR Arg
<220> FEATURE:
<221> NAME/KEY: VARIANT
<222> LOCATION: (178)..(178)
<223> OTHER INFORMATION: Xaa = Gly OR Ser
<220> FEATURE:
<221> NAME/KEY: VARIANT
<222> LOCATION: (193)..(285)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (296)..(296)
<223> OTHER INFORMATION: Xaa = Asn OR Thr
<220> FEATURE:
<221> NAME/KEY: VARIANT
<222> LOCATION: (346)..(346)
<223> OTHER INFORMATION: Xaa = Pro OR Ser
<220> FEATURE:
<221> NAME/KEY: VARIANT
<222> LOCATION: (347)..(347)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (362)..(362)
<223> OTHER INFORMATION: Xaa = Leu OR -Leu (Leu Deleted)

<400> SEQUENCE: 16

Met Lys Xaa Xaa Xaa Xaa Xaa Xaa Xaa Xaa Xaa Xaa Xaa Xaa Xaa Xaa
1               5                   10                  15

Gly Met Asp Leu Arg Asn Thr Pro Ala Lys Ser Leu Lys Phe Ile
            20                  25                  30

Glu Asp Tyr Leu Leu Pro Asp Thr Xaa Phe Arg Met Gln Ile Xaa His
        35                  40                  45

Ala Ile Asp Ile Ile Xaa Gly Phe Leu Lys Glu Arg Xaa Phe Arg Gly
    50                  55                  60

Ser Ser Tyr Pro Val Xaa Val Ser Lys Val Val Lys Gly Gly Ser Ser
65                  70                  75                  80

Gly Lys Gly Thr Thr Leu Arg Gly Arg Ser Xaa Ala Xaa Leu Val Val
            85                  90                  95

Phe Leu Ser Pro Leu Thr Thr Phe Gln Asp Gln Leu Asn Arg Arg Gly
            100                 105                 110
```

```
Glu Phe Ile Gln Glu Ile Arg Arg Gln Leu Glu Ala Xaa Gln Arg Glu
            115                 120                 125

Arg Ala Xaa Ser Val Lys Phe Glu Val Gln Ala Pro Arg Trp Xaa Asn
    130                 135                 140

Pro Arg Ala Leu Ser Phe Val Leu Ser Ser Leu Gln Leu Gly Glu Gly
145                 150                 155                 160

Val Glu Phe Asp Val Leu Pro Ala Phe Asp Ala Leu Gly Gln Leu Thr
                165                 170                 175

Gly Xaa Tyr Lys Pro Asn Pro Gln Ile Tyr Val Lys Leu Ile Glu Glu
        180                 185                 190

Xaa Thr Asp Leu Gln Lys Glu Gly Glu Phe Ser Thr Xaa Phe Thr Glu
    195                 200                 205

Leu Gln Arg Asp Phe Leu Lys Gln Arg Pro Thr Lys Leu Lys Ser Leu
210                 215                 220

Ile Arg Leu Val Lys His Trp Tyr Gln Asn Xaa Lys Lys Leu Gly
225                 230                 235                 240

Lys Leu Pro Pro Gln Tyr Ala Leu Glu Leu Leu Thr Val Tyr Ala Trp
                245                 250                 255

Glu Arg Gly Ser Met Lys Thr His Phe Asn Thr Ala Gln Gly Phe Arg
                260                 265                 270

Thr Val Leu Glu Leu Val Ile Asn Tyr Gln Gln Leu Xaa Ile Tyr Trp
            275                 280                 285

Thr Lys Tyr Tyr Asp Phe Lys Xaa Pro Ile Ile Glu Lys Tyr Leu Arg
        290                 295                 300

Arg Gln Leu Thr Lys Pro Arg Pro Val Ile Leu Asp Pro Ala Asp Pro
305                 310                 315                 320

Thr Gly Asn Leu Gly Gly Gly Asp Pro Lys Gly Trp Arg Gln Leu Ala
                325                 330                 335

Gln Glu Ala Glu Ala Trp Leu Asn Tyr Xaa Xaa Phe Lys Asn Trp Asp
                340                 345                 350

Gly Ser Pro Val Ser Ser Trp Ile Leu Xaa
                355                 360

<210> SEQ ID NO 17
<211> LENGTH: 367
<212> TYPE: PRT
<213> ORGANISM: Homo sapiens
<220> FEATURE:
<221> NAME/KEY: VARIANT
<222> LOCATION: (46)..(46)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (52)..(52)
<223> OTHER INFORMATION: Xaa  = Asn OR Asp
<220> FEATURE:
<221> NAME/KEY: VARIANT
<222> LOCATION: (59)..(75)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (96)..(98)
<223> OTHER INFORMATION: Xaa = Asp OR Ala
<220> FEATURE:
<221> NAME/KEY: VARIANT
<222> LOCATION: (130)..(130)
<223> OTHER INFORMATION: Xaa = Cys OR Ala OR Gly OR Met OR Ser OR Thr OR
      -Cys (Cys Deleted)
<220> FEATURE:
<221> NAME/KEY: VARIANT
<222> LOCATION: (136)..(136)
```

```
<223> OTHER INFORMATION: Xaa = Phe OR Leu
<220> FEATURE:
<221> NAME/KEY: VARIANT
<222> LOCATION: (148)..(148)
<223> OTHER INFORMATION: Xaa  = Gly OR Arg
<220> FEATURE:
<221> NAME/KEY: VARIANT
<222> LOCATION: (183)..(183)
<223> OTHER INFORMATION: Xaa = Gly OR Ser
<220> FEATURE:
<221> NAME/KEY: VARIANT
<222> LOCATION: (198)..(290)
<223> OTHER INFORMATION: Xaa = Cys OR Ala OR Gly OR Met OR Ser OR Thr OR
     -Cys (Cys Deleted)
<220> FEATURE:
<221> NAME/KEY: VARIANT
<222> LOCATION: (301)..(301)
<223> OTHER INFORMATION: Xaa = Asn OR Thr
<220> FEATURE:
<221> NAME/KEY: VARIANT
<222> LOCATION: (351)..(351)
<223> OTHER INFORMATION: Xaa = Pro OR Ser
<220> FEATURE:
<221> NAME/KEY: VARIANT
<222> LOCATION: (352)..(352)
<223> OTHER INFORMATION: Xaa = Cys OR Ala OR Gly OR Met OR Ser OR Thr OR
     -Cys (Cys Deleted)
<220> FEATURE:
<221> NAME/KEY: VARIANT
<222> LOCATION: (367)..(367)
<223> OTHER INFORMATION: Xaa = Leu OR -Leu (Leu Deleted)

<400> SEQUENCE: 17

Met Gly His His His His His His His His Ser Ser Gly His
1               5                   10                  15

Ile Glu Gly Arg His Met Met Asp Leu Arg Asn Thr Pro Ala Lys Ser
            20                  25                  30

Leu Asp Lys Phe Ile Glu Asp Tyr Leu Leu Pro Asp Thr Xaa Phe Arg
        35                  40                  45

Met Gln Ile Xaa His Ala Ile Asp Ile Ile Xaa Gly Phe Leu Lys Glu
    50                  55                  60

Arg Xaa Phe Arg Gly Ser Ser Tyr Pro Val Xaa Val Ser Lys Val Val
65                  70                  75                  80

Lys Gly Gly Ser Ser Gly Lys Gly Thr Thr Leu Arg Gly Arg Ser Xaa
                85                  90                  95

Ala Xaa Leu Val Val Phe Leu Ser Pro Leu Thr Thr Phe Gln Asp Gln
            100                 105                 110

Leu Asn Arg Arg Gly Glu Phe Ile Gln Glu Ile Arg Arg Gln Leu Glu
        115                 120                 125

Ala Xaa Gln Arg Glu Arg Ala Xaa Ser Val Lys Phe Glu Val Gln Ala
    130                 135                 140

Pro Arg Trp Xaa Asn Pro Arg Ala Leu Ser Phe Val Leu Ser Ser Leu
145                 150                 155                 160

Gln Leu Gly Glu Gly Val Glu Phe Asp Val Leu Pro Ala Phe Asp Ala
                165                 170                 175

Leu Gly Gln Leu Thr Gly Xaa Tyr Lys Pro Asn Pro Gln Ile Tyr Val
            180                 185                 190

Lys Leu Ile Glu Glu Xaa Thr Asp Leu Gln Lys Glu Gly Glu Phe Ser
        195                 200                 205

Thr Xaa Phe Thr Glu Leu Gln Arg Asp Phe Leu Lys Gln Arg Pro Thr
    210                 215                 220

Lys Leu Lys Ser Leu Ile Arg Leu Val Lys His Trp Tyr Gln Asn Xaa
225                 230                 235                 240
```

-continued

```
Lys Lys Lys Leu Gly Lys Leu Pro Pro Gln Tyr Ala Leu Glu Leu Leu
            245                 250                 255

Thr Val Tyr Ala Trp Glu Arg Gly Ser Met Lys Thr His Phe Asn Thr
            260                 265                 270

Ala Gln Gly Phe Arg Thr Val Leu Glu Leu Val Ile Asn Tyr Gln Gln
            275                 280                 285

Leu Xaa Ile Tyr Trp Thr Lys Tyr Tyr Asp Phe Lys Xaa Pro Ile Ile
    290                 295                 300

Glu Lys Tyr Leu Arg Arg Gln Leu Thr Lys Pro Arg Pro Val Ile Leu
305                 310                 315                 320

Asp Pro Ala Asp Pro Thr Gly Asn Leu Gly Gly Gly Asp Pro Lys Gly
                325                 330                 335

Trp Arg Gln Leu Ala Gln Glu Ala Glu Ala Trp Leu Asn Tyr Xaa Xaa
            340                 345                 350

Phe Lys Asn Trp Asp Gly Ser Pro Val Ser Ser Trp Ile Leu Xaa
        355                 360                 365
```